(12) United States Patent
Ziarno et al.

(10) Patent No.: US 8,679,013 B2
(45) Date of Patent: Mar. 25, 2014

(54) INTRAVAGINAL MONITORING DEVICE

(76) Inventors: Witold Andrew Ziarno, Thalheim (DE); James D. Bennett, Hroznetin (CZ)

( * ) Notice: Subject to any disclaimer, the term of this patent is extended or adjusted under 35 U.S.C. 154(b) by 413 days.

(21) Appl. No.: 12/890,743

(22) Filed: Sep. 27, 2010

(65) Prior Publication Data

US 2011/0190579 A1    Aug. 4, 2011

Related U.S. Application Data

(60) Provisional application No. 61/246,375, filed on Sep. 28, 2009, provisional application No. 61/246,405, filed on Sep. 28, 2009, provisional application No. 61/246,396, filed on Sep. 28, 2009, provisional application No. 61/290,792, filed on Dec. 29, 2009, provisional application No. 61/263,416, filed on Nov. 23, 2009.

(51) Int. Cl.
*A61B 5/00*  (2006.01)
*G06F 19/00*  (2011.01)

(52) U.S. Cl.
CPC ..................... *G06F 19/34* (2013.01)
USPC ............................ 600/301; 600/135; 600/591

(58) Field of Classification Search
USPC ................. 600/135–136, 300–301, 476, 591
See application file for complete search history.

(56) References Cited

U.S. PATENT DOCUMENTS

| | | | |
|---|---|---|---|
| 5,096,830 A | 3/1992 | Senyei et al. | |
| 6,200,279 B1 | 3/2001 | Paltieli | |
| 6,450,977 B1 | 9/2002 | Baxter-Jones | |
| 6,669,653 B2 | 12/2003 | Paltieli | |
| 6,741,895 B1 | 5/2004 | Gafni et al. | |
| 6,896,653 B1 | 5/2005 | Vail, III et al. | |
| 6,994,678 B2 | 2/2006 | Baxter-Jones et al. | |
| 7,154,398 B2 | 12/2006 | Chen et al. | |
| 7,207,941 B2 * | 4/2007 | Sharf | 600/438 |
| 7,628,744 B2 * | 12/2009 | Hoffman et al. | 482/148 |
| 7,762,945 B2 | 7/2010 | Blumenthal | |
| 7,850,625 B2 | 12/2010 | Paltieli et al. | |
| 7,937,249 B2 * | 5/2011 | Osborn et al. | 703/2 |
| 2002/0198473 A1 * | 12/2002 | Kumar et al. | 600/595 |
| 2005/0049509 A1 * | 3/2005 | Mansour et al. | 600/476 |
| 2005/0203399 A1 | 9/2005 | Vaezy et al. | |
| 2005/0267377 A1 * | 12/2005 | Marossero et al. | 600/511 |
| 2006/0149597 A1 | 7/2006 | Powell et al. | |
| 2007/0112284 A1 * | 5/2007 | Hoffman et al. | 600/591 |
| 2008/0071190 A1 * | 3/2008 | Gorodeski et al. | 600/551 |
| 2008/0146887 A1 * | 6/2008 | Rao et al. | 600/300 |

(Continued)

FOREIGN PATENT DOCUMENTS

| | | |
|---|---|---|
| CA | 2 608 497 | 8/2006 |
| CN | 101194278 | 6/2008 |

(Continued)

*Primary Examiner* — Bill Thomson
*Assistant Examiner* — Bobby Soriano
(74) *Attorney, Agent, or Firm* — Da Vinci Partners LLC; John Moetteli

(57) ABSTRACT

The invention relates to an intravaginal monitoring device, method of intravaginal monitoring, and system and network for intravaginal monitoring. The intravaginal monitoring device and or network includes multiple modes of operation that enable non-pregnancy monitoring, pregnancy testing, pregnancy monitoring, STD detection, precancerous condition monitoring, cancerous condition monitoring, pre-birth monitoring and prediction, neo-natal monitoring, ovulation monitoring, an automated rhythm method, among various applications of the device, method and network of the present invention.

23 Claims, 27 Drawing Sheets

(56) References Cited

U.S. PATENT DOCUMENTS

| | | | |
|---|---|---|---|
| 2009/0076368 A1* | 3/2009 | Balas | 600/407 |
| 2009/0143646 A1* | 6/2009 | Vail, III | 600/135 |
| 2009/0185096 A1 | 7/2009 | Park | |
| 2009/0222058 A1* | 9/2009 | Craggs | 607/41 |
| 2009/0281397 A1* | 11/2009 | Lavoisier | 600/301 |
| 2010/0009336 A1* | 1/2010 | Sullivan | 435/3 |
| 2010/0016668 A1 | 1/2010 | Gal | |
| 2010/0036279 A1* | 2/2010 | Rieth | 600/551 |
| 2010/0081895 A1* | 4/2010 | Zand | 600/309 |
| 2010/0235782 A1 | 9/2010 | Powell et al. | |

FOREIGN PATENT DOCUMENTS

| | | |
|---|---|---|
| WO | WO 2006/086089 | 8/2006 |
| WO | WO 2010/105063 | 9/2010 |
| WO | WO 2010/144413 | 12/2010 |

* cited by examiner

INTRAVAGINAL MONITORING DEVICE

CROSS-REFERENCE TO RELATED APPLICATIONS

This application incorporates by reference herein in their entirety and makes reference to, claims priority to, and claims the benefit of:

a) U.S. Provisional Application Ser. No. 61/246,375 filed Sep. 28, 2009, entitled "Intravaginal Monitoring Device" by Ziarno et al.;

b) U.S. Provisional Application Ser. No. 61/246,405 filed Sep. 28, 2009, entitled "Network Supporting Intravaginal Monitoring Device, Method and Post Harvesting Processing of Intravaginally Processed Data" by Ziarno et al.;

c) U.S. Provisional Application Ser. No. 61/246,396 filed Sep. 28, 2009, entitled "Network Supporting Intravaginal Monitoring Device" by Ziarno et al.

d) U.S. Provisional Application Ser. No. 61/290,792 filed Dec. 30, 2009, entitled "Network Supporting Intravaginal Monitoring Device, Method and Post Harvesting Processing of Intravaginally Processed Data" by Ziarno et al.; and e) U.S. Provisional Application Ser. No. 61/263,416 filed Nov. 23, 2009, entitled "Intravaginal Monitoring Architecture" by Ziarno et al.

Also incorporated herein by reference in their entirety are:

a) U.S. patent application Ser. No. 12/890,750 filed on 27 Sep. 2010 by Bennett et al., entitled "Network Supporting Intravaginal Monitoring Device";

b) U.S. patent application Ser. No. 12/890,764 filed on 27 Sep. 2010 by Bennett et al., entitled "Analysis Engine within a Network Supporting Intravaginal Monitoring";

c) U.S. patent application Ser. No. 12/890,805 filed on 27 Sep. 2010 by Bennett et al., entitled "Intravaginal Monitoring Support Architecture";

d) U.S. patent application Ser. No. 12/890,811 filed on 27 Sep. 2010 by Bennett et al., entitled "Intravaginal Therapy Device";

e) U.S. patent application Ser. No. 12/890,830 filed on 27 Sep. 2010 by Bennett et al., entitled "Intravaginal Dimensioning System"; and f) U.S. patent application Ser. No. 12/890,847 filed on 27 Sep. 2010 by Bennett et al., entitled "Intravaginal Optics Targeting System"; and g) PCT Patent Application Ser. No. PCT/US2010/050329 filed on 27 Sep. 2010 by Bennett et al., entitled "Intravaginal Monitoring Device and Network".

BACKGROUND

1. Technical Field

The invention generally relates to medical devices, and more particular to medical devices used in obstetrics and gynecology.

2. Related Art

Currently in the art there is no convenient way for a female to easily monitor her cervical and vaginal health, without a doctor's visit, both during non-pregnancy and pregnancy.

With respect to pregnancy, premature effacement (shortening of the vaginal portion of the cervix and thinning of the walls) and dilation of the cervix is not caused by labor, but rather by structural weakness in the cervix itself. This is called cervical incompetence. The weakness can result from a number of conditions, most due to prior injury to the cervix or resulting from an inherited physical condition of the cervix.

When the cervix is damaged, it cannot hold the weight of the pregnancy. The cervix dilates without contractions or pain, sometimes opening completely. The dilation results in the amniotic membranes bulging through the opening and eventually rupturing, often before the baby can survive outside of the uterus. This irritates the uterus and brings on pre-term labor. In many cases, labor is detected when it is too far advanced to stop the process. Cervical incompetence counts for about 15 to 20 percent of all pregnancy losses during the second trimester. Risk factors for an incompetent cervix are: a history of incompetent cervix with a previous pregnancy, surgery, cervical injury, DES (diethylstilbestrol) exposure, and anatomic abnormalities of the cervix.

Other causes of cervical weakness include cervical cautery (to remove growths or to stop bleeding) and cone biopsy (removal of a cone-shaped section of tissue for study to detect possible precancerous growth). Prior to pregnancy or during the first trimester, there is usually no method to determine whether the cervix will eventually be incompetent.

Women with incompetent cervix typically present with "silent" cervical dilation (i.e., with minimal uterine contractions) between 16 and 28 weeks of gestation. They present with significant cervical dilation (2 cm or more), shortening of the cervix, and minimal symptoms. When the cervix reaches 4 cm or more, active uterine contractions or rupture of membranes may occur. Once the problem of incompetence is diagnosed, the condition may be treatable through a surgical procedure called cerclage (stitching the cervix closed). One or more stitches are placed around or through the cervix to keep it tightly closed. This is usually performed after the twelfth week of pregnancy the time after which a woman is least likely to miscarry for other reasons—but it is not done if there is rupture of the membranes or infection. Other treatments or therapies are applied to cervix, e.g. a cervical prosthesis or drug therapy. The efficacy of these treatments depends on timely identification of cervical incompetence.

After one or more of these therapies, the mother is carefully monitored to check for infection and contractions, which are sometimes brought on by the procedure. After hospital discharge, the patient may remain on bedrest in order to remove any pressure on the cervix and increase the chance of retaining the pregnancy until the baby is viable. The cerclage is usually removed just before childbirth so that the patient can give birth vaginally. In some cases, the cerclage may be left in place, and the baby is then delivered by cesarean section. If cervical incompetence or other abnormal cervical changes, are caught in a timely manner, treatments have proved very effective.

These and other limitations and deficiencies associated with the related art may be more fully appreciated by those skilled in the art after comparing such related art with various aspects of the present invention as set forth herein with reference to the figures.

BRIEF SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

DETAILED DESCRIPTION OF THE DRAWINGS

Figure 1:
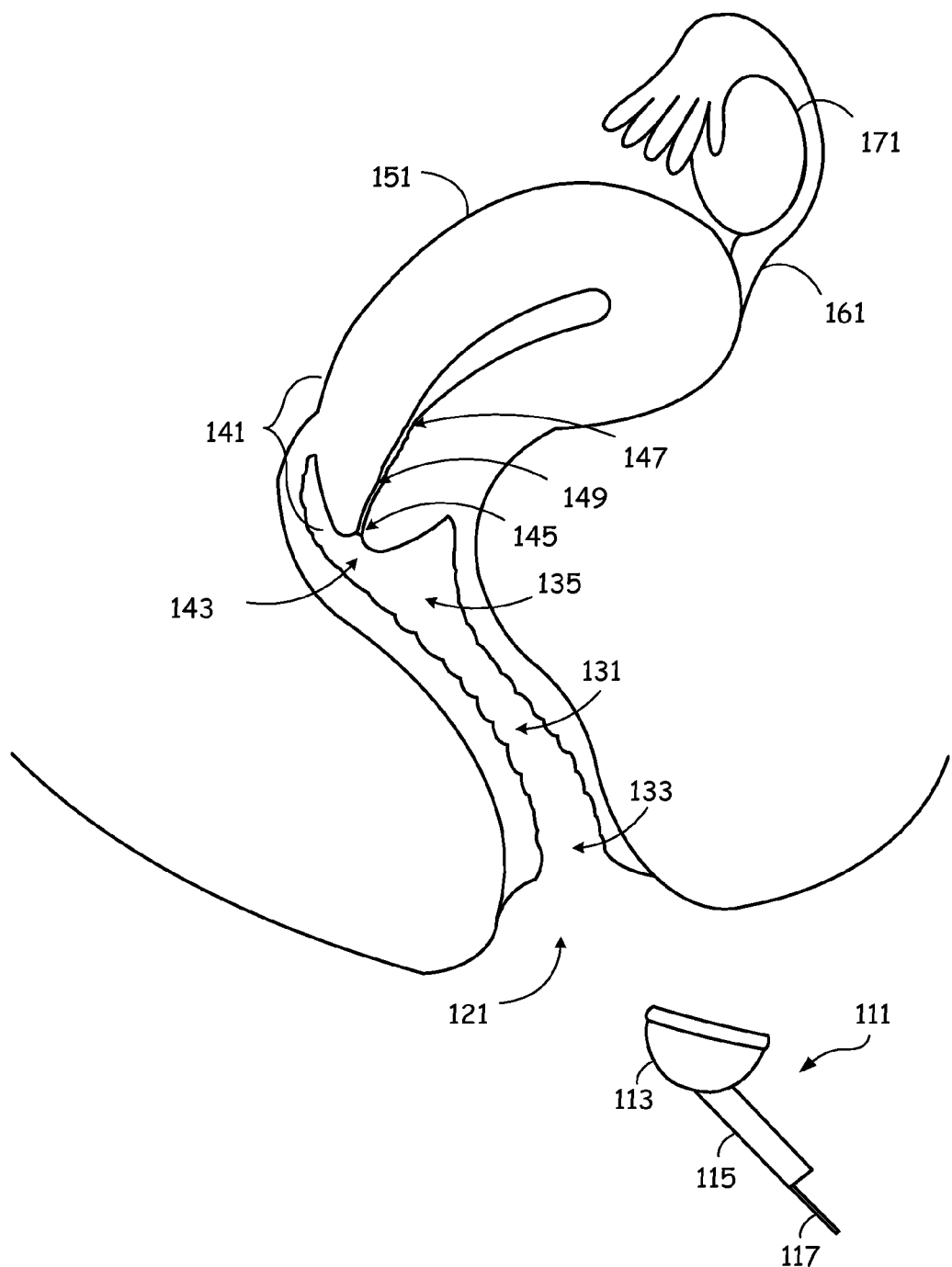
FIG. 1 is a schematic diagram illustrating an intravaginal monitoring device; wherein the device's cap or head, when pushed via the vaginal channel to face the outer surface of the cervix, takes images of the outer surface of the cervix as well as sensor readings via many of the built-in electronic sensors, to monitor the well being of a female and/or developing fetus, by the individual female or health care professionals.

FIG. 1 is a schematic diagram illustrating an intravaginal monitoring device 111; wherein the device's cap or head 113, when pushed via vaginal channel 131 to face outer surface of the cervix 141, takes images of the outer surface of the cervix 141 as well as sensor readings via many of the built-in electronic sensors, to monitor the well being of a female and/or developing fetus, by an individual female or health care professionals. It is understood that when reference is made to the female reproductive system this also includes, by way of further example, the reproductive system of a pregnant female and that device 111 takes sensor readings related to the pregnant female as well as the being within the pregnant female's womb.

Typically, reproductive health and well being of a female is monitored by a gynecologist, obstetrician and or veterinarian using a speculum, during routine checkups, menstrual cycles, menopause, sexually transmitted diseases and pregnancy checkups (may also include pre and/or post coitus periods); which necessitates the presence of the female in question at the gynecologist's office, clinic, hospital or facility. Using the intravaginal monitoring device 111 and some preliminary knowledge of reproductive health and well being, the female may herself observe and monitor the cervix, and changes thereof (and the vaginal discharges thereon) and be able to take many sensor readings (and hence be able to initially judge health conditions, possibly, in conjunction with a health care and or veterinary professional). And in case of any observable discrepancies, during the course of a female's lifetime, during pregnancy or during normal occurrences of pre and post coitus (due to any concerns about STD infection) or at all other periods, or upon periodic request by a health care specialist (gynecologist, obstetrician or veterinarian), the sensor readings and images obtained via the intravaginal monitoring device 111 may be utilized in taking precautionary actions. Similarly, sensor readings are taken of non-human animals.

It is appreciated that the device 111 is sized and dimensioned to be used in any animal. Particularly, the device has human uses, but also can be used in the veterinary context to provide data on mammals, e.g. prize race horses, cattle, and other domestic or wild animals. The caps and housings of the devices described herein are appropriated tailored in size and dimension to be used in non-human animals.

A visual image typically allows the individual female or a gynecologist, obstetrician and or veterinarian to verify the health conditions. For instance, fluid discharges observed via a moving image video clip (including single image, multiple image, short video clips, medium video clips, or long term video clips), when transferred to a gynecologist's, medical professional's, obstetrician's, or veterinarian's and or technician's computer (or in other variants, mobile phone, smart phone, PDA, or other consumer electronic device), may allow the gynecologist or other professional to prescribe and know the actions to be taken for treatment, therapy of further observation. The fluid discharge and or spotting may indicate conditions such as normal (small amount of clear or slightly milky vaginal discharge), menstrual cycle, menopause, infections or STD—sexually transmitted diseases—(much more discharge than normal, or it is discoloured). By way of example, the STDs may include Gardnerella (greyish, foamy discharge, with a strong fishy smell), Candida (thick creamy whitish discharge, with a yeasty smell), Chlamydia (increased vaginal discharge), Gonorrhoea (yellow or greenish discharge with a strong smell), Trichomonas (TV) (a frothy discharge, sometimes a yellowy-green color), human papiloma virus (HPV)(white or other color lesions on the cervix), and so forth. In addition, lumps and bumps due to ingrowing hairs, acne spots, and blocked glands can also be observed via images. By way of further example, cervical abnormalities, such as growths, genital warts, precancerous cells, cysts, cancerous cells, are also observed via the images taken by device 111.

In all of these cases, the temperature readings are also a useful guide to a gynecologist, user or other medical or veterinary professional. Additional sensor readings such as pressure sensors and PH sensors are also useful guide in determining the reproductive health condition of a female or condition of the vaginal and or cervical tissue. Additionally, including pregnancy (e.g. first, second or third trimester), a female's reproductive health is observed using the intravaginal monitoring device 111, directly or indirectly (e.g. by a gynecologist, obstetrician, family practice physician, veterinarian, midwife, nurse), to determine the health conditions), include Vulva 121, Vaginal Channel 131, Exterior Portion of Vaginal Channel 133, Interior Portion of Vaginal Channel 135, Cervix 141, Outer Surface of Cervix 143, Exterior Orifice (opening) of Cervix 145, Interior Orifice 147, Cervical Channel 149, Uterus 151, Fallopian Tube 161, and Ovary 171. Abnormalities further up the female reproductive tract can manifest as visually detectable manifestations such as abnormal discharge through the cervical OS.

The intravaginal monitoring device 111 itself, in one variant, contains a cap or head 113 (that contains some or all of the built in electronics), stem 115 (that aids user in insertion/ removal and stabilization/orientation during wear) and finger ring 117 that assists insertion/removal. The stem 115, in some configurations, also contains built in electronics. The cap 113 and stem 115 includes one or more of camera and illumination system, sensors, user interfaces, power management system, communication interfaces. The sensors include, by way of further example, temperature sensors, pressure sensors, glucose sensing, PH sensing, EKG, microbe sensors, DNA sensors, RNA sensors, protein sensors, drug sensors and an optional sonogram. Other sensor systems that assist in determining other gynecological or obstetric conditions (and in cases of other needs for physiological reproductive data or intravaginal health data) are also used herein, in other variants. Also, the intravaginal monitoring device 111 insertion optionally begins by applying a lubricant (e.g. an oil, a gel, a spermicidal gel, or other female intravaginal lubricant) on the surface of the cap 113 or other portion of device 111.

Features that are incorporated in various embodiments of the intravaginal monitoring device 111 of the present invention include: (a) Camera unit containing wide angle lensing as well as "fish eye" lensing and image recovery; (b) Transparent latex used to cover the device for use and to protect the lensing cap of some of the designs (also extends the life of the medical grade rubber device, e.g. disposable sheaths or sleeves that are placed over the device); (c) Time stamping all sensor data capture (to be able to follow up and investigate the vaginal conditions by a healthcare professional); (d) Live video used for guidance of the device into place; and (e) Linear, symmetric device with a very flexible neck and stem to assist in fitting the space; and (f) Making the intravaginal monitoring device able to bend and face toward cervix (straight ahead, in a line of sight; note that the female person may partly have to work the intravaginal monitoring device 111 to make it orient properly,—this can also be accomplished by viewing the images in an external device).

In addition, there are multiple variants of the device 111. Two exemplary types of the intravaginal monitoring devices 111 include a first one that is wearable (for continuously wearing during day, night or other periods, and for long term monitoring) and the second one is non-wearable (for shorter term monitoring and quick assessments in the gynecologist's, veterminary professional's, or other medical professional's presence, for example). These two exemplary types come in different shapes and sizes, depending upon their applications and female in question. For example, the device 111 is sized and dimensioned to comfortably fit an average Asian, Caucasian, Negro, and or Indian vagina. They are constructed of medical grade silicon or other suitable biocompatible material for flexibility and adjustability of the cap or head, to snugly fitting into the cervix area 143, in one variant. Other types of plastics, glass, acrylic, or rubber are also used in other variants. Moreover, the cap 113 (or head 113, shaped like a bulb) is constructed of a medical grade silicon rubber cap, with some or most of the electronics fit into the bottom of the cap or inside the stem with user interfaces being visible externally (for the images and sensor readings to be transmitted to a video system such as phone, smart phone, camera, television, lap top computer, desk top computer, terminal, and so forth, or transmitted to a health care center via Internet and a server). All of the electronics and user interfaces are placed within the hermetically sealed areas of the intravaginal monitoring device 111, so as to be able to handle vaginal discharges, and then be able to wash and clean after use free of damage to the optical assembly or electronics of the device in one variant.

Figure 2:
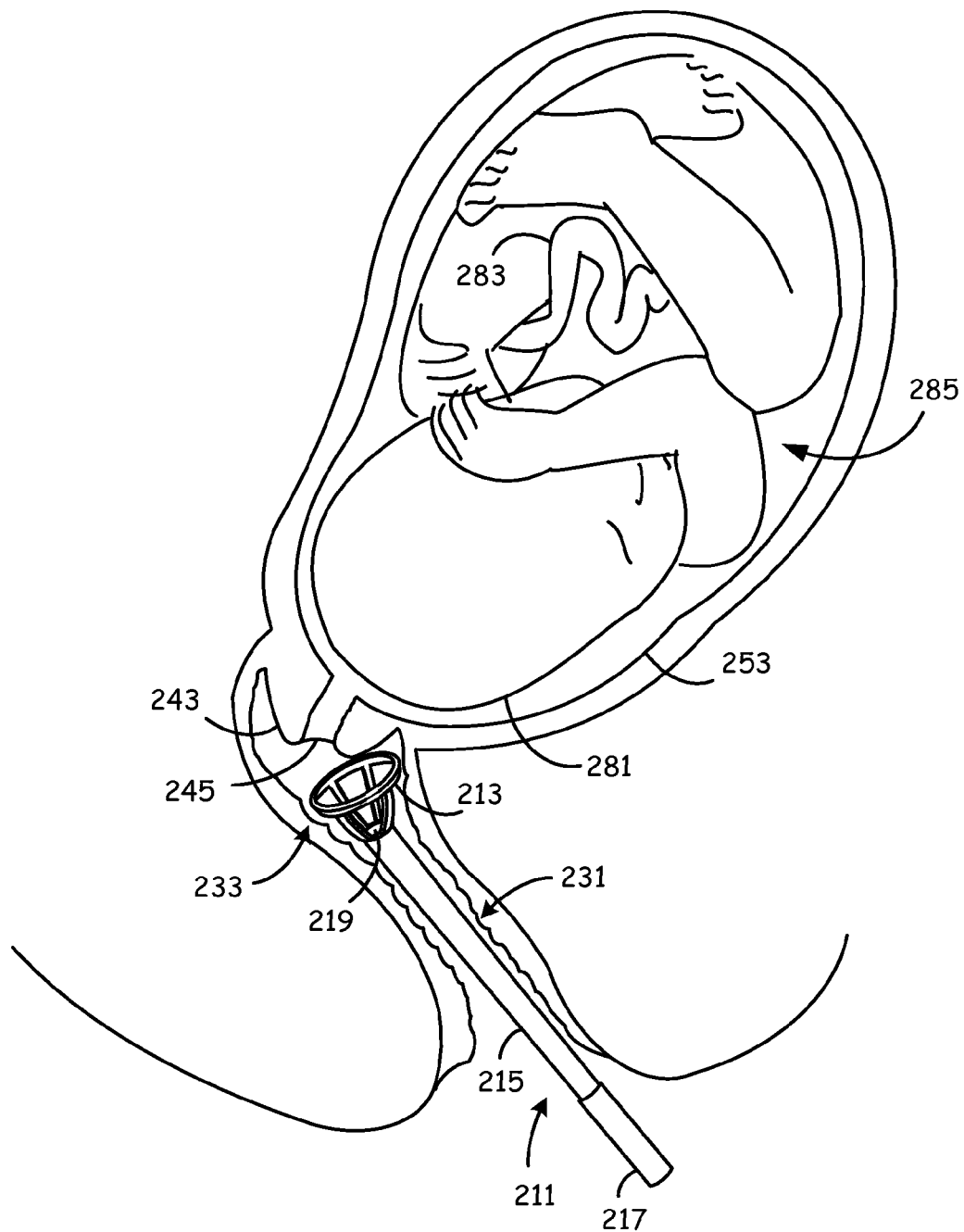
FIG. 2 is a schematic diagram illustrating placement of the intravaginal monitoring device of FIG. 1, placed so as to face the outer surface of the cervix; wherein the device's cap or head takes images of the outer surface of the cervix as well as sensor readings via many other built-in electronic sensors, to monitor the well being of a pregnant female and developing fetus.

FIG. 2 is a schematic diagram illustrating placement of the intravaginal monitoring device 211 of FIG. 1, placed so as to face the outer surface of the cervix 243; wherein the device's cap or head 213 takes images (still or video) of the outer surface of the cervix as well as sensor readings via many other built-in electronic sensors, to monitor the well being of a pregnant female and developing fetus 281. In the illustration, a non-wearable intravaginal monitoring device 211, that has perforated cap to allow flow of vaginal discharges, is shown.

A female's motherhood begins with conception, that occurred naturally or via assisted reproductive technology (that involves artificially transferring fertilized human egg into the female's uterus—in vitro fertilization). From then onwards, until the delivery of the baby, a regular and periodic monitoring is essential to avoid any complications that may harm the fetus 281 or the female herself. The fetus 281 may be harmed, for instance, when the umbilical cord 283 entangles the developing fetus 283 (within the uterine walls 253) or when the developing fetus 281 is not properly positioned, close to delivery periods, with head facing toward the cervix. In yet other exemplary conditions, the device 111 and method described herein is used to detect conditions related to an incompetent cervix. This condition is particularly harmful in that cervix can prematurely open, and the fetus 283 is delivered pre-term. The device 111 is used to detect conditions associated with cervical incompetence and in another variant of the invention, a therapy is provided, e.g. cervical suturing or cervical rings, along with other standard treatments and protocols. It is appreciated that the method of therapy including the use of the device 111 along with the subsequent medical intervention and therapy will permit the fetus 283 to proceed to full term or almost full term delivery. As such, harm to the fetus 283 is minimized as well as the downstream medical costs associated with care of a preterm infant. The fetus develops as each additional day, and week is added to its in womb gestation.

Typically, regular and periodic monitoring is expensive, time consuming, and inefficient, and necessitates constant monitoring by a trained healthcare professional (such as a midwife, nurse or gynecologist). In this age of strain on the global healthcare system, device 111, 211 provides a vehicle for reducing healthcare costs, as well as providing access to the best medical expertise which may be located at remote locations from the female, and which may provide the best option for evaluation and therapy provision. Moreover, the intravaginal monitoring device 211 allows the trained healthcare professional or the individual female herself to observe and monitor the changes that occur in the cervix area 243, at home, at the workplace or outside the clinical setting. Time is of the essence with respect to catching abnormal cervical changes. Once the point of no return is reached, e.g. the cervix reaching a critical OS opening, therapies cannot be provided the female. The device and telemedicine system described herein provides for real time notification and alerts of these abnormal cervical changes, permitting therapies to be timely provided, and the gestation period of a fetus to be extended in the womb. This can prevent the fetus from suffering from lifelong conditions that typically result from being born prematurely, e.g. conditions affecting sight, the lungs, etc.

By way of example, with respect to sexually active females and where multiple sex partners participate in unprotected sex with a particular female, the device 211, permits the female to check on disease state changes in her vagina and cervix between sex partners. By way of further example, a female takes baseline data harvest using device 211 of her cervix and vagina at a first point in time. She engages in unprotected sex with a male. She uses the device 211 to take a second data harvest after the act of coitus. A comparison of the baseline data harvest with the second (or subsequent) data harvest are made. One of two scenarios develop. In the first scenario, there is no detectable change. In a second scenario, there is a detectable change. In this case, the detectable change may be associated with infection with an STD. The device is used for immediate or rapid determination of a condition that needs to be treated. The medical professional has the required data for analysis purposes, including the baseline data harvest and the second data harvest. The female's infected sex partner is then notified that he also is need of immediate treatment. The notification of all involved occurs by mobile phone, email, sms, or other communication means. It is appreciated that this rapid detection prevents both the newly infected female and the infected male to treat their respective conditions, and stops the chain of STD infection in the event that either the infected male or female have additional sex partners. Hence, the public health ramifications of use of the device 211 with respect to stopping the proliferation of STDs are significant.

Other reproductive parts shown in the illustration include amniotic fluids 285, cervical channel 249, exterior orifice 245, exterior portion of the vaginal channel 233 and the vaginal channel 231. The device described herein detects the breaking of the amniotic sack as manifested by fluid discharge, e.g. rapid or slow, from the cervical OS. Indeed, the device also images protrusion of the amniotic sack or fetus through the cervical OS in another variant.

The illustration of the non-wearable intravaginal monitoring device 211, to which optionally monitors neonatal development, is used for shorter term monitoring, in one variant of the invention. By way of example, the monitoring is for a period of minutes, hours, and or days, or a combination of varying periods of time, e.g. periodic sessions. Device 211 provides for intravaginal insertion of a portion (a cap 213 with a wheel and spoke configuration and stem 215) via a wearer hand-grip portion 217. The cap 213 is shaped, dimensioned and sized to spread the interior portion of the vaginal channel, but may also be inserted onto the outer surface of the cervix 243. Spreading or separation of tissue located at the interior portion of the vaginal channel permits an open field of view of some or all of the cervix, permitting proper imaging of the cervix, e.g. with a digital imager. Moreover, the cap 213 folds for insertion, easy of placement, and positioning, comfort and fitting. The openings between spokes of the cap 213 permit vaginal discharges to flow and the curved spokes of the cap 213 bend outward upon wheel contact to clear the view. The stem 215 contains built in electronics supporting the various sensors, communication systems and all of the functionalities that includes capturing still and moving images, and taking various sensor readings. The stem 215 also aids the wearer in insertion/removal and stabilization/orientation during wear. In another variant of the invention, stem 215 is optional, e.g. where the electronics and sensors are located solely in the cap portion of device. In this case a string is attached to the cap to permit the female to remove the device after sensing and images sessions.

Figure 3:
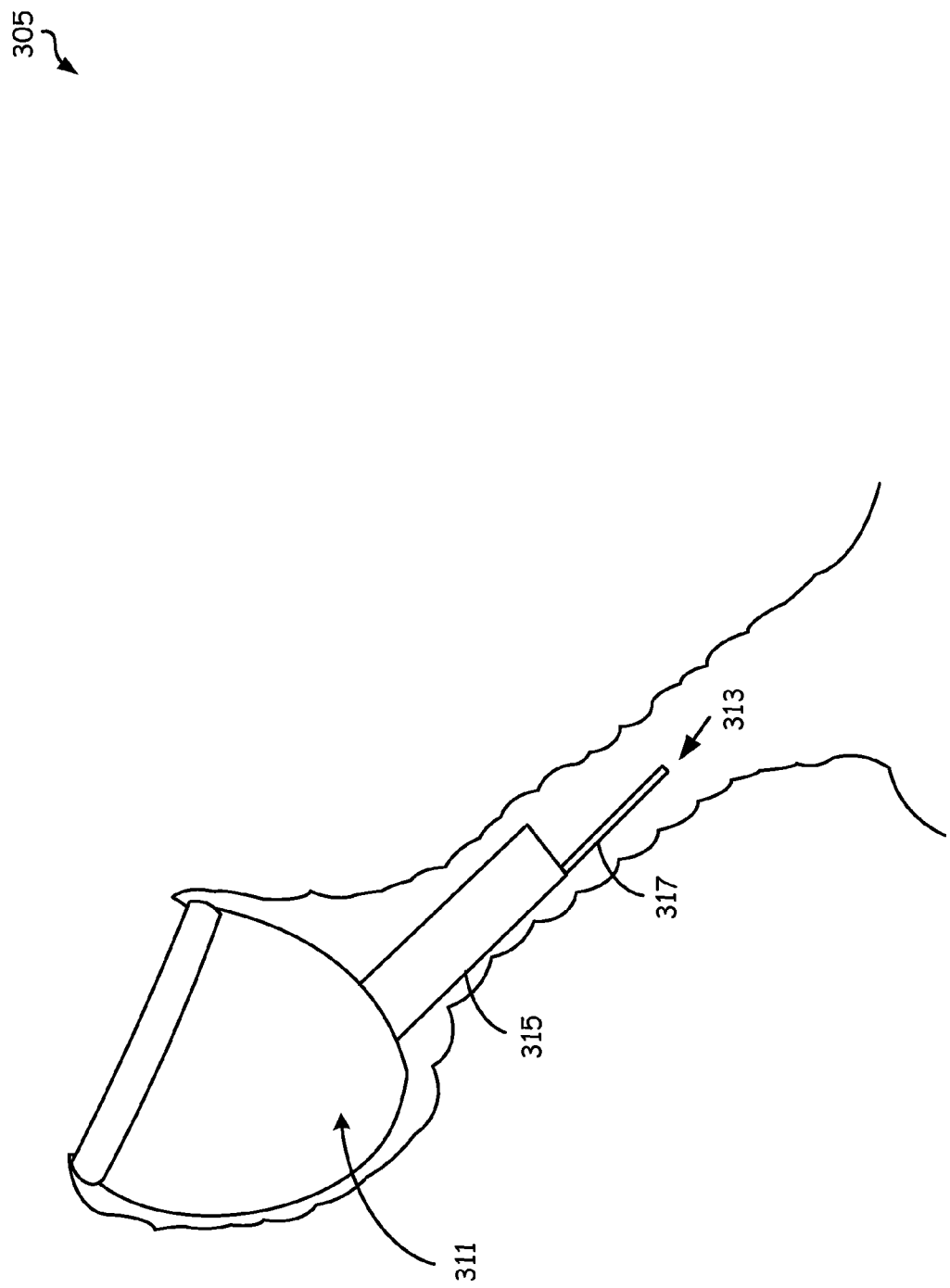
FIG. 3 is a schematic diagram illustrating a first of the embodiments of the intravaginal monitoring device of FIG. 1, having an angled multi-sized cap or head, placed so as to face and fit the outer surface of the cervix.

FIG. 3 is a schematic diagram illustrating a first of the embodiments of the intravaginal monitoring device 313 of FIG. 1, having an angled multi-sized cap or head 311, placed so as to face and fit the outer surface of the cervix. The illustration shows a wearable intravaginal monitoring device 313 (that can be used continuously over a prolonged period of time in variant) that consists of a stem 315 and a finger ring 317 that assists insertion and removal of the intravaginal monitoring device 313. The electronics that is part of the intravaginal monitoring device 313 is not shown in this figure; nonetheless, they are incorporated within the cap 311 and the stem 315. The stems described herein are also slightly curved. Curvature of the stem provides for comfort and ease of insertion and position of the device. In a variant, the curvature conforms to a natural curvature of an individual female vagina.

The shape of the cap 311, in an embodiment, is not symmetrical; instead it is angled so as to not only face the outer surface of the cervix but also so that the top ring perfectly or semi perfectly fits the outer surface of the cervix. In other words, the top ring of the intravaginal monitoring device 313 and the cap 311 itself are angled so as to fit snugly in front of the outer surface of the cervix, without any gap between the top ring and the outer surface of the cervix in one variant.

Figure 4:
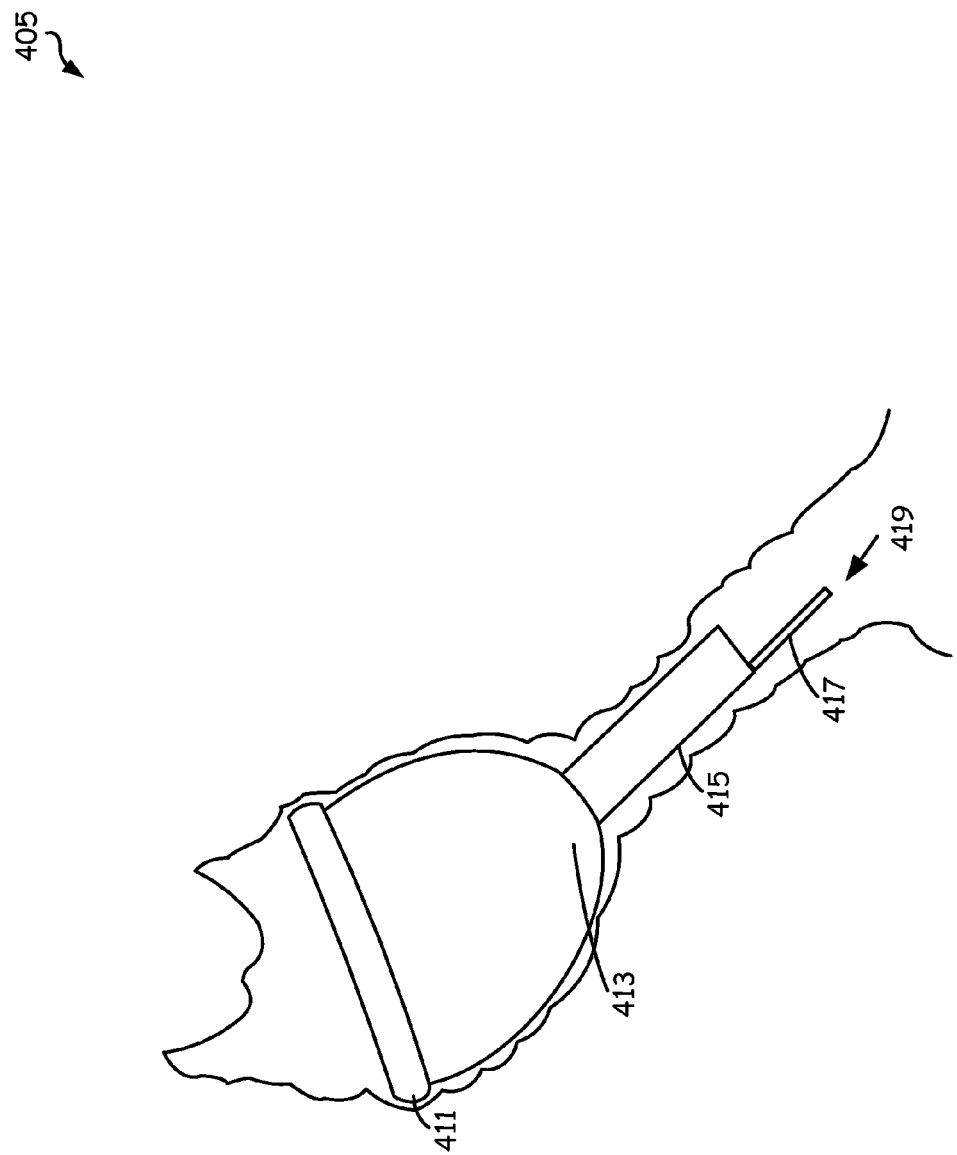
FIG. 4 is a schematic diagram illustrating a second of the embodiments of the intravaginal monitoring device of FIG. 1, having a straight multi-sized cap or head, placed so as to face the outer surface of the cervix.

FIG. 4 is a schematic diagram illustrating another embodiment of the intravaginal monitoring device 419 of FIG. 1, having a straight multi-sized cap or head 413, placed so as to face the outer surface of the cervix. The illustration shows a wearable intravaginal monitoring device 419 (that can be used over a prolonged period of time, by way of example) that consists of a stem 415 and a finger ring 417 (to enable a user or other person to readily insert and remove the intravaginal monitoring device 419). The electronics that is part of the intravaginal monitoring device 419 is not shown in this figure; nonetheless, they are incorporated within the cap 413 and the stem 415.

The shape of the cap 413, in this embodiment, is not symmetrical; instead it is designed to fit the female's vaginal anatomy and comes with close to a zero degree angle so as to only face the outer surface of the cervix. Three or more different sizes and dimensions, as applicable to different types of vaginal anatomy, are also provided.

To put it differently, the top ring 411 of the intravaginal monitoring device 419 and the cap 413 itself are slightly angled so as to fit snugly in front of the outer surface of the cervix, with a small gap between the top ring 411 and the outer surface of the cervix in one variant.

Figure 5:
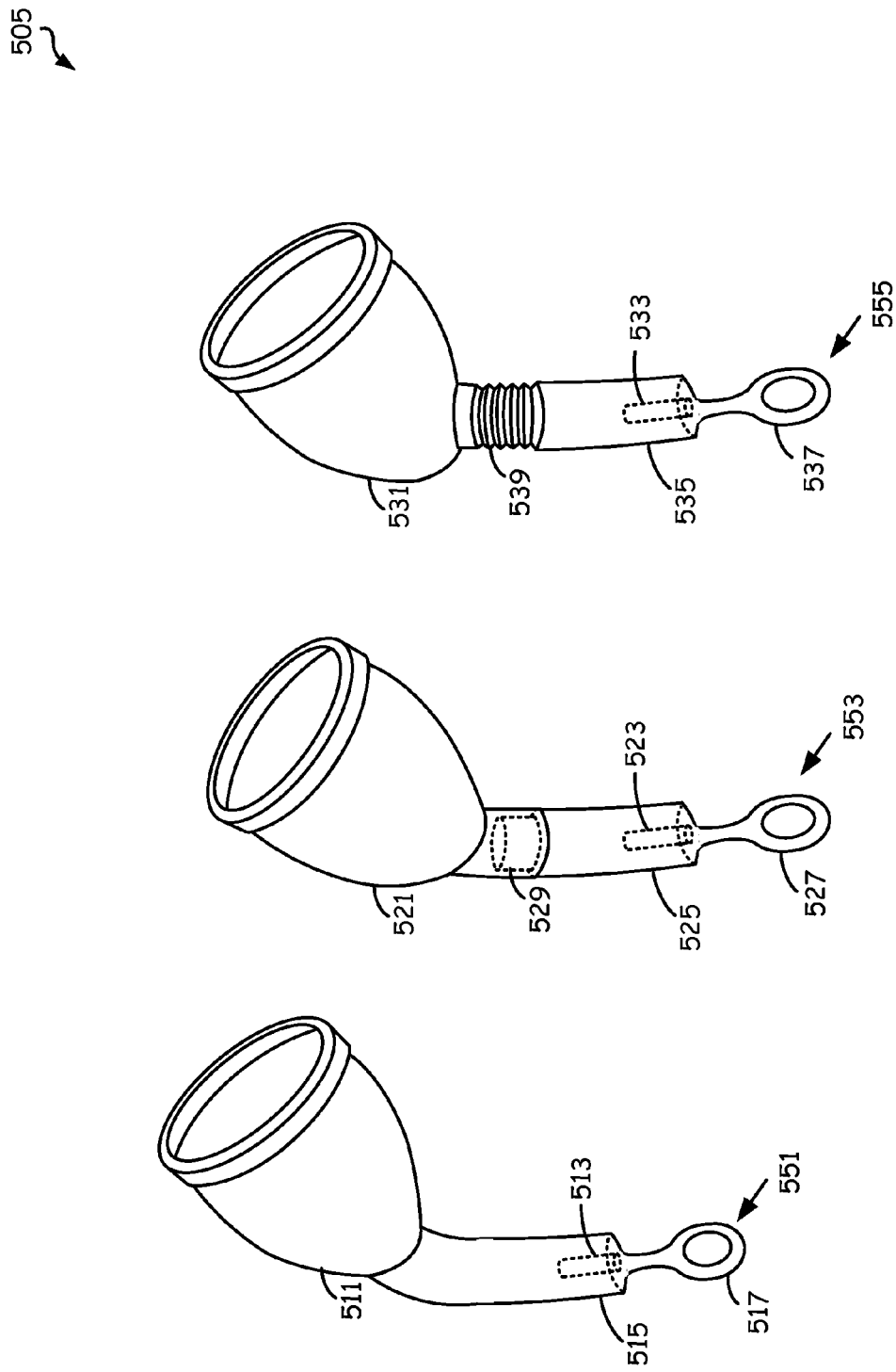
FIG. 5 is a schematic diagram illustrating three different wearable forms of the intravaginal monitoring device of FIG. 1 that are part of a kit, each possessing varyingly angled cap and some others having adjustable angles of the cap.

FIG. 5 is a schematic diagram illustrating three different wearable forms of the intravaginal monitoring device 551, 553, 555 of FIG. 1 that are part of a kit, each possessing varyingly angled caps 511, 521, 531 and some others having adjustable angles of the cap. The illustration shows three different types (of course, more or less than three different types are also provided) of wearable intravaginal monitoring devices 551, 553, 555 (that can be used over a short period or time or prolonged period of time) that consists of a stem 515, 525, 535 and a finger ring 517, 527, 537 (to be able to insert and remove the intravaginal monitoring device 551, 553, 555). The electronics that is part of the intravaginal monitoring device 551, 553, 555 is not shown in this figure; nonetheless they are incorporated within the cap 511, 521, 531, the stem 515, 525, 535, or combination thereof with appropriate connectors (e.g. mechanical, optical or electrical).

Each of the designs of the intravaginal monitoring devices 551, 553, 555 vary slightly and are applicable for different conditions, events, situations and circumstances, which include vaginal anatomy (for ease of use and comfortable wearing) and intended period of usage. For instance, the intravaginal monitoring device 551 has an angled cap 511 and has a shorter stem 515 that can only accommodate a small battery 513 (e.g. standard or rechargeable (also in another variant charged by inductive coupling) and is intended for short term usage. The intravaginal monitoring device 553, on the contrary, has a slightly lesser angled cap 521 and has a larger stem 525 that can only accommodate a large battery 523 and is intended for long term usage and better comfort.

The intravaginal monitoring device 555 has an angle adjustable cap 531 and has a larger stem 535 that can only accommodate a large battery 533 and is intended for long term usage and better ease of use. Some of these hermetically sealed intravaginal monitoring devices 551, 553, 555 have the same cap 511, 521, 531 size (with rear mounted stem, for optics assembly) and are designed in sizes and dimensioned to fit comfortably to varieties of vaginal anatomies.

Figure 6:
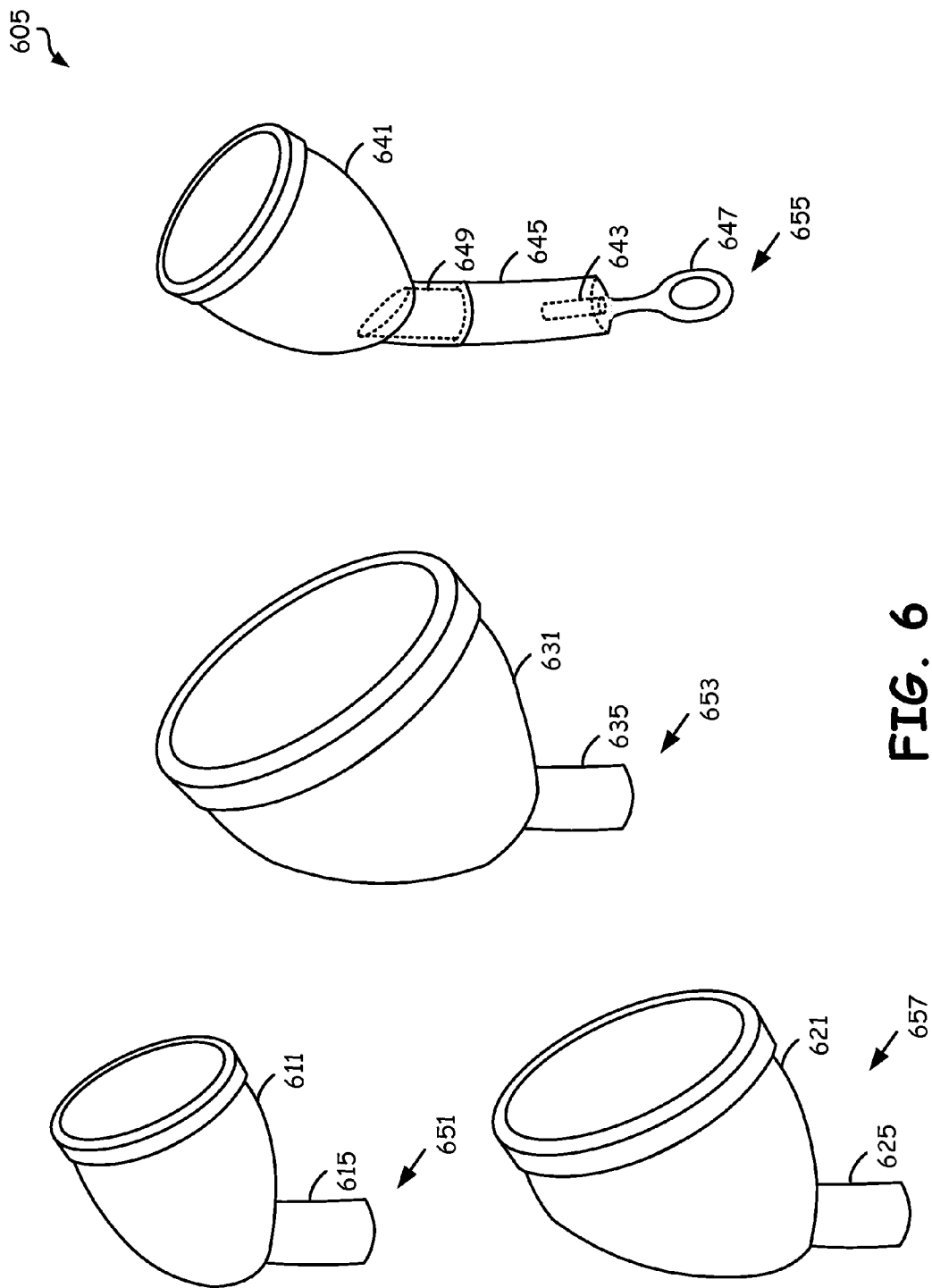
FIG. 6 is a schematic diagram illustrating four different wearable forms of the intravaginal monitoring device of FIG. 1 that are part of a kit, possessing multi-sized caps.

FIG. 6 is a schematic diagram illustrating four different wearable forms of the intravaginal monitoring device 651, 653, 655, 657 of FIG. 1 that are optionally part of a kit, possessing multi-sized caps 611, 631, 641, 621. The illustration shows four different types of wearable intravaginal monitoring devices 651, 653, 655, 657 (that comes in four different cap 611, 631, 641, 621 sizes) that consists of a stem 615, 635, 645, 625 and a finger ring 647 (to be able to insert and remove the intravaginal monitoring device 651, 653, 655, 657— shown only in case of the intravaginal monitoring device 655). The electronics that is part of the intravaginal monitoring device 651, 653, 655, 657 is not shown; nonetheless they are incorporated within the cap 611, 631, 641, 621 and the stem 615, 635, 645, 625.

Each of the three designs of the intravaginal monitoring devices 651, 653, 655, 657 vary slightly (in specific, the cap 611, 631, 641, 621 sizes) and are applicable for different vaginal anatomies, for ease of use and comfortable wearing, and intended period of usage. Each of the hermetically sealed intravaginal monitoring devices 651, 653, 655, 657 is made up of medical grade silicon rubber (or other medical grade plastics) that are adjustable at the neck and the cap 611, 631, 641, 621 itself is flexible so as to fit snugly at the face of outer surface of the cervix. The neck is flexible so that the angle between the cap and the stem flexes and conforms the natural angles between the lower vaginal canal and the upper part of the vaginal canal. It is appreciated that this flexible or pivoting neck contributes to the level of comfort for the female user and also provides for adjustment of the imaging angle between the image capture components of the device and the target cervix or other part of the vagina which is a desired target capture image. The neck can flex through a variety of angles in a planar dimension or can rotate freely across 360 degrees in another variant of the invention.

Figure 7:
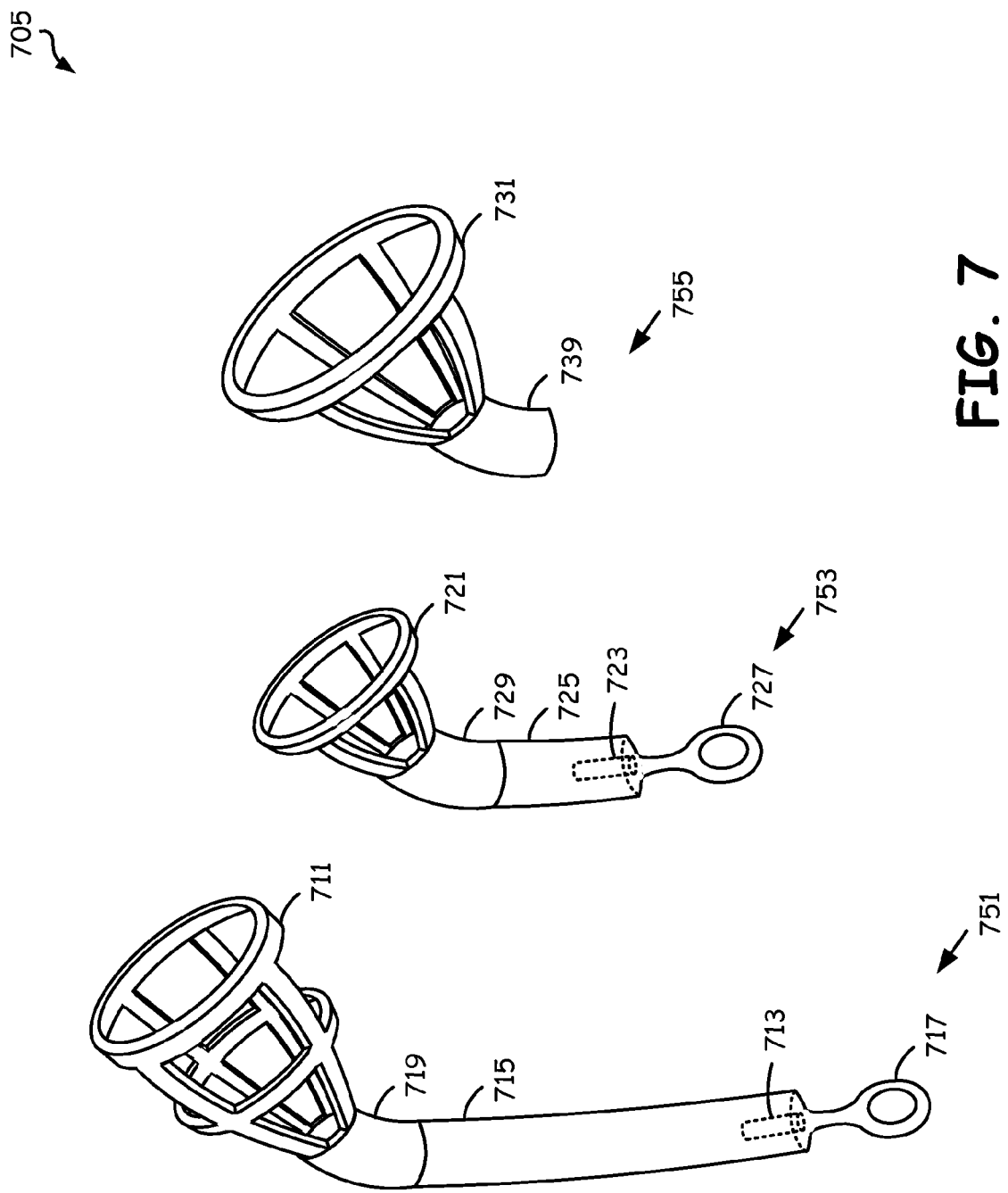
FIG. 7 is a schematic diagram illustrating two different wearable forms of the intravaginal monitoring device of FIG. 1, possessing multi-sized caps and stems; the cap being perforated to allow flow of any vaginal discharges.

FIG. 7 is a schematic diagram illustrating two different wearable forms of the intravaginal monitoring device 751, 753, 755 of FIG. 1, possessing multi-sized caps 711, 721, 731 and stems 715, 725, 735; the cap 711, 721, 731 being perforated to allow flow of any vaginal discharges. Various natural or abnormal vaginal discharges are created by various cells or floral within the vagina, in the cervical canal, or up further in the female anatomy. It is appreciated that detection of discharges assists in the analysis of the health of the female reproductive anatomy. Detection, imaging and sensing of the type of discharge (e.g. color, texture, opacity, consistency, pH, is a feature of the device, and provides a method for determining abnormal pathologies of the female reproductive system).

The illustration shows three different types of wearable intravaginal monitoring devices 751, 753, 755 (which comes in three different perforated cap 711, 721, 731 sizes) that consists of a stem 715, 725, 735 and a finger ring 717, 727 (to be able to insert and remove the intravaginal monitoring device 751, 753, 755—shown only in case of the intravaginal monitoring devices 751, 753). The electronics that is part of the intravaginal monitoring device 751, 753, 755 is not shown in this figure; nonetheless they are incorporated within the cap 711, 721, 731 and the stem 715, 725, 735. As is illustrated, various form factors that permit detection of various intravaginal conditions are used herein.

Each of the three designs of the intravaginal monitoring devices 751, 753, 755 vary slightly (in specific, the cap 711, 721, 731 sizes) and are applicable for various vaginal anatomies, for ease of use and comfortable wearing, and intended period of usage. Each of the optionally hermetically sealed intravaginal monitoring devices 751, 753, 755 is made up of medical grade silicon rubber (or other medical grade plastics, glass, acrylics, biocompatible material, biocompatible carbon coated materials, biocompatible metals, or combinations thereof) that are flexible at the neck 719, 729, 739 and the cap 711, 721, 731 itself is flexible so as to fit snugly at the face of outer surface of the cervix. The cap 711, 721, 731 spreads the vaginal tissue to provide line of sight and perforations (openings) allow fluid flow.

It is further appreciated, that one or more components of the device described herein are reusable and or disposable in one or more combinations. By way of example, caps are disposable. In this variant, replacement disposable caps are provided in cap kits. By way of further example, sheaths are provided for the device that are transparent and or translucent. For example, materials from which condoms are constructed are used for the disposable components of device and system. Use of the kits provides for hygienic conditions to be provided to a user, and to keep various parts of the device free of bodily fluids. A user may simply may insert a sheath over one or more components of the device in the same manner as a condom is placed over a penis. The sheath conforms snugly over one or more components of device and or cap, and is constructed of a very thin elastic, hypoallergenic material. By virtue of the elasticity of the material, a watertight or water proof seal with made between the elastic covering and the device. The device is used, the sheath removed and discarded. By way of further example, the top portions of the caps described herein, in another variant, include a thin clear plastic film (tensioned or non tensioned) covering the top portion thereof, or open area. This plastic film can come in direct contact with the cervix. When spotting occurs the spotting will be visible on the thin plastic film and imaged by the camera. It is appreciated that these variants of the invention provide both hygienic benefits as well as the benefits of keeping the lens assembly (and indeed where the sleave covers the entire device) free from bodily fluids and microbes. Typical types of materials used include biocompatible shrink wrap material, and other medical grade plastics. Of course, the sheath in different variants covers all of the device, substantially all of the device, part of the device, and the top portion of the sheath or plastic film can have markings thereon (e.g. crosshairs, and other measurement markings such as circumferential measurement markings, quadrant markings, grid pattern markings) so that the imager images both the markings and the markings in relation to the cervix itself. This feature also assists in visually positioning the device in relation to the cervix, e.g. the cross hairs can be positioned over the opening of the cervical canal. Where the film is elastic it can also provide a three dimensional topography of the cervix including contours. It is appreciated that the device of the present invention includes a reusable member and also a kit including one or more disposable members.

Figure 8:
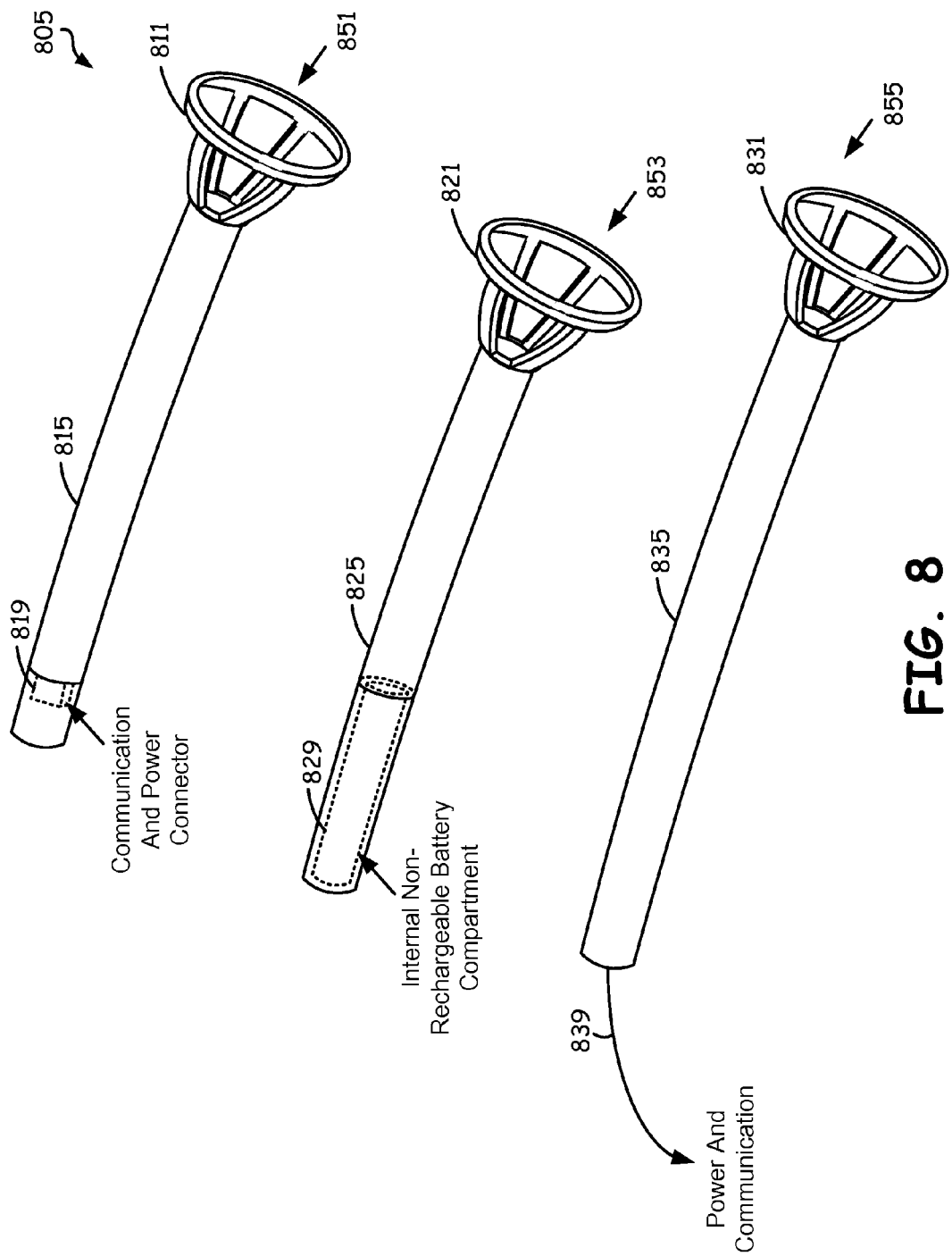
FIG. 8 is a schematic diagram illustrating powering and electronic communication schemes of the intravaginal monitoring device of FIG. 1.

FIG. 8 is a schematic diagram illustrating powering and electronic communication schemes of the intravaginal monitoring device 851, 853, 855 of FIG. 1. Specifically, the illustration shows three different types of intravaginal monitoring devices 851, 853, 855 that consist of a stem 815, 825, 835. For illustration purposes, three non-wearable intravaginal monitoring devices 851, 853, 855 with perforated caps 811, 821, 831 of same sizes are shown here. The electronics that is part of the intravaginal monitoring device 851, 853, 855 is not shown in this figure; nonetheless they are incorporated within the cap 811, 821, 831 and the stem 815, 825, 835. Instead, only powering and communication schemes and structures 819, 829, 839 are shown. As described above, an optional flexible, plastic film is heat sealed around the rim of the caps 811, 821, 831.

The illustration of the intravaginal monitoring device 851 shows wired power for charging as well as communication via a connector (for instance, mini-USB; shown here in non-wearable configuration, but can be wearable if hermetically sealed). The illustration of the intravaginal monitoring device 853 shows a non-rechargeable battery powering scheme for charging; and wireless communication scheme (not shown in this figure). The intravaginal monitoring device 853 can be a wearable type or non-wearable type in this variant. The illustration of the intravaginal monitoring device 855 shows a non-wearable tethered shape with DC power and communication that is accomplished through the same cable (similar to a typical USB or mini USB cable of a digital camera, mobile phone).

Figure 9:
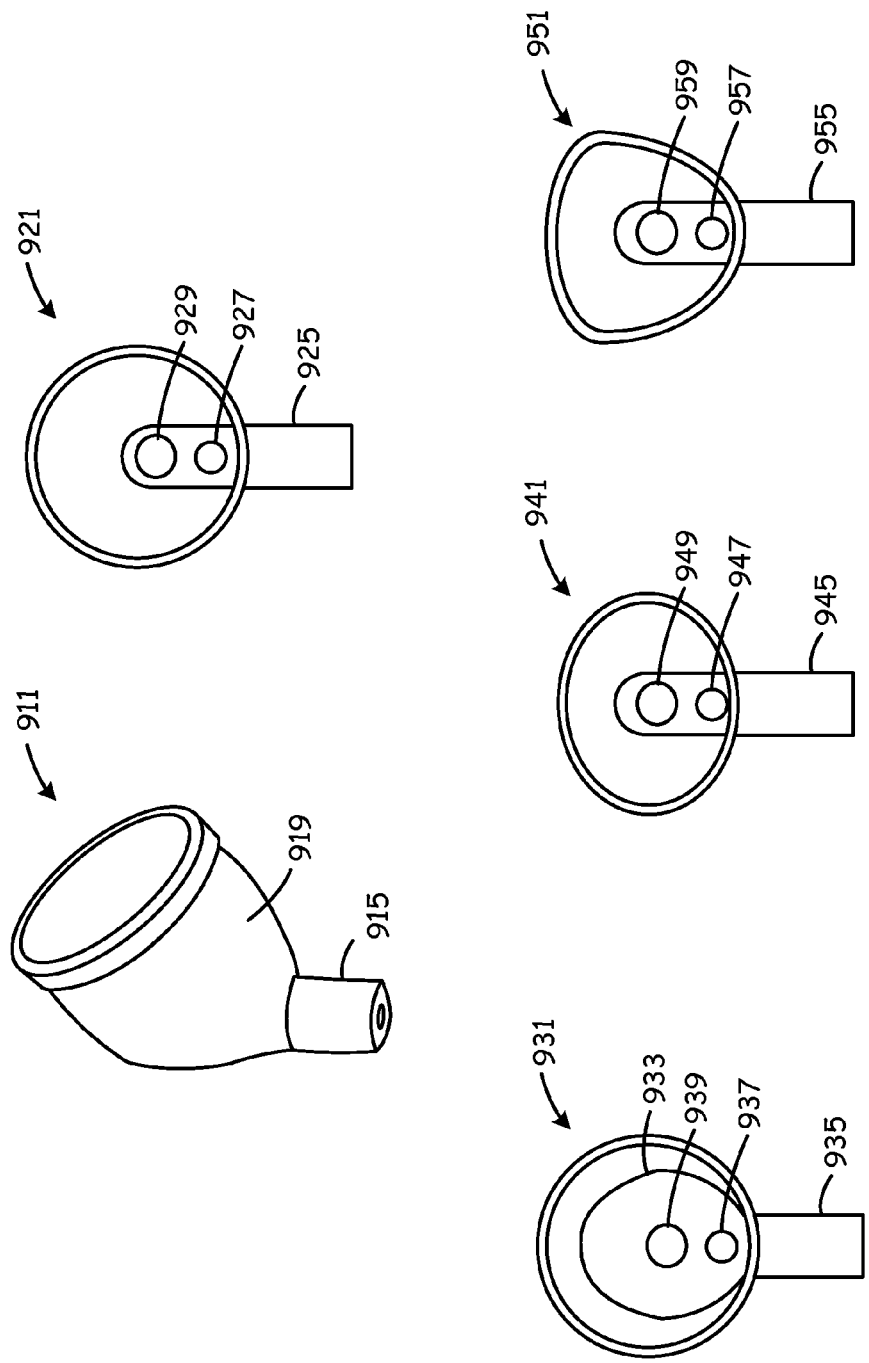
FIG. 9 is a schematic diagram illustrating hermetically sealed cap or head of the intravaginal monitoring device of FIG. 1; wherein the illustration also depicts the placement of camera and a flash light within the center of the hermetically sealed transparent cap or head.

FIG. 9 is a schematic diagram illustrating hermetically sealed cap or head 919 of the intravaginal monitoring device 911, 921, 931, 941, 951 of FIG. 1, as one variant; wherein the illustration also depicts the placement of camera 929, 939, 949, 959 and a light source 927, 937, 947, 957 within the center of the hermetically sealed transparent cap or head 919. The illustration 911 shows cervical or diaphragm sized cap 919 with minimal stem 915 lengths. The corresponding illustration 921, in a first embodiment, shows a front end view, which has very little electronic components inside cap area except light source 927 and central lensing/optics assembly 929. Rest of the electronics is placed within the stem area 925. A variety of light sources 927 are employed in variants of the invention. Light source 927 also includes one or more light emitting diode light sources in one variant, alone or in combination with other light sources. The light sources 927 (including LEDs) can be placed in various locations on the device of the invention to provide visible light and or light in different ranges of the electromagnetic spectrum, e.g. UV, infrared, visable, etc. Where UV light is emitted by the light source, an antimicrobial effect is also provided in the vaginal cavity, as a therapy or to modulate normal or abnormal intravaginal flora. Light source 927 (one or more) illuminates one or more sides or three dimensional contours of the cervical anatomy to provide for optimal imaging conditions. It is appreciated that light source 927 is a cool light source emitting zero or minimal thermal energy in a variant. As such, an accurate temperature within the vaginal cavity is sensed, unaffected by the thermal effects of the light source. Moreover, a user does not feel the thermal energy emitted by the light source. Where a light source is used that does emit thermal energy, the device has functionality to determine the thermal temperature increase due to the light source and functionality to compensate for this effect as regards the internally measurable temperature within the vagina.

The illustration 931, in a second embodiment, shows a front end view, with most of the electronics inside the cap area 933, including light source 937 and central lensing/optics assembly 939. The remaining components of the electronics are placed within the stem area 935. Two embodiments of 941 and 951 are similar to those shown in illustration 921, except that the caps are shaped differently. In other words, in this variant very few electronic components are located inside cap area except light source 947, 957 and central lensing/optics assembly 949, 959. The remaining electronics are placed within the stem area 945, 955.

Figure 10:
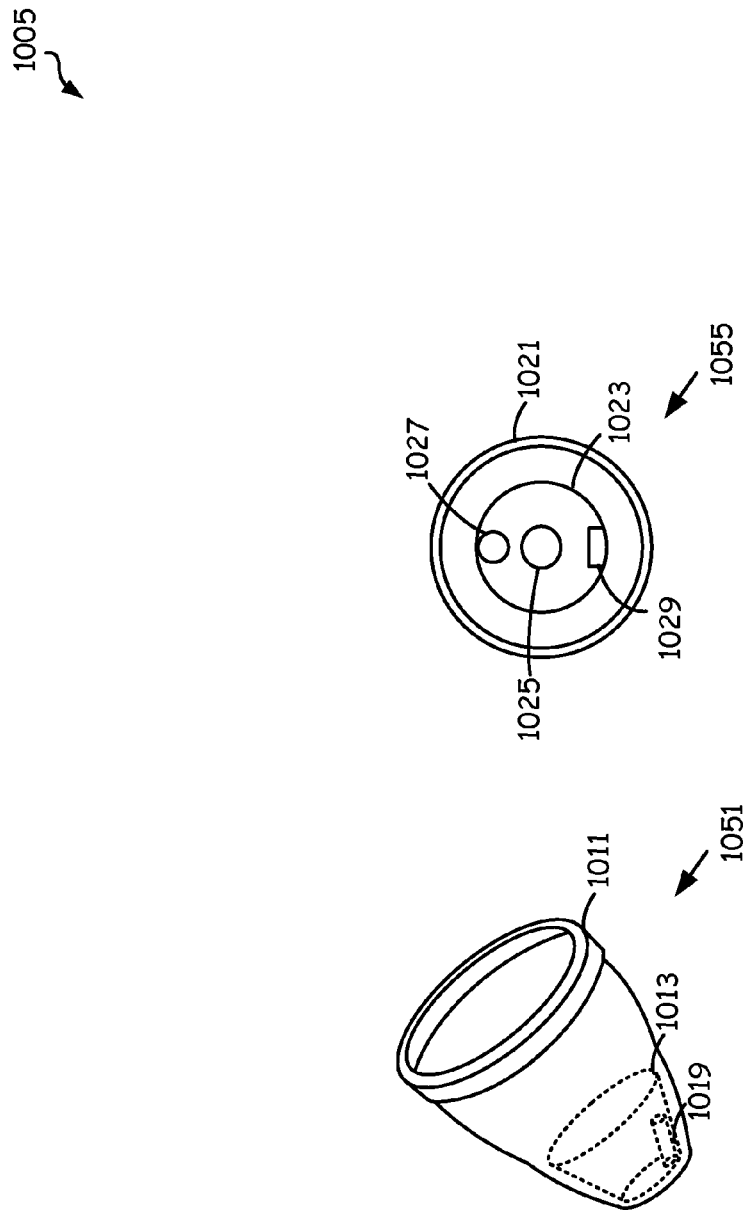
FIG. 10 is a schematic diagram illustrating hermetically sealed cap or head of the intravaginal monitoring device of FIG. 1 that contains all of the electronics and battery; wherein the illustration also depicts an infrared thermometer placed at the bottom of the hermetically sealed transparent cap or head.

FIG. 10 is a schematic diagram illustrating hermetically sealed cap or head 1011, 1021 of the intravaginal monitoring device 1051, 1055 of FIG. 1 that contains all of the electronics 1013, 1023 and battery 1019, 1029; the illustration also depicts an infrared thermometer 1025, 1027 placed at the bottom of the hermetically sealed transparent cap or head in this variant. The placement of the thermometer or temperature sensor in this form or other form is made at a desirable location on the device, e.g. stem, cap, etc.

Measurement of temperature is indicative of a number of normal and abnormal conditions or events within the vagina. For example, in the event of an intravaginal infection an increase in normal intravaginal temperature is detected with the device. The initial temperature increase can be localized to where the infection is, prior to the time that gross systemic temperature changes arise. It is appreciated that the device provides early detection of infection.

Similarly, where the device has functionality to serve as a ovulation detector, the device senses a rise in temperature indicating a female is ovulating. A baseline temperature reading is made by the device and compared to a standard temperature or a normal non ovulation period of time temperature of the female and an alert is sent from the device to a remote device. The device provides accurate alerts to the female, the female's sex partner, or other person, indicating a fertility window has opened. This permits an optimal methodology and time period or window of opportunity for impregnating the female, e.g. either by natural means or artificial insemination procedures, as well as determining an optimal time window for harvesting eggs. Similarly, the temperature data is correlated with imageable changes on the cervix, e.g. sheen or shine due to release or hormones and proteins or other normal fluids (or formation of microcrystalline structures), during a fertility period. The device or external device through an analysis of one or more aspects of the data inputs determines that a fertility window has been reached, monitors the fertility window, and can also detect the close of the fertility window. This is accomplished by analyzing data harvested and measured by the device by one or more sensors, e.g. imageable data, temperature data, etc., and comparing this data with data harvested during a non fertile period of time or event or baseline non fertile period. It is appreciated that the device provides ovulation prediction functionality, fertility window prediction functionality and a method for accomplishing same. Alerts are provided on remote devices based upon data harvested from the device. For example, for a male and female who desire to have a conception event, the device is used in the female, harvests data, makes a determine regarding a fertility window, and communicates an alert to a remote smart phone or the male (providing a message to come to the female and engage in coitus and an impregnation), an alert to the female of the fertility window, and or an alert to a fertility professional that an implantation window is opening for a treatment or other appropriate procedure that will result in implantation. In vitro fertilization process data is correlated with data harvested by sensors on the device in another variant.

In yet another variant, the device and method herein provides for a device that harvests data, processes it, and then provides an alert or notification of a non fertile window of a female. In other words the device, enables an automated form of the rhythm method of birth control. The data harvest and analysis provides an identification of a period of non fertility of the female. Notifications and alerts are sent to remote devices identifying periods of infertility of the female where coitus can be engaged in with no or little risk of conception even where the male ejaculates in the females vagina.

In another variant, the device provides a pregnancy test device and method. By way of example, a pre-pregnancy image of cervix is harvested. Pre-conception, the cervix has a light pink hue readily observable by the imager of the present invention. Post conception, the cervix changes color. For example, the cervix may develop a deeper purple hue due to a change in the females hormone levels. The device and method harvest the image of the cervix post conception. A comparison is made by the device and or method of an image preconception and post conception, and a determination is made if the woman is pregnant or not pregnant, e.g. color change image comparison. In another variant, an image is simply made post conception and based upon a database of colors associated with pregnancy or non pregnancy conditions a determination is made with respect to the female's pregnancy state. Similarly, the device and method is used to continually monitor the pregnant female and determine is she is holding the fetus in her womb or whether a spontaneous abortion of miscarriage is occurring or has occurred. Both before and after any of these events images are harvested by the device and method and compared to other images to determine whether an event has occurred.

In another variant, the device and method herein provide a historical timeline of events for which the device harvests data. For example, there is date and time correlation between image data and sensor data. Events are displayed in an easy to read histogram format to tell the story of the events for a particular female, for a group of females, etc. A Graphic User Interface (GUI) is provided in one variant providing this information and openening up windows of detail regarding clinically relevant or significant events, while discarding those events and time periods that have no clinical significance. Displays of clinically relevant parameters are provided which include graphs, histograms, time vs. clinical parameter sensed with sensors on the device, and the like.

The illustration 1051 shows side view of the cervical or diaphragm sized cap 1011, while the illustration 1055 shows front end view. The hermetically sealed cap, in this embodiment, contains all of the electronics inside cap area 1013, 1023 (including light source 1027, central lensing/optics assembly 1029 and battery 1019, 1029. All of these electronic components, that in addition include some other sensors (not shown in this figure), are placed within the hermetically sealed transparent silicon rubber, or other plastic, covering the cavity. It is appreciated that this and all other caps used herein are self expanding and or self conforming to the tissues of vaginal anatomy while providing a field of view of the target cervical region in one variant of the invention.

Figure 11:
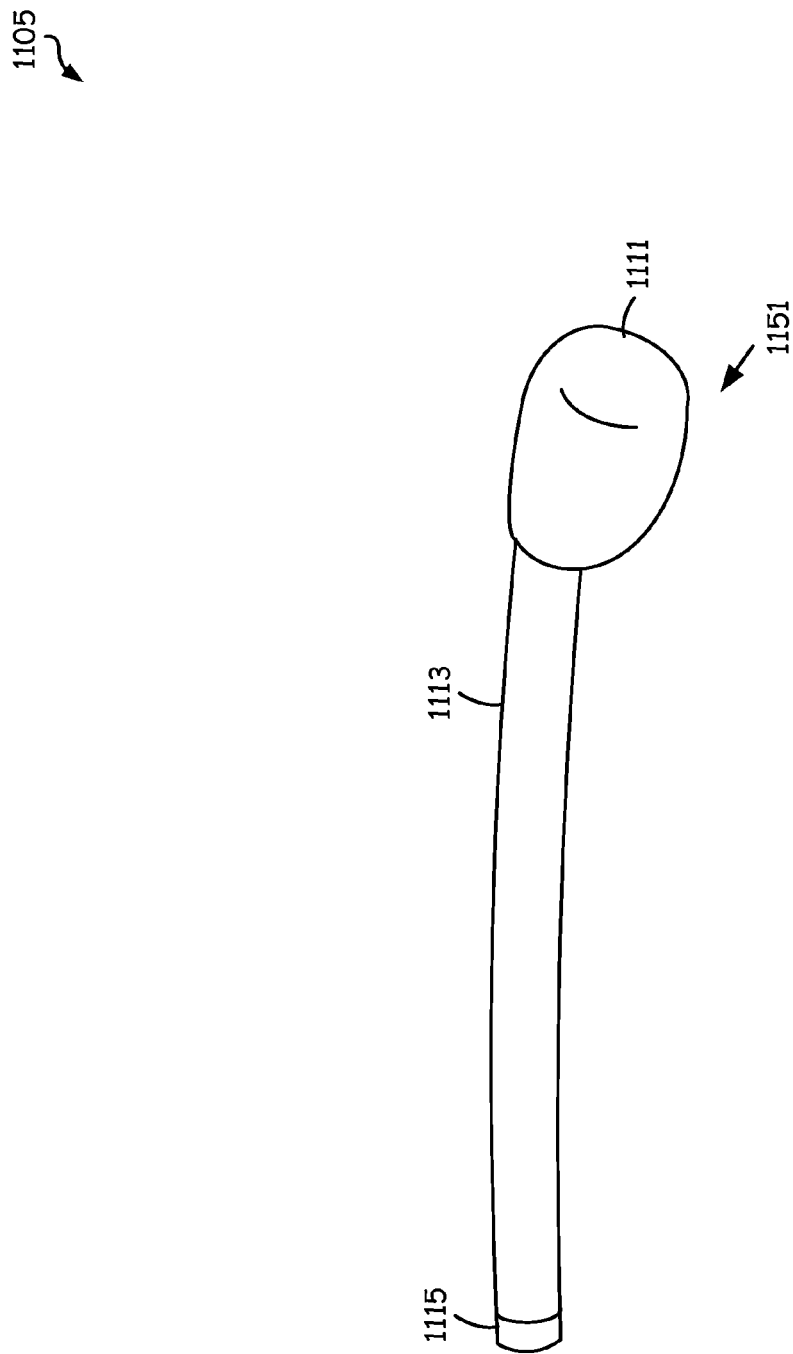
FIG. 11 is a schematic diagram illustrating hermetically sealed intravaginal monitoring device of FIG. 1; wherein a head and stem contain some or all of the electronics related to the intravaginal monitoring device.

FIG. 11 is a schematic diagram illustrating hermetically sealed intravaginal monitoring device of FIG. 1; wherein a head and stem contain some or all of the electronics related to the intravaginal monitoring device. The illustration, in specific, shows a different type of non-wearable intravaginal monitoring device 1151 (nonetheless, it can be wearable or non-wearable, and can be used over a short period or long period of time) that consists of a bulb shaped head 1111, stem 1113 and a screw end 1115 (to be able to insert and remove batteries or for communication purposes). The electronics that is part of the intravaginal monitoring device 1151 is not shown; nonetheless they are incorporated within the head 1111 and the stem 1113. As described in different variants herein, a plastic or elastic plastic sleeve can enclose all or part of the device 1151 and provide the benefits and functionality described herein.

The entire intravaginal monitoring device 1151 may be a single piece of blown glass (e.g. pyrex or other suitable glass material) or molded plastic with a hermetically sealed head 1111. In one variant, an acrylic material is used. Note that the intravaginal monitoring device 1151 is not cap shaped at all and glass/plastic end just sits in area immediate in front of outer surface of the cervix (to spread tissue) and can even touch cervix. In another variant of the invention, features described above in the capped variant are combined with the features described in this paragraph. A lensing assembly is built in directly into the molded plastic and or formed therefrom in one variant. In another variant, a "fish eye" lense or a panoramic lens assembly to provide a full view of the target area, e.g. the cervical field of view. The lens assembly can also be a zoom lens, fixed focal length lenses, adjustable focal length lenses, and self adjusting or focusing lenses in different variants.

The stem of this and other variants can also be curved to conform the natural anatomy of vagina. The head of this variant of the device is bulbous in shape so as to be readily inserted and withdrawn. The head or cap is also egg shaped or asymmetric in variants of the invention. It is also understood that the head is shaped in a non-traumatic so that when it is used in the pre-birth time period, a premature exit of the fetus from the womb, and contact of the fetus with the device, does not injure the fetus. In other variants, a variety of dimensioned caps or removable heads for the device are provided to accommodate the dimensions of the vagina during different trimesters of pregnancy or different time periods in a woman's life.

Numerous dimensions of the device are used herein in different variants, but of course any dimensions can be used, alone or in combination. Diameters of the stem of the device are in the range of about 0.5 cm to about 3.0 cm. The bulbous head itself can be symmetrical or asymetrical in shape, with a dimension in the range of about 1.5 cm to about 4 cm, by way of example. The stem in relation to the neck can be angled in the range of 5 degrees to 45 degrees to the bulbous head by way of further example.

Figure 12:
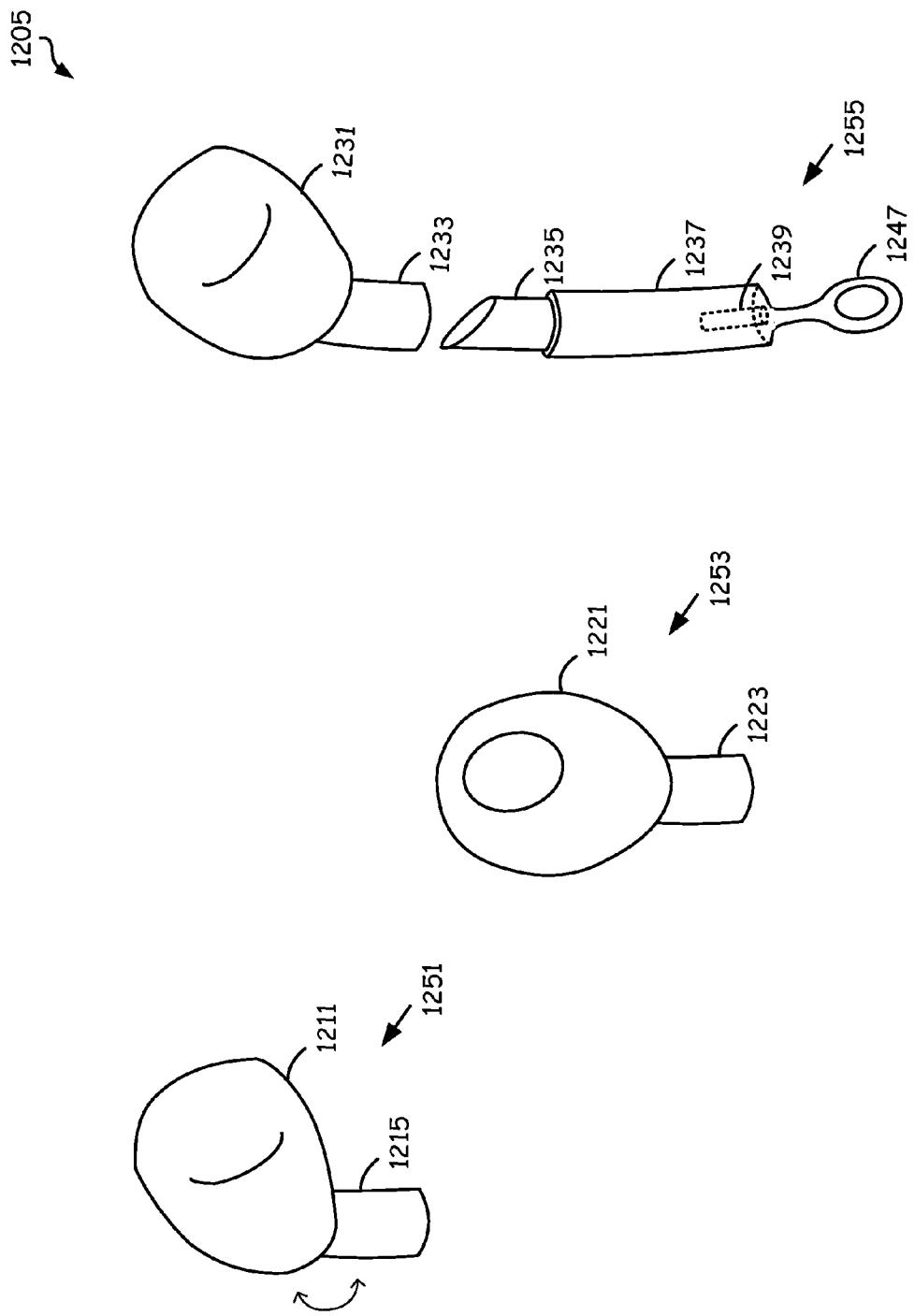
FIG. 12 is a schematic diagram illustrating hermetically sealed intravaginal monitoring device of FIG. 1; wherein the illustration also depicts many different flexible and adjustable forms a head and stem.

FIG. 12 is a schematic diagram illustrating hermetically sealed intravaginal monitoring device 1251, 1253, 1255 of FIG. 1; wherein the illustration also depicts many different flexible and adjustable forms a head 1211, 1221, 1231 and stem 1215, 1223, 1237. The illustrations 1251, 1253, 1255 show wearable or non-wearable hermetically sealed intravaginal monitoring device 1251, 1253, 1255 that has a transparent head 1211, 1221, 1231 and transparent silicon rubber at the neck (where the stem 1215, 1223, 1237 meets the head 1211, 1221, 1231) could be designed to easily bend or be flexible. In one variant of the invention, the neck in relation to stem is self conforming to the vaginal anatomy as a result of flexion of the neck and the stem in relation to the head. In yet a further variant, the entire device is fully conformation and flexible, and can take on any form. There is an optional locking means for locking the device into a set conformation. Body structures which provide flexibility such as structures used in "Snake" light types made from biocompatible materials are used herein in one variant. Alternately, only the stem portion is constructed to be conformational while the head is rigid in one variant.

A design looking like a right side up or upside down egg centered symmetrically on a stem 1215, 1223, 1237 offers a more pleasing and easily insertable design. The intravaginal monitoring device 1253 depicts a head 1221 is shaped like an egg with a slice removed (or not removed, in an embodiment). The flat oval formed by the missing slice accommodates the viewing angle of the optics assembly (not shown). The intravaginal monitoring device 1255 depicts transparent silicon rubber at the neck 1233 that easily bends while inserting, and also is removable (at 1235) so that the stem 1237 containing battery 1239 and some other electronic components can be used to transfer images and data to another video system for monitoring. The illustration 1255 also shows a finger ring 1247 (to be able to insert and remove the intravaginal monitoring device 1251, 1253, 1255—shown only in case of the intravaginal monitoring devices 1255).

Figure 13:
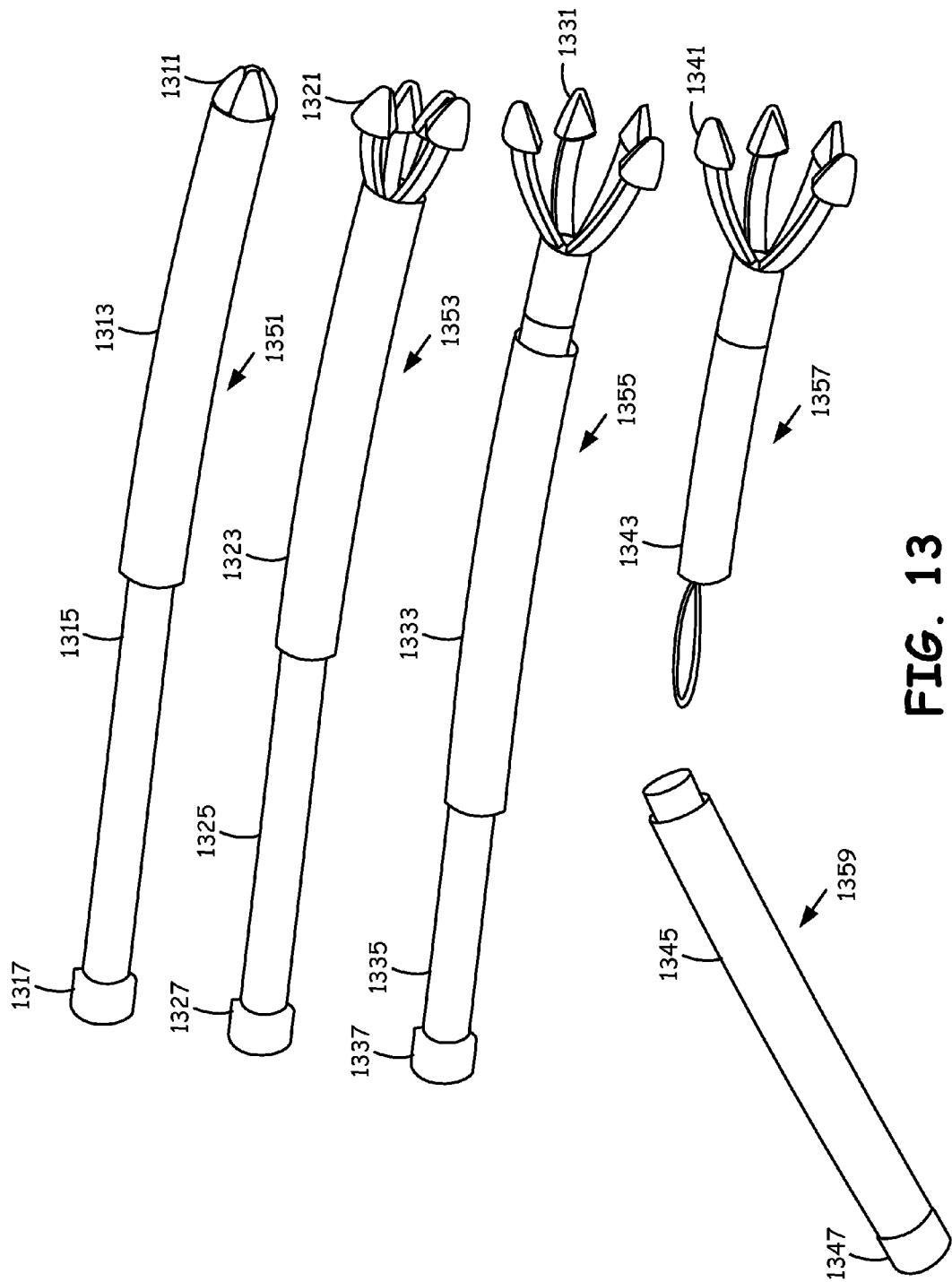
FIG. 13 is a schematic diagram illustrating hermetically sealed intravaginal monitoring device of FIG. 1; wherein the illustration depicts a flexible cap that opens up upon proper placement of intravaginal monitoring device and then pushing the bottom half of the stem.

FIG. 13 is a schematic diagram illustrating hermetically sealed intravaginal monitoring device 1351, 1353, 1355, 1357 of FIG. 1; wherein the illustration depicts a flexible cap 1311, 1321, 1331, 1341 that opens up upon proper placement of intravaginal monitoring device 1351, 1353, 1355, 1357 and then pushing the bottom half of the stem 1315, 1325, 1335, 1345.

Specifically, the illustration shows wearable intravaginal monitoring device 1351, 1353, 1355, 1357 that provides the female an expanding cap (that expands only after insertion; somewhat like tampon insertion—something wearers would be familiar and comfortable with). In one variant, the cap is self expanding and/or baised outward to expand and move the tissue of the vagina out to expose the cervix for imaging. The different wearable intravaginal monitoring device 1351, 1353, 1355, 1357 contains a stem 1313, 1323, 1333, 1343 and finger ring 1349 (to be able to insert and remove the intravaginal monitoring device 1351, 1353, 1355, 1357—shown only in case of the illustration 1357, upon proper placement). In addition to or in place of the finger ring a string or looped string is provided to assist in removal of the device from the vagina. The string is constructed of a biocompatible material that is microbe resistant. The electronics that is part of the intravaginal monitoring device 1351, 1353, 1355, 1357 is not shown; nonetheless they are incorporated within the cap 1311, 1321, 1331, 1341 and the stem 1315, 1325, 1335, 1345.

In yet another variant of the invention the body of the devices described herein are constructed of a material that kills microbes upon surface contact. Alternatively, a lubricant or gel that contains microbe killing properties is used with the device described herein. The lubricant or gel assists woman who do not have adequate moisture in their vaginas to properly and comfortably insert the device.

This particular design of the intravaginal monitoring device 1351, 1353, 1355, 1357 employs a telescopic bottom half of the stem 1315, 1325, 1335, 1345 (that is hermetically sealed by screwing up the bottom cap 1317, 1327, 1337, 1347), so that the entire intravaginal monitoring device, as depicted in 1351, appears to be sized and dimensioned like a tampon. Upon insertion, as shown in illustrations 1353, 1355, 1357, the intravaginal monitoring device 1351, 1353, 1355, 1357 opens up to provide line of sight view of the outer surface of the cervix, to the camera which is built in the device. Then, as depicted in the illustration 1357, 1359 the bottom half of the stem 1315, 1325, 1335, 1345 is removed and kept in a safe place. The intravaginal monitoring device 1351, 1353, 1355, 1357 then can be used for short term or long period of time, depending upon the needs. Moreover, other mechanical expansion schemes may also be employed, for instance, a spring release cap, screw out cap and so forth. The intravaginal monitoring device 1351, 1353, 1355, 1357 can also be non-wearable and usually is made up of medical grade silicon rubber.

Figure 14:
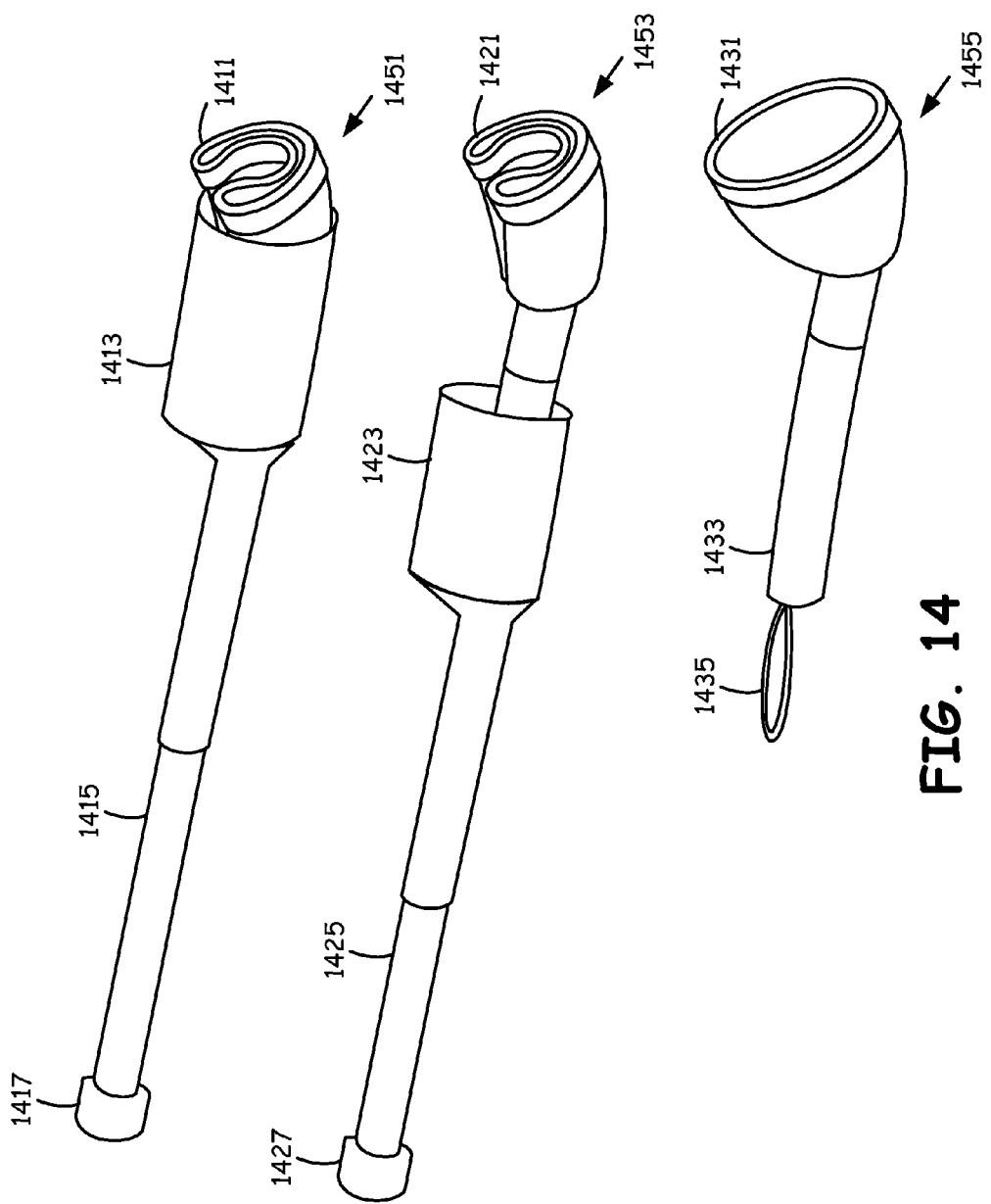
FIG. 14 is a schematic diagram illustrating hermetically sealed intravaginal monitoring device of FIG. 1; wherein the illustration depicts a flexible cap that opens up upon proper placement of intravaginal monitoring device and then pushing the bottom half of the stem, which is another variation of the intravaginal monitoring device of FIG. 13.

FIG. 14 is a schematic diagram illustrating hermetically sealed intravaginal monitoring device 1451, 1453, 1455 of FIG. 1; wherein the illustration depicts a flexible cap 1413, 1423, 1431 that self-opens upon proper placement of intravaginal monitoring device 1451, 1453, 1455 and then pushing the bottom half of the stem 1415, 1425, which is another variation of the intravaginal monitoring device of FIG. 13. The illustration shows wearable intravaginal monitoring device 1451, 1453, 1455 that provides the female a folding 1411, 1421 within the cap 1413, 1423, 1431 (that expands only after insertion). The wearable (that can also be a non-wearable) intravaginal monitoring device 1451, 1453, 1455 illustrations also show a telescopic stem 1415, 1425 and a finger ring 1435 (to be able to insert and remove the intravaginal monitoring device 1451, 1453, 1455—shown only in case of the illustration 1455, that detaches upon proper placement). The electronics that is part of the intravaginal monitoring device 1451, 1453, 1455 is not shown; nonetheless they are incorporated within the cap 1413, 1423 and the stem 1415, 1425.

In one variant of the invention, the stem is totally within the female body. It is appreciated that in this configuration, there is little risk of accidental displacement of the device so that is presses unintentionally up and into a woman's body in an abnormal fashion. Moreover, when totally within the vaginal cavity, it is not noticeable that the user is using the device and that the device is harvesting data. In yet another variant, the device is sized and dimensioned to be wholly contained, enclosed, or hidden within the vaginal cavity so that the outside world does not know the device is within the user. Of course, in a variant, a string may hang outside the vagina to remind the user that the device is still inserted.

This design of the current illustration of the intravaginal monitoring device 1451, 1453, 1455 uses a telescopic bottom half of the stem 1415, 1425 (that is hermetically sealed by screwing up the bottom cap 1417, 1427), so that the entire intravaginal monitoring device, as depicted in 1451, appears like a tampon. Upon insertion, the intravaginal monitoring device 1451, 1453, 1455 opens up to provide line of sight view of the outer surface of the cervix, to the camera built in. The intravaginal monitoring device 1451, 1453, 1455 then can be used for short term or long period of time, depending upon the needs. Moreover, other expansion schemes may also be employed, for instance, a spring release cap, screw out cap and so forth. Moreover, although not shown in the figures, note that the bulb, cage or any other type folding for placement within the insertion housing may also be employed. The intravaginal monitoring device 1451, 1453, 1455 can also be non-wearable and usually is made up of medical grade silicon rubber.

Figure 15:
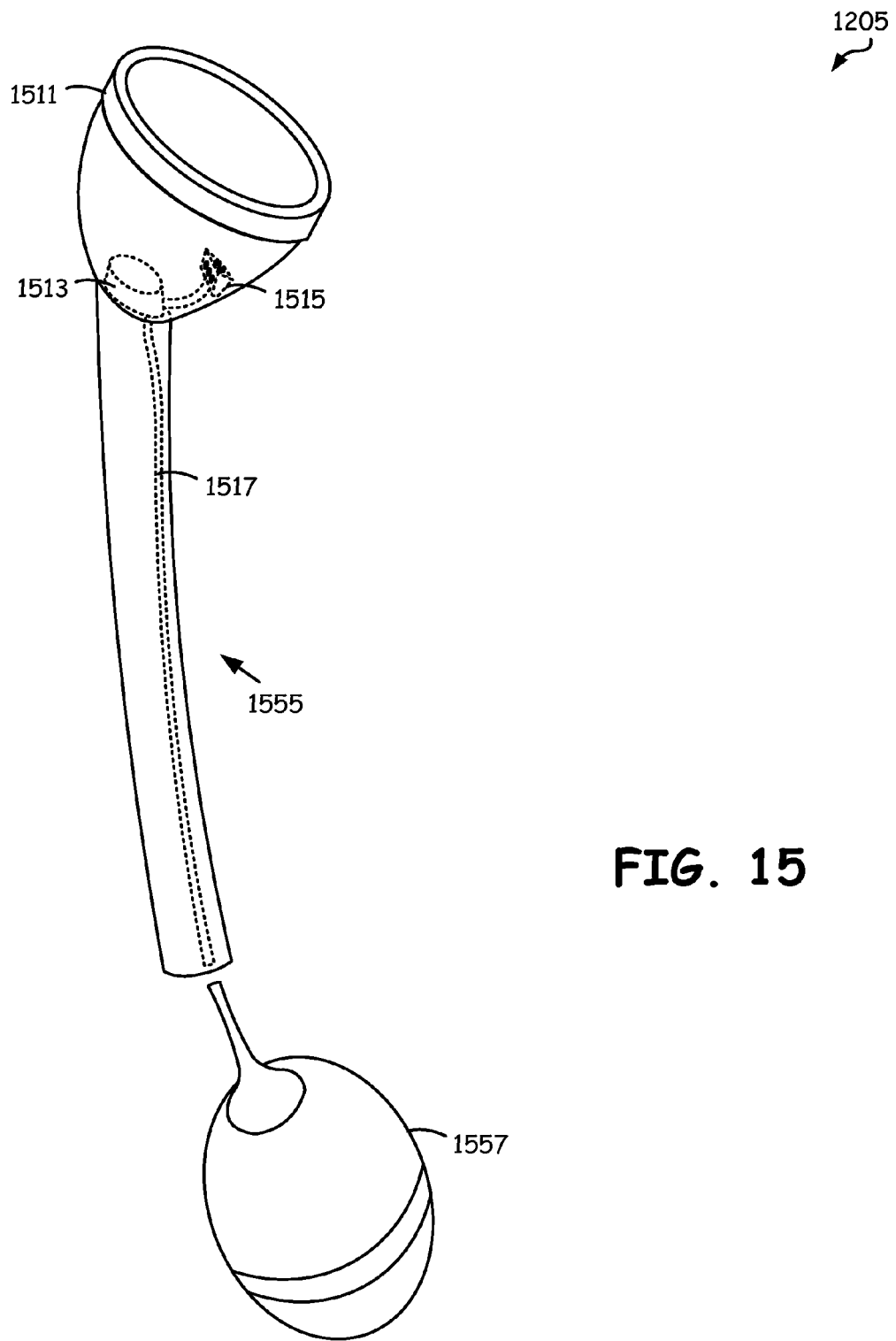
FIG. 15 is a schematic diagram illustrating hermetically sealed intravaginal monitoring device of FIG. 1; wherein the illustration also depicts a fluid flush cleaner on the surface of the cap, that cleans both the surface of the cap and the target area.

FIG. 15 is a schematic diagram illustrating hermetically sealed intravaginal monitoring device 1555 of FIG. 1; wherein the illustration also depicts a fluid flush cleaner 1515 on the surface of the cap 1511 that cleans both the surface of the cap 1513 and the target area. In specific, the illustration shows a non-wearable configuration of hermetically sealed intravaginal monitoring device 1555 (that, in practice, can also be wearable one), which contains a pipe or tube 1517 that extends from the bottom end of the stem till the cap 1511 (above the surface of the hermetically sealed electronic and camera compartment 1513), where there are multiple openings (nozzles 1515) to the tube or pipe, directed toward the surface of the cap 1513 and the target area. In other words, the non-wearable configuration illustrated 1555 shows the tube or thin pipe 1517 internal to the stem; without needing an external tube and the nozzles 1515 facing the optics assembly (at the surface 1513) and the target cervix for cleaning both target and camera.

The thin pipe 1517 at the other end is connected to a fluid container 1519, which upon squeezing pushes the liquid inside of it toward the surface of the cap 1513 and the target area. This allows cleaning of the surface of the cap 1513 and the target area, especially so when the intravaginal monitoring device 1555 is used during the periods of vaginal discharges. Although not shown, the cap 1513 may be perforated one to allow free flow of flushed fluids and vaginal discharges. Also note that the flush fluid can also be used during artificial inseminations. In yet other variants, multiple self adhesive films are placed one on another. After each use, one of the layers of film is peeled a way revealing a new clean layer. The device is again inserted, and used.

Figure 16:
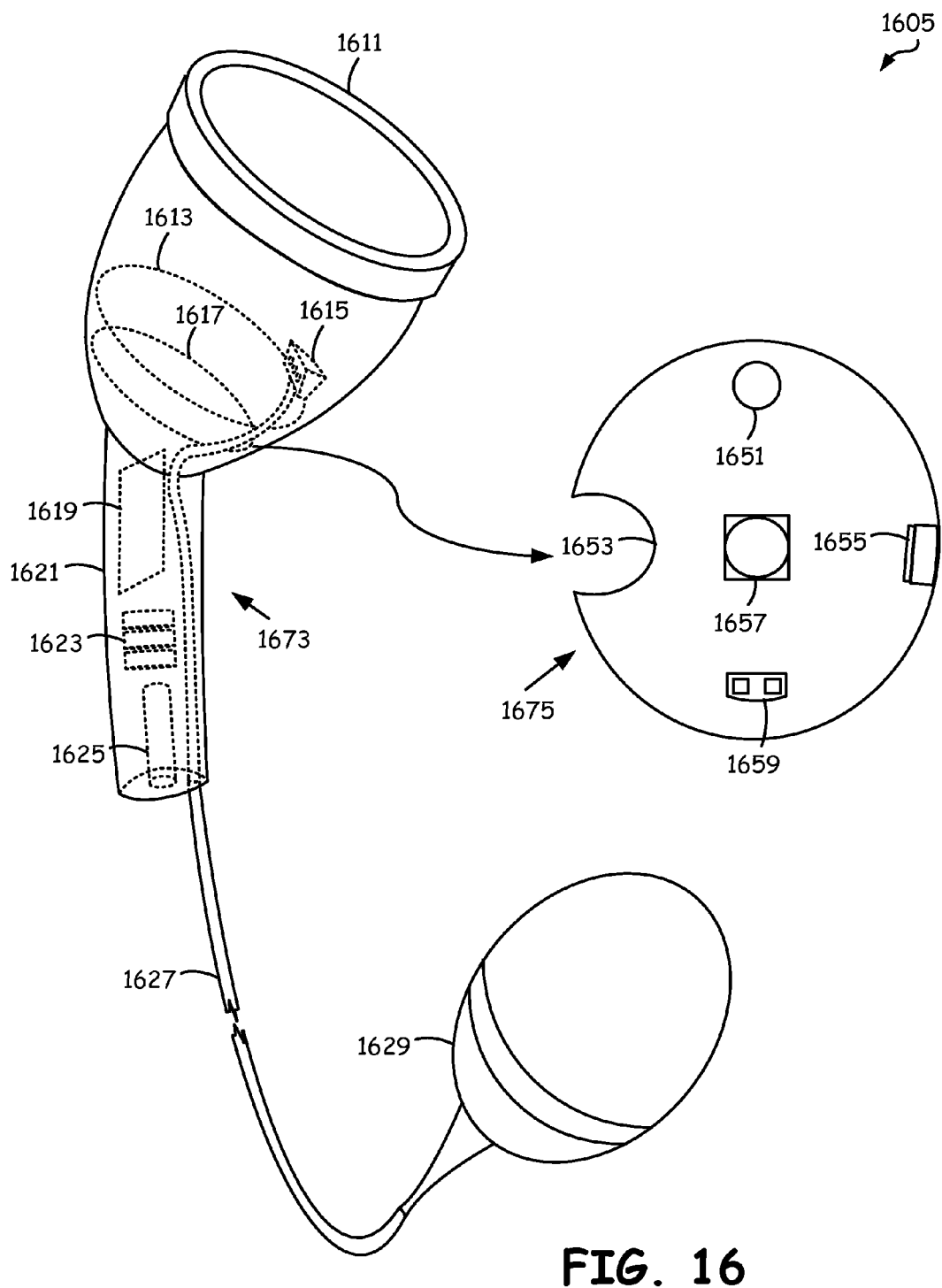
FIG. 16 is a schematic diagram illustrating hermetically sealed intravaginal monitoring device of FIG. 1; wherein the illustration also depicts typical placement of electronic components within the hermetically sealed transparent cap and stem that includes camera, a infrared thermometer and other sensors, processor, memory, communication and user interfaces and batteries, and a fluid flush cleaner on the surface of the cap.

FIG. 16 is a schematic diagram illustrating hermetically sealed intravaginal monitoring device 1673 of FIG. 1; wherein the illustration also depicts typical placement of electronic components 1619, 1623, 1625, 1617 (or, 1675) within the hermetically sealed transparent cap 1611 and stem 1621 that includes camera 1657, 1651, an infrared thermometer 1659 and other sensors such as 1655, processing circuitry and memory 1619, communication 1623 and user interfaces and batteries 1625, and a fluid flush cleaner 1626, 1615 on the surface of the cap 1613. The FIGS. 1 through 15 illustrated physical aspects of the intravaginal monitoring device of FIG. 1, while the current illustration and illustrations furthering from here (till the FIG. 24) describe the electronic aspects.

In specific, the electronic components are placed over two (other variants include more) circuit boards, a primary circuit board 1619 and secondary circuit board 1617 (or, 1675). The electronic components include camera 1657 and illuminator 1651, sensors 1659, 1655, processing circuitry and memory 1619, communication interfaces 1623, user interfaces (shown in FIG. 18) and power management system 1625. The primary circuit board 1619 holds most of the electronic components and secondary circuit board 1617 (or, 1675) only holds those electronic components that are essential for capturing images and taking sensory readings (from the front side of the outer surface of the cervix). Moreover, the secondary circuit board 1617 (or, 1675) may be circular in shape or otherwise shaped to fit in the back of the cap.

The secondary circuit board 1617 (or, 1675), for instance, may only hold light emitting diode illuminator 1651, CCD and lensing assembly/tower 1657; infrared temperature sensor pair 1659, piezo microphone 1655 mounted against a rubber sound conductor (that is, against the cap to gain an increased audible response). Rest of the electronic components (that may include other sensors) may be either placed on the secondary circuit board 1617 (or, 1675) or on the surface of the stem 1621 (as illustrated in FIG. 17).

In one variant, the device also provides additional functionality in addition to diagnostic functionality. By way of example, when the device is in a mode of operation that includes ovulation detection, it can include sperm injection functionality where sperm is injected directly up into the cervical canal or close thereto. In this mode of operation, sperm is injected from a reservoir on the device automatically once a fertility window is detected. By way of further example, the illustration also shows a fluid tube 1627 for lens cleaning or sperm injection. Note that the squeeze rubber bulb/ball 1629 may either be filled with vinegar and water type solutions or other type of female douche or hygiene solutions; alternatively, a syringe containing cleaning solution (or, sperm injection) as well be used. In yet a further variant, agents that assist in diagnosis of an abnormal conditions of the cervix, e.g. per-cancerous changes, such as Acetic acid test agents are used. Similarly, agents such as drugs or therapeutic agents are used also.

In another variant, the device provides for automated drug delivery upon sensing a condition for which drug administration is indicated. The syringe attachment could also be used to deliver drugs or other therapies. Likewise, instead of the exterior tube 1627, cleaning solution/sperm/drug could be stored in interior intravaginal monitoring device 1673 cavity (for instance, within the stem 1621), with an injection grommet for initial delivery and pumping (or a pressurized cavity and valve). In addition, drain holes (when the cleaning system 1629, 1627 and 1615 is not used as a sperm delivery device) can be added to the cap 1611 for cleaning fluid delivery and vaginal-uterus discharges. Also note that the tube 1627 can assist in device insertion-removal.

Figure 17:
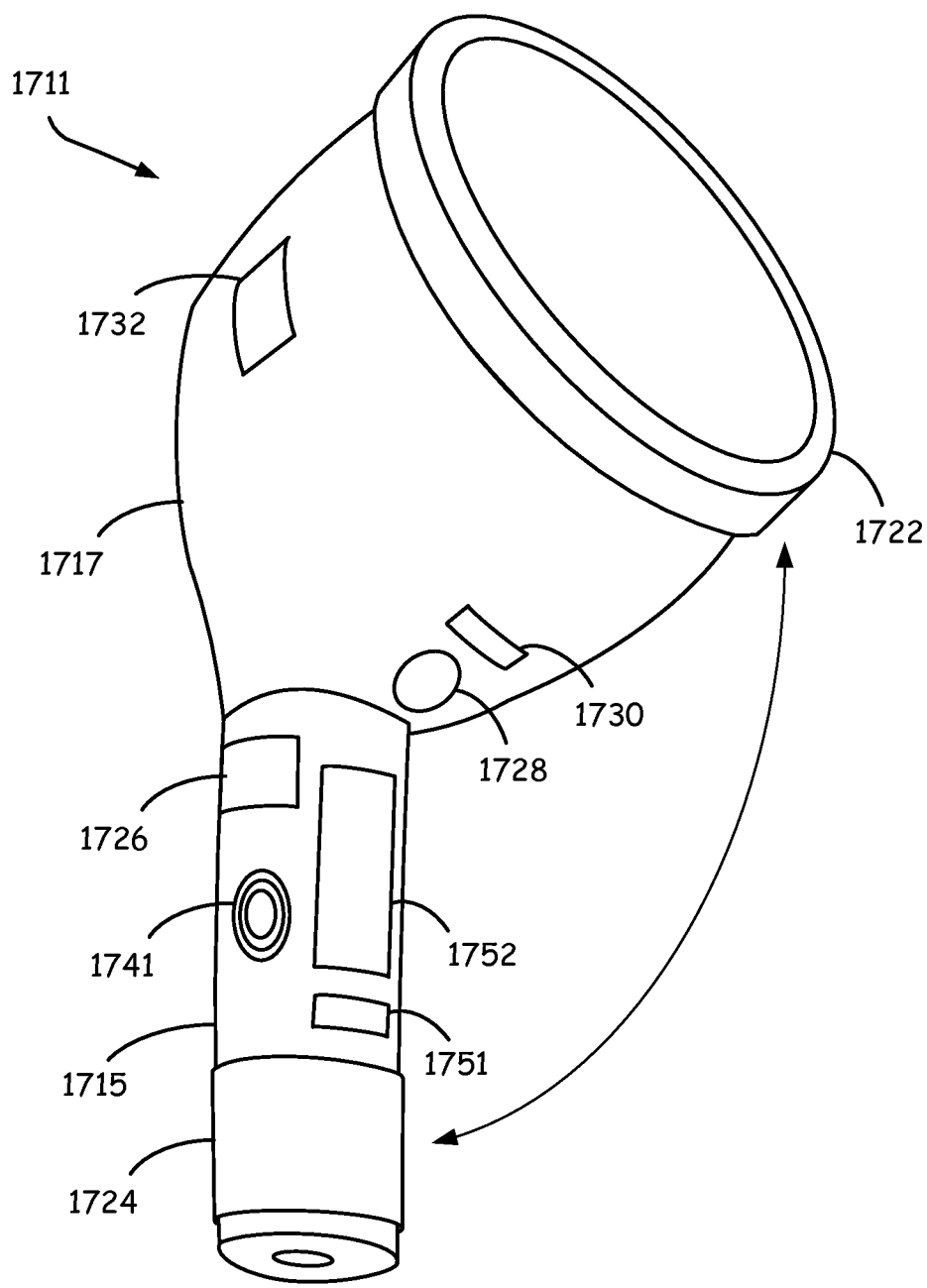
FIG. 17 is a schematic diagram illustrating hermetically sealed intravaginal monitoring device of FIG. 1; wherein the illustration depicts typical placement of electronic sensors on the sides of the hermetically sealed transparent cap and stem that may include sonogram, electrocardiogram, pressure and temperature sensors and user interfaces that includes an on/off switch.

FIG. 17 is a schematic diagram illustrating hermetically sealed intravaginal monitoring device 1711 of FIG. 1; wherein the illustration depicts typical placement of electronic sensors on the sides of the hermetically sealed transparent cap 1717 and stem 1715 that may include sonogram, electrocardiogram, pressure and temperature sensors and user interfaces that include an on/off switch. The illustration shows placement of electronic components, as they appear externally from one side of the intravaginal monitoring device 1711 (while the FIG. 18 shows user interfaces as they appear from another side of the intravaginal monitoring device 1711).

The electronic components that appear from one side of the wearable intravaginal monitoring device 1711 (used for longer term monitoring) include a first conductive ring 1722, second conductive ring (through which electrical potential can be measured, for instance, in case of pregnancy, baby's EKG) 1724, electrolyte, PH, glucose sensors 1726 (these sensors, in reality, may not be co-located), infrared temperature sensor window 1728, plate for thermal temperature sensing 1730, microphone 1732 (for instance, piezo) affixed to either inside or outside of the cap (such that cap amplifies mother-fetus heartbeats or infant movement sounds), hermetically sealed on/off switch with fingertip texture 1741, light emitting display 1751 (for instance, indicating green on ready; red on servicing required—battery, storage full, etc.; no light indicating power off and so forth), and mini-liquid crystal display 1752. Also note that all sensor positions illustrated are merely illustrative; any sensor could be located anywhere on intravaginal monitoring device 1711 housing or there within (if operational).

Figure 18:
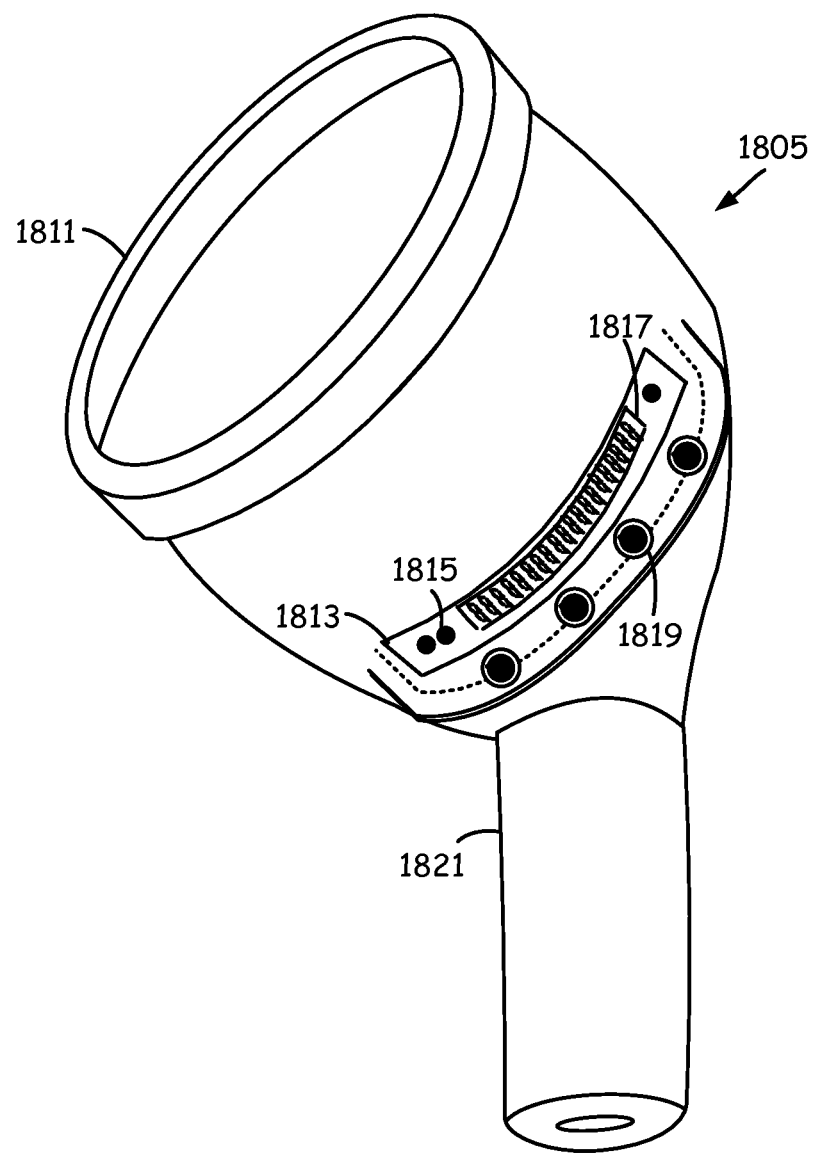
FIG. 18 is a schematic diagram illustrating hermetically sealed intravaginal monitoring device of FIG. 1; wherein the illustration depicts typical placement of user interfaces that includes indicators, speakers, button switches and an electronic display, all of which are placed within the hermetically sealed head or cap, so that they are externally visible.

FIG. 18 is a schematic diagram illustrating hermetically sealed intravaginal monitoring device 1805 of FIG. 1; wherein the illustration depicts typical placement of user interfaces 1813, 1815, 1817, 1819 that include indicators, speakers, button switches and an electronic display, all of which are placed within the hermetically sealed head or cap, so that they are externally visible. In specific the illustration shows placement of electronic components that relates to the user interfaces 1813, 1815, 1817, 1819, as they appear externally from one side of the intravaginal monitoring device 1805. The device includes functionality and electronics for internally within the vagina playing music or audio lessons for the fetus while the fetus is still in the womb. In this aspect, the device provides for stimulation of the fetus while in the womb. In yet another aspect, the fetus movements are detected over a period of time, and recorded on the device to provide additional diagnostic information. It is appreciated that having a digital record of fetal movements is useful to determine normal fetal development or abnormal fetal development and also to act as a diagnostic to determine if the fetus is dead within the womb. The detection of abnormal amount or lack thereof of fetal movements may indicate some problems with the fetus. The device provides a method of determining the health of the fetus within the womb.

In yet another aspect, an EEG sensor is provided on the device to monitor the fetus brain wave activity or lack thereof. This information is correlated with other data from the fetus and the mother. Where the fetus has died in womb, immediate alerts are provided such that appropriate medical procedures can be provided in a timely manner.

Typically, on removal of the hermetically sealed intravaginal monitoring device 1805, the female or a health care professional may wish to know the sample readings as well as to listen to the sounds of heart beat (in case of a baby), without having to have an external display. For instance, heart beat or heart rate data (real time or in graphical form, e.g. heart beat vs. time) of the baby is sampled by a piezo microphone, which may be readily heard by the female or a health care professional by pressing one of the buttons 1819; alternatively, a sample reading of temperature or pressure may be read on the light emitting display or liquid crystal display 1817 by clicking on others of the buttons 1819. These user interfaces are meant for quick assessments of particular conditions alone, without needing any other devices to read out the sample sensory readings, upon short term wearing and harvesting of the data.

All user interface positions illustrated are merely illustrative; user interfaces may be located in many other locations of the intravaginal monitoring device 1711 housing or there within.

Figure 19:
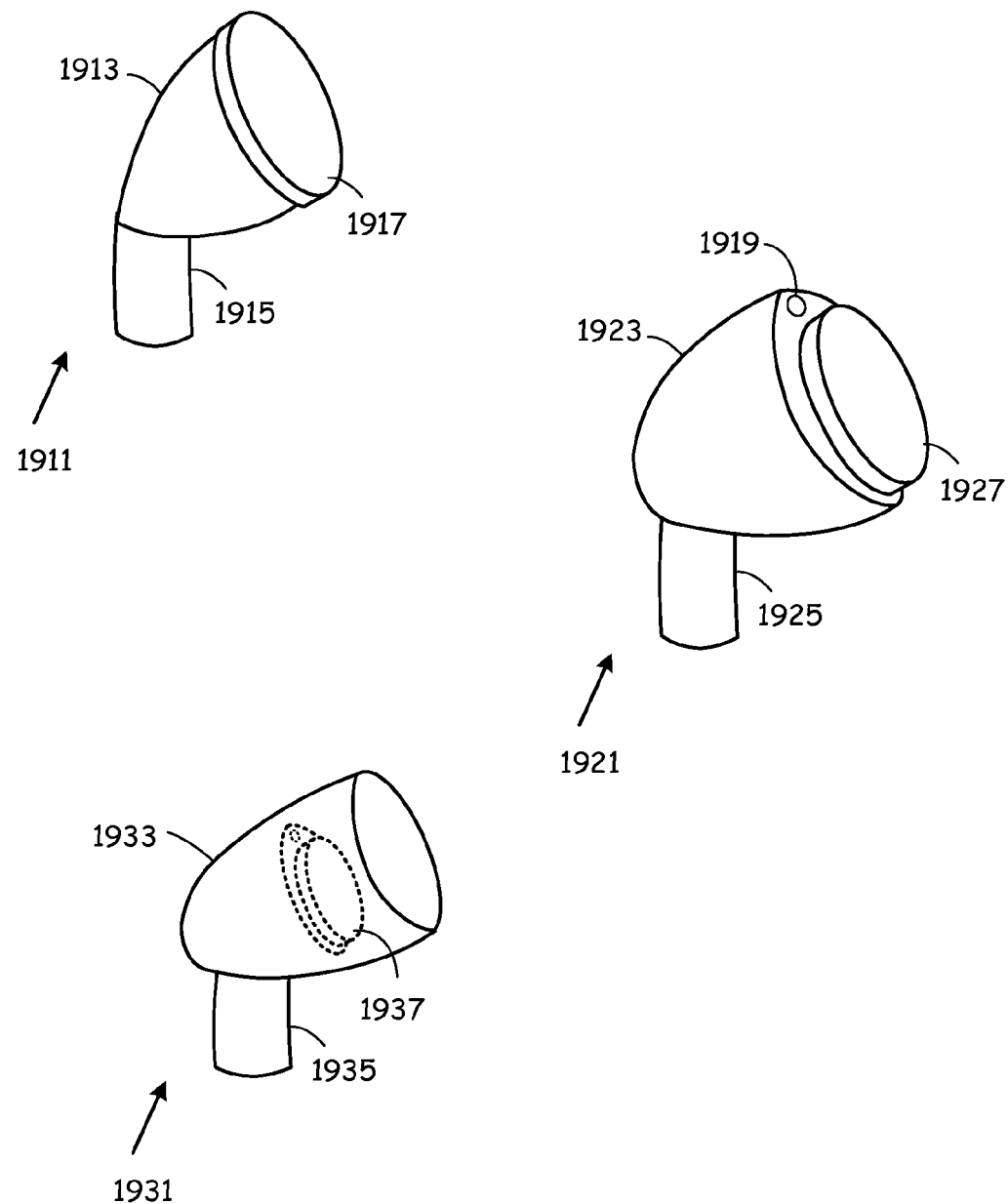
FIG. 19 is a schematic diagram illustrating hermetically sealed intravaginal monitoring device of FIG. 1; wherein the illustration depicts typical placement of a sonogram (ultrasound) on the surface of the hermetically sealed transparent cap.

FIG. 19 is a schematic diagram illustrating hermetically sealed intravaginal monitoring device 1911, 1921, 1931 of FIG. 1; wherein the illustration depicts typical placement of a sonogram (ultrasound) 1917, 1927, 1937 on the surface of the hermetically sealed transparent cap. The illustration 1911 shows first variety of sonogram placed within the hermetically sealed intravaginal monitoring device 1911, wherein a cap 1917 at the top of the cap 1913 acts as a sonogram (ultrasound) sensor-emitter head. Rest of the electronic components necessary for the sonogram 1917 may be located within the cap 1913 or stem 1915.

Similarly, the illustration 1921 shows a second variety of sonogram (or ultrasound) placed within the hermetically sealed intravaginal monitoring device 1921, wherein a cap 1927 at the top of the cap 1923 acts as a sonogram (ultrasound) sensor-emitter head (plus optical guidance 1919); which may be a complete intravaginal monitoring device 1921 or may be a removable external attachment. Rest of the electronic components necessary for the sonogram 1927 may be located within the cap 1923 or stem 1925. Moreover, the illustration 1931 shows a third variety of sonogram located deep within the hermetically sealed intravaginal monitoring device cap 1933, wherein a concealed cap 1937 acts as a sonogram (ultrasound) sensor-emitter head (plus optical guidance); which may be a complete intravaginal monitoring device 1931 all by itself or may be a removable external attachment. Rest of the electronic components necessary for the sonogram 1937 may be located within the cap 1933 or stem 1935.

Also note that the data acquired from a version of low powered sonogram 1917, 1927, 1937 that is a part of the intravaginal monitoring device 1911, 1921, 1931 may also be fed to an external standard sonogram machine. This is done by using wired and/or wireless communication interfaces. In this version of the low powered sonogram 1917, 1927, 1937, the intravaginal monitoring device 1911, 1921, 1931 may only be used as a sonogram head 1917, 1927, 1937, and a wireless dongle is plugged in from thereon. This allows the intravaginal monitoring device 1911, 1921, 1931 to communicate to the standard (sonogram) machines. Similar considerations also apply to other conventional types of sensing systems, such as a standard EKG machine or other machines that are routinely used in a birthing room.

Figure 20:
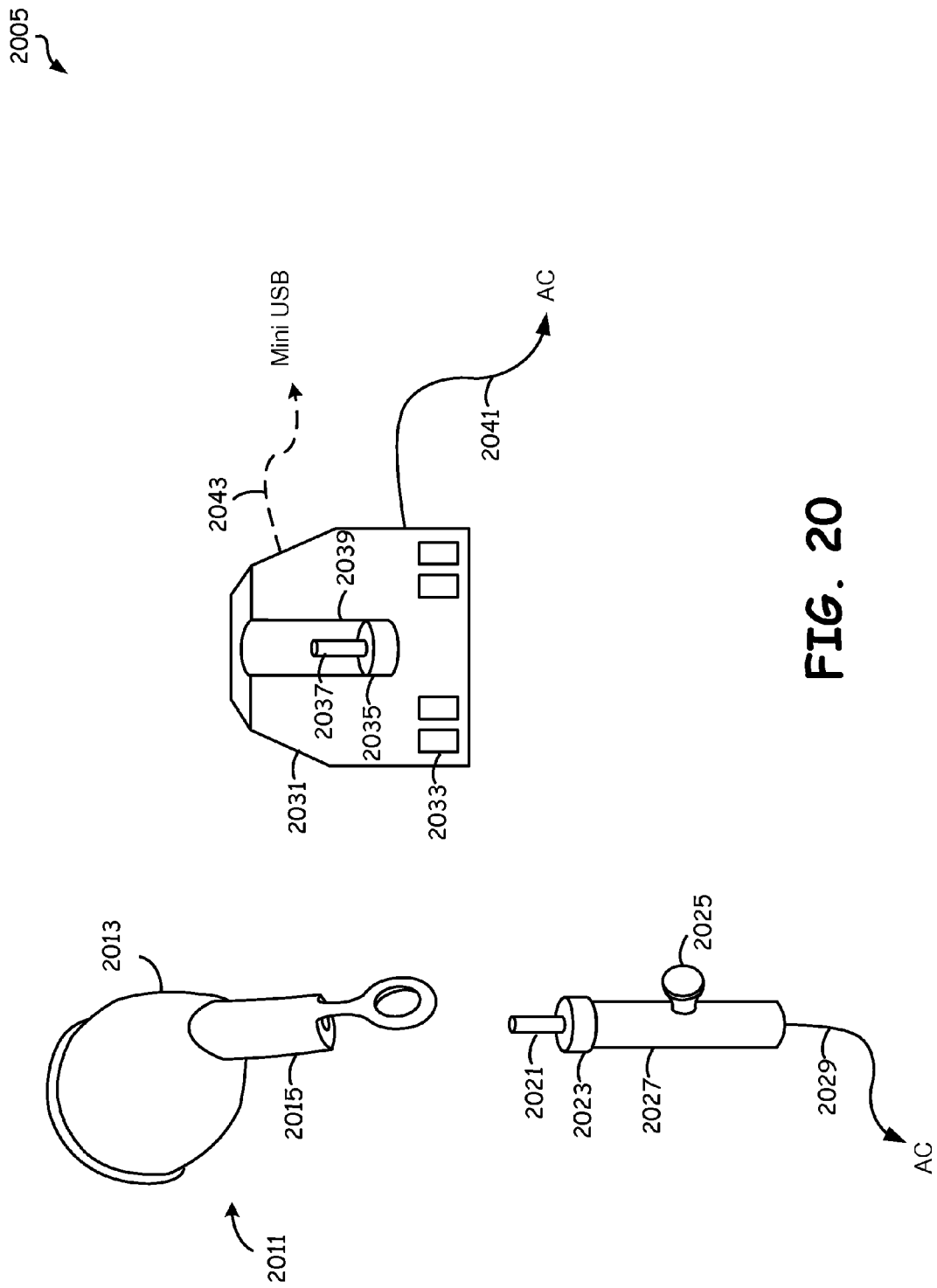
FIG. 20 is a schematic diagram illustrating hermetically sealed intravaginal monitoring device of FIG. 1; wherein the illustration depicts typical physical aspects of the powering and communication schemes.

FIG. 20 is a schematic diagram illustrating hermetically sealed intravaginal monitoring device 2011 of FIG. 1; wherein the illustration depicts typical physical aspects of the powering and communication schemes. In specific, the optionally hermetically sealed intravaginal monitoring device 2011 has a charger and communication device 2027 that is external to the hermetically sealed intravaginal monitoring device 2011 and that allows charging the batteries 2033 and external communication possible. In another variant of the invention, the device is not hermetically sealed.

The stem 2015 of the hermetically sealed intravaginal monitoring device 2011 contains a battery and communication compartment 2031, wherein the unit plugs into an external charger or communication unit via external plugs 2041 and 2041 (a mini USB, for instance). The illustration also shows the charger and communication device 2027 containing a power management system.

Figure 21:
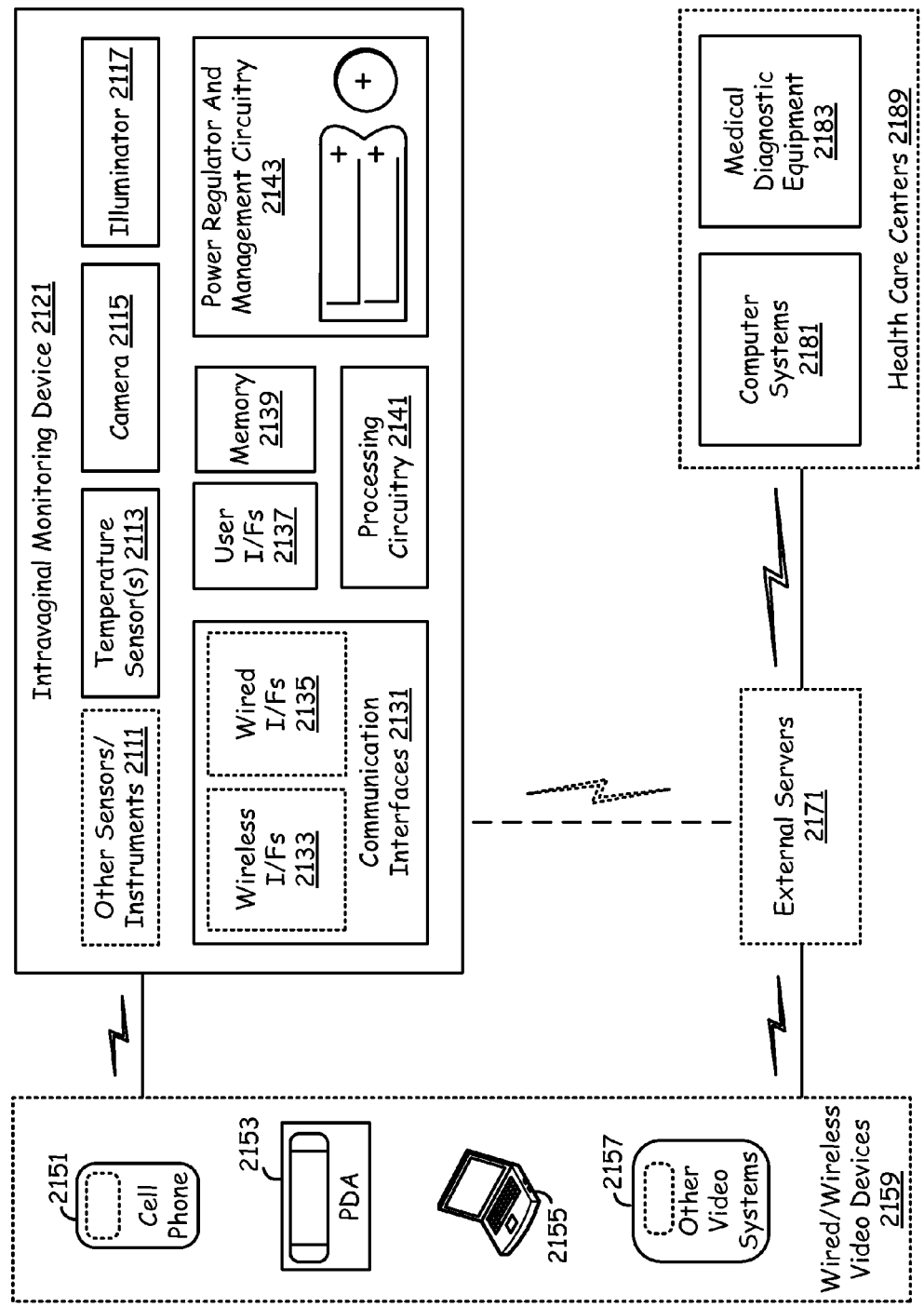
FIG. 21 is a schematic block diagram illustrating electronic components within the hermetically sealed intravaginal monitoring device of FIG. 1; wherein the illustration also depicts electronic infrastructural support from devices external to the intravaginal monitoring device, that includes electronic video systems, external servers and diagnostic equipments in healthcare centers.

FIG. 21 is a schematic block diagram illustrating electronic components within the hermetically sealed intravaginal monitoring device of FIG. 1; wherein the illustration also depicts electronic infrastructural support from devices external to the intravaginal monitoring device, that includes electronic video systems, external servers, consumer products such as an iPod, IPhone, etc. and diagnostic equipments in healthcare centers.

In specific, the illustration depicts electronic components located within the hermetically sealed intravaginal device 2121 (a part of it may be located external to it). The electronic components include camera 2115, illuminator 2117, temperature sensors 2113, other sensors and/or instruments 2111 (that may include sonogram and electrocardiogram), communication interfaces 2131, user interfaces 2137, memory 2139, processing circuitry 2141 and power regulator and management circuitry 2143.

The communication interfaces 2131 include wireless 2133 (such as Bluetooth) and wired 2135 interfaces that allow the captured and temporarily stored images and sensor data in the memory 2139 to be transferred to external wired/wireless video devices 2159, such as cell phones 2151, personal digital assistant 2153, computers 2155 and other video systems 2157. The other video systems 2157 may include digital photo and video devices, car tech and GPS devices, cell phones and smartphones, computers and hardware (e.g., notebooks, etc.), gaming devices, home theater devices, MP3 and video players and televisions. In yet a further aspect of the invention, the device includes global positioning system electronics. The global positioning electronics are used to identify the location of a device, in relation to other devices, e.g. mobile phones of a husband or a doctor, and in relation to the location of hospitals, birthing centers, and to time determine the distance and time of travel and arrival, and location of, e.g. an expectant mother to a hospital, an obstetrician to a hospital for a birth, a father to the birth of his child.

The captured and temporarily stored images and sensor data from these wired and/or wireless devices 2159 may be observed by the female or a healthcare professional or may later be transferred to external servers 2171. Finally the female may utilize them whichever the way she deems fit, that includes sharing them (and requesting for more information via Internet regarding a particular condition) or transferring them to healthcare centers 2189. Alternatively, the captured and temporarily stored images and sensor data in the memory 2139 may also be transferred (via, wireless or wired communication paths) directly from the intravaginal monitoring device 2121 to the external servers 2171.

Ultimately, in the healthcare centers 2189, they might end up in computers 2181 or medical diagnostic equipments 2183, for further processing, analysis, and investigations by the healthcare professionals.

Figure 22:
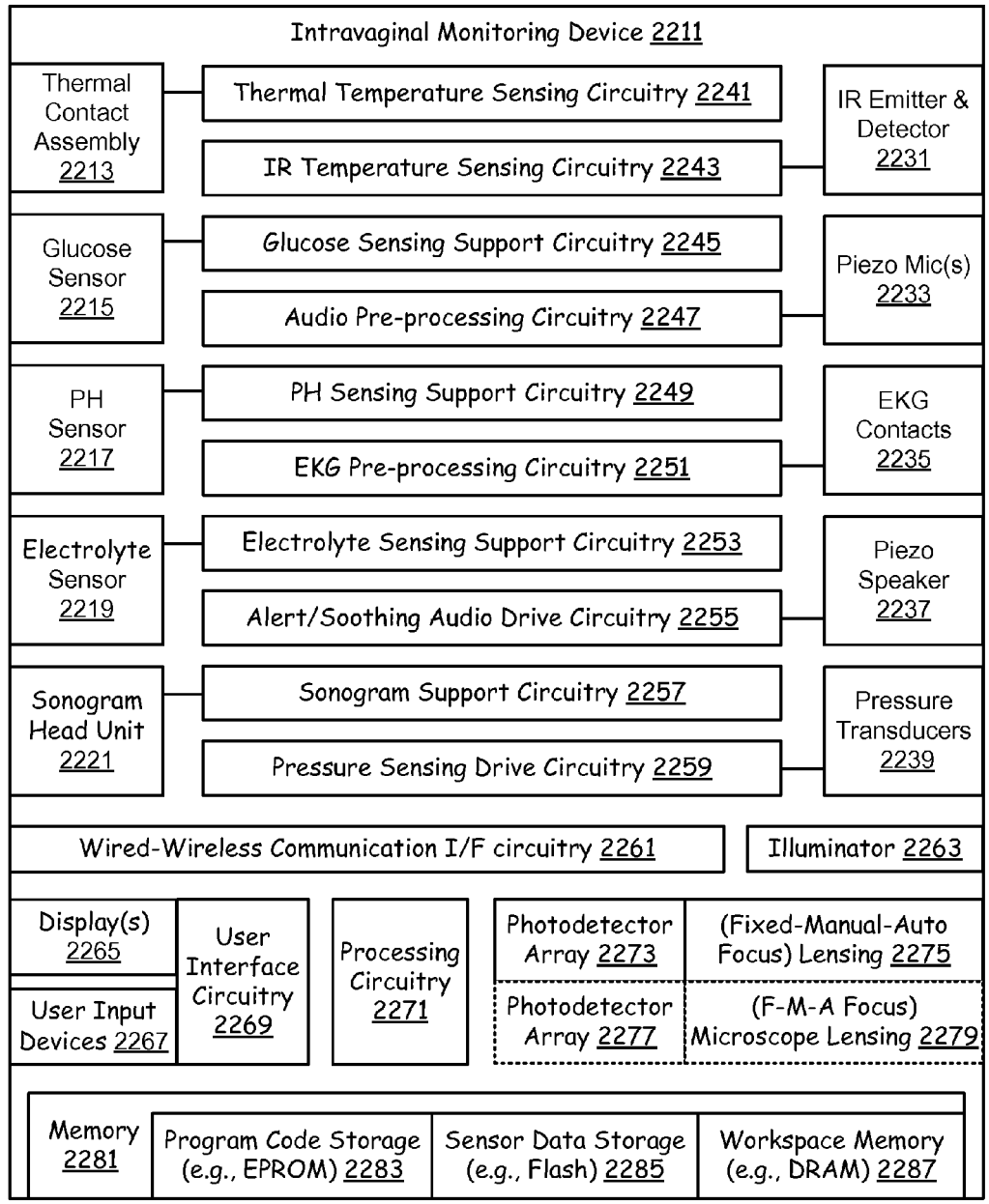
FIG. 22 is a schematic block diagram illustrating electronic sensory component within the hermetically sealed intravaginal monitoring device of FIG. 1, in detail.

FIG. 22 is a schematic block diagram illustrating electronic sensor components within the intravaginal monitoring device 2211 of FIG. 1, in detail. In specific, continuing from the FIG. 21, the current illustration depicts a plurality of sensors that in part or altogether are incorporated into an intravaginal monitoring device 2211.

To begin with, a thermal temperature sensing circuitry 2241 allow temperature reading to be taken via a thermal contact assembly 2213. This is accomplished via a thermistor temperature reading system in one variant. An infrared temperature sensing circuitry 2243 allows a temperature reading to be taken via an infrared emitter and detector assembly 2231. The temperature reading system, of the two types mentioned above, vary in the sizes of components required within the assembly as well as the time it takes to generate accurate readings. In practice, however, either only one or both of them may be employed, depending upon the space available within the intravaginal monitoring device 2211. Moreover, a pressure sensing drive circuitry 2259, via pressure transducers 2239, allow pressure readings to be taken.

Optional glucose sensing support circuitry 2245 allows glucose measurements via a glucose sensor 2215 and an optional PH sensing support circuitry 2249 allows PH measurements via a PH sensor 2217. Optional electrolyte sensing support circuitry 2253, via an electrolyte sensor 2219, allows the intravaginal monitoring device 2211 to generate sensory readings of electrolyte measurements.

Audio pre-processing circuitry 2247, via piezo microphones 2233, allows the intravaginal monitoring device 2211 to generate audible sounds generated within the area of the outer surface of the cervix or beyond, e.g. in the womb or uterus. This sensor is especially useful during pregnancy, to be able to hear the heartbeat of the developing fetus. EKG (electrocardiogram) pre-processing circuitry 2251 and sonogram support circuitry 2257 (via EKG contacts and sonogram head units respectively), allow during a pregnancy, to generate graphical readings of the electrical activity of the developing fetus's heart and the generate sonogram images of the fetus, respectively, in combination with the other features described herein.

In addition, an alert/soothing audio drive circuitry 2255, via a piezo speaker 2237, is also incorporated in some intravaginal monitoring systems 2211, to produce soothing sounds during pregnancy (e.g. for sensory stimulation of the mother, outside party, and or fetus within the womb) and at other times to reproduce the sounds generated within the intravaginal areas (via, the user interfaces, for an immediate assessment of a condition, for instance; including those sounds generated during pregnancy).

The illustration also depicts wired-wireless communication circuitry 2261, illuminator 2263, user interfaces 2269 (that include displays 2265—for the user observations, user input devices 2267), processing circuitry 2271, a camera sensing unit consisting photo detector arrays 2273, 2277 and fixed-manual-auto focus lensing units 2275, 2279, and memory unit 2281 (containing codes for program storage—an EPROM, for instance, sensor data storage—a flash memory unit, for instance, workspace memory—a DRAM, for instance).

Figure 23:
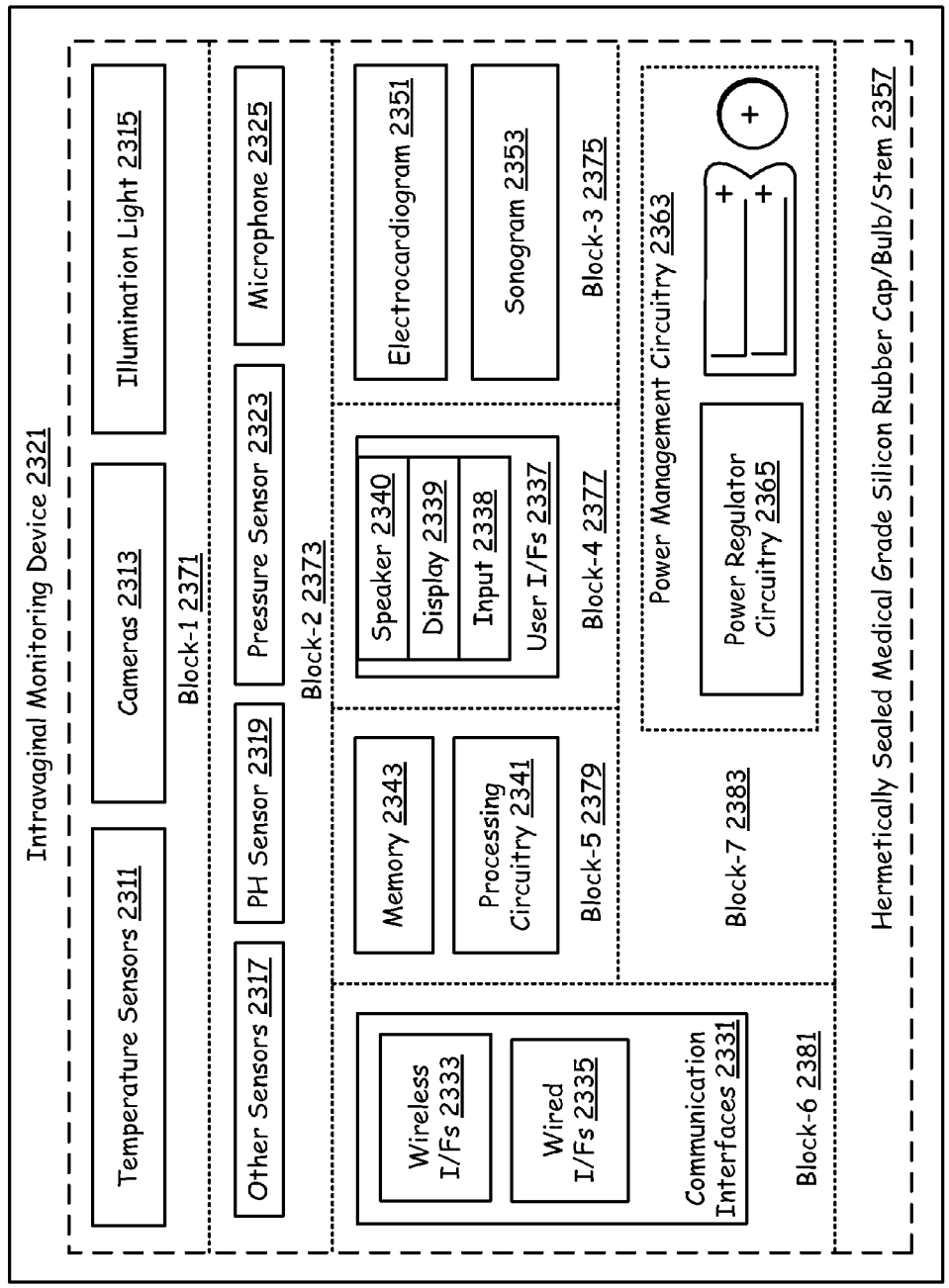
FIG. 23 is a schematic block diagram illustrating electronic components within the hermetically sealed intravaginal monitoring device of FIG. 1, in detail.

FIG. 23 is a schematic block diagram illustrating electronic components within the intravaginal monitoring device 2231 of FIG. 1, in detail. This illustration depicts the same components as those in the FIGS. 21 and 22, except that they are shown in blocks 2371, 2373, 2375, 2377, 2379, 2381, 2383, for the purpose of describing appropriate placements for them within the optionally hermetically sealed medical grade silicon rubber cap, bulb and/or stem 2357.

The components of the Block-1 2371 (consisting cameras 2313, illumination light 2315 and temperature sensors 2311) are typically located within the cap in one variant. The temperature sensors 2311 may also be located on the sides of the cap in another variant. The components of the Block-2 (consisting PH 2319, pressure 2323, microphone 2325 and other sensors 2317) are also located at the cap, but all or only some of them may also be located within the stem. Instruments of Block-3 (that include electrocardiogram 2351 and sonogram 2353) are also located in the cap partly, while the other part may be located within the stem in yet another variant.

User interfaces 2337 of the Block-4 2377 (that includes input 2338, display 2339 and speaker 2340 units) are mainly located in the stem (or neck area of the cap), since most of the cap regions are flexible and only stem retains firmly its shape. Processing circuitry 2341 and memory 2343 of Block-5 2379, and communication interfaces 2331 of Block-6 2381 (that include wired 2335 and wireless 2333 interfaces) are also usually located within the stem (because the cap area provides only limited space for these components in this variant).

Finally power management circuitry 2363 (that includes power regulator circuitry 2365 and batteries of various types) of Block-7 2383 may partly be located within the stem while the other part may be located externally (that includes AC power derivation for charging batteries).

Figure 24:
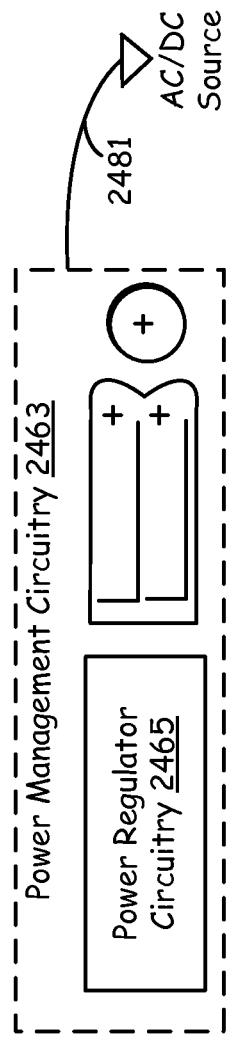
FIG. 24 is a schematic block diagram illustrating power management system located within the hermetically sealed intravaginal monitoring device of FIG. 1.

FIG. 24 is a schematic block diagram illustrating power management system 2463 located within the hermetically sealed monitoring device of FIG. 1.

The power management system 2463 typically includes a set of choice of batteries. The choice of batteries is determined by the amount of space available within the hermetically sealed intravaginal monitoring device and the intended amount of time of usage. The batteries (for instance, small cell type, watch, camera, or AAA sized batteries) may be either rechargeable (for instance, nickel-cadmium) or of the alkaline type. The power management circuitry 2463 may also be located as an external attachment unit that is to be incorporated while using the intravaginal monitoring device.

A power regulator circuitry 2465 transforms and converts ac voltage 2481 to DC of required voltage to recharge (and then regulates the voltage for proper recharging). In addition, the recharging of the batteries within the within the intravaginal monitoring device can also be done by using induction recharging methods and electronics.

Figure 25:
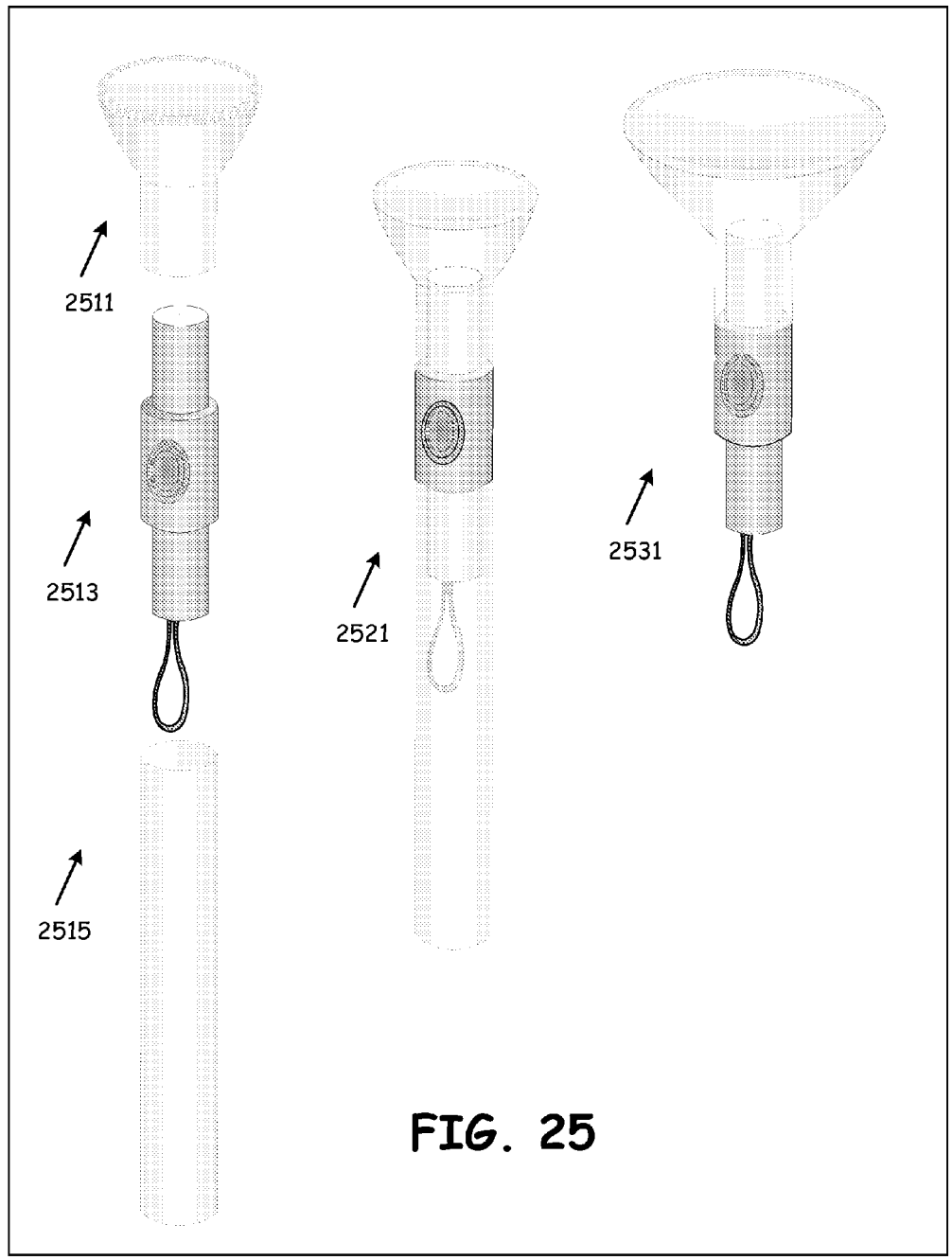
FIG. 25 is a schematic diagram illustrating prototypes of the intravaginal monitoring devices, built in accordance with the current invention.

FIG. 25 is a schematic diagram illustrating prototypes of the intravaginal monitoring devices, built in accordance with the current invention. The first illustration (containing parts 2511, 2513, 2515) depicts prototype of a complete intravaginal monitoring device that consists of a flexible and adjustable cap 2511, a stem 2513 (that also depicts an on/off switch and a finger ring) and the bottom part contains power management system and communication systems.

The next illustration 2521 shows all of these three parts (2511, 2513, and 2515) assembled together as a single unit. And the last illustration 2531 shows the two parts that put together make up a wearable intravaginal monitoring device. The devices shown have only one feature of a built-in camera, nonetheless, other embodiments may have more sensors and other electronic components built into them. Illumination is provided by LEDS.

Additionally, note that the typical dimensions of the cap diameter may vary between 3 to 5 centimeters and that of stem is 1.5 to 2 centimeters. Length of the entire unit may vary from 6 to 12 centimeters; and the angles of the cap may vary from 0 degrees to 20 degrees (the illustration of prototype show 0 degree angle alone).

Figure 26:
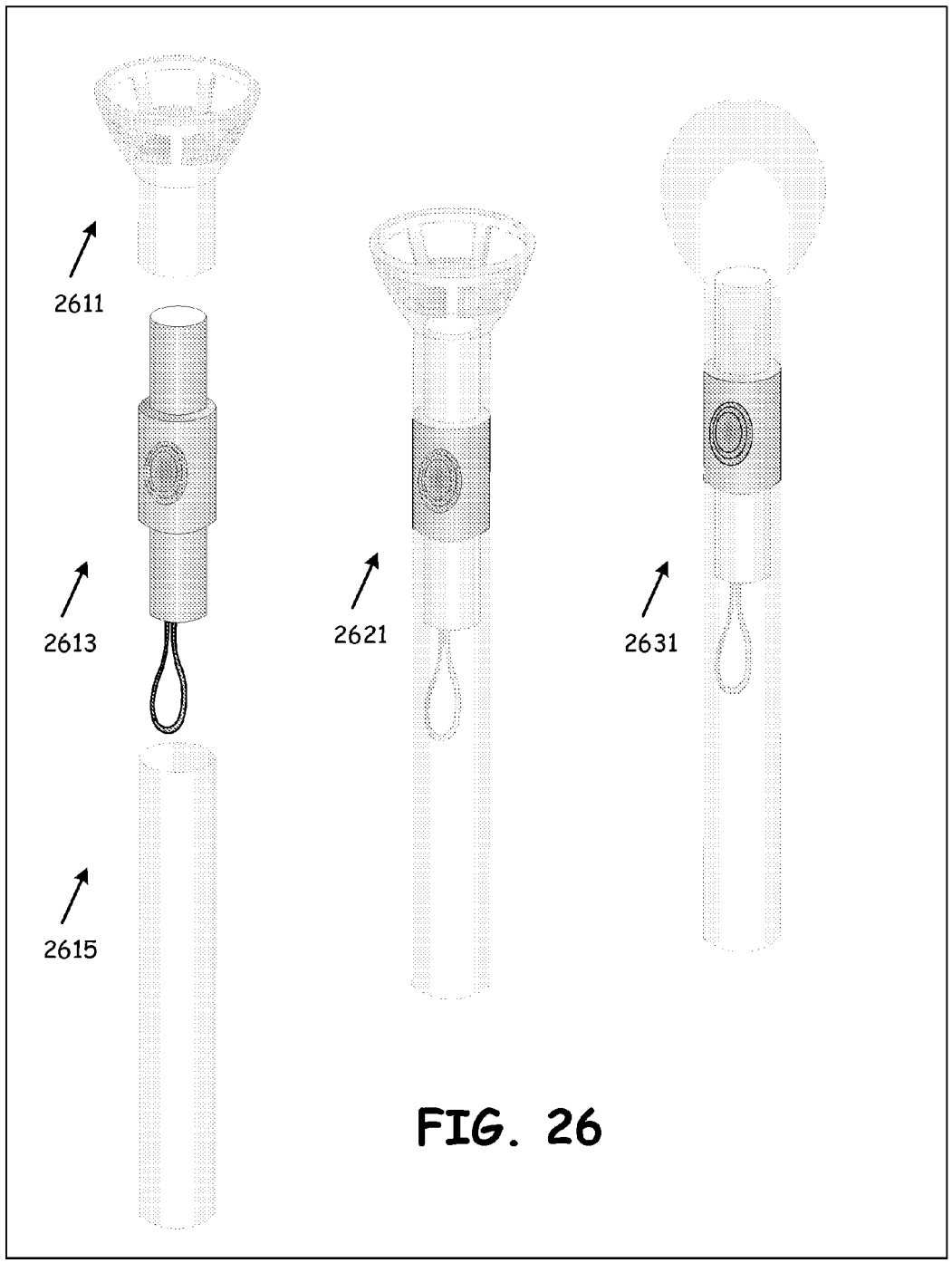
FIG. 26 is a schematic diagram illustrating prototypes of the intravaginal monitoring devices, built in accordance with the current invention, furthering from the FIG. 25.

FIG. 26 is a schematic diagram illustrating prototypes of the intravaginal monitoring devices, built in accordance with the current invention, furthering from the FIG. 25.

The first illustration (containing parts 2611, 2613, 2615) depicts prototype of a complete intravaginal monitoring device that consists of a flexible and adjustable perforated cap 2611, a stem 2613 (that also depicts an on/off switch and a finger ring) and the bottom part contains power management system and communication systems.

The next illustration 2621 shows all of these three parts (2611, 2613, and 2615) assembled together as a single unit. Moreover, the last illustration 2631 shows assembled unit that has a bulb cap instead of perforated cap. The devices shown have only one feature of a built-in camera, nonetheless, other embodiments may have more sensors and other electronic components built into them.

Additionally, like those of FIG. 25, typical dimensions of the cap diameter may vary between 3 to 5 centimeters and that of stem is 1.5 to 2 centimeters. Length of the entire unit may vary from 6 to 12 centimeters; and the angles of the cap may vary from 0 degrees to 20 degrees (the illustration of prototype show 0 degree angle alone).

Figure 27:
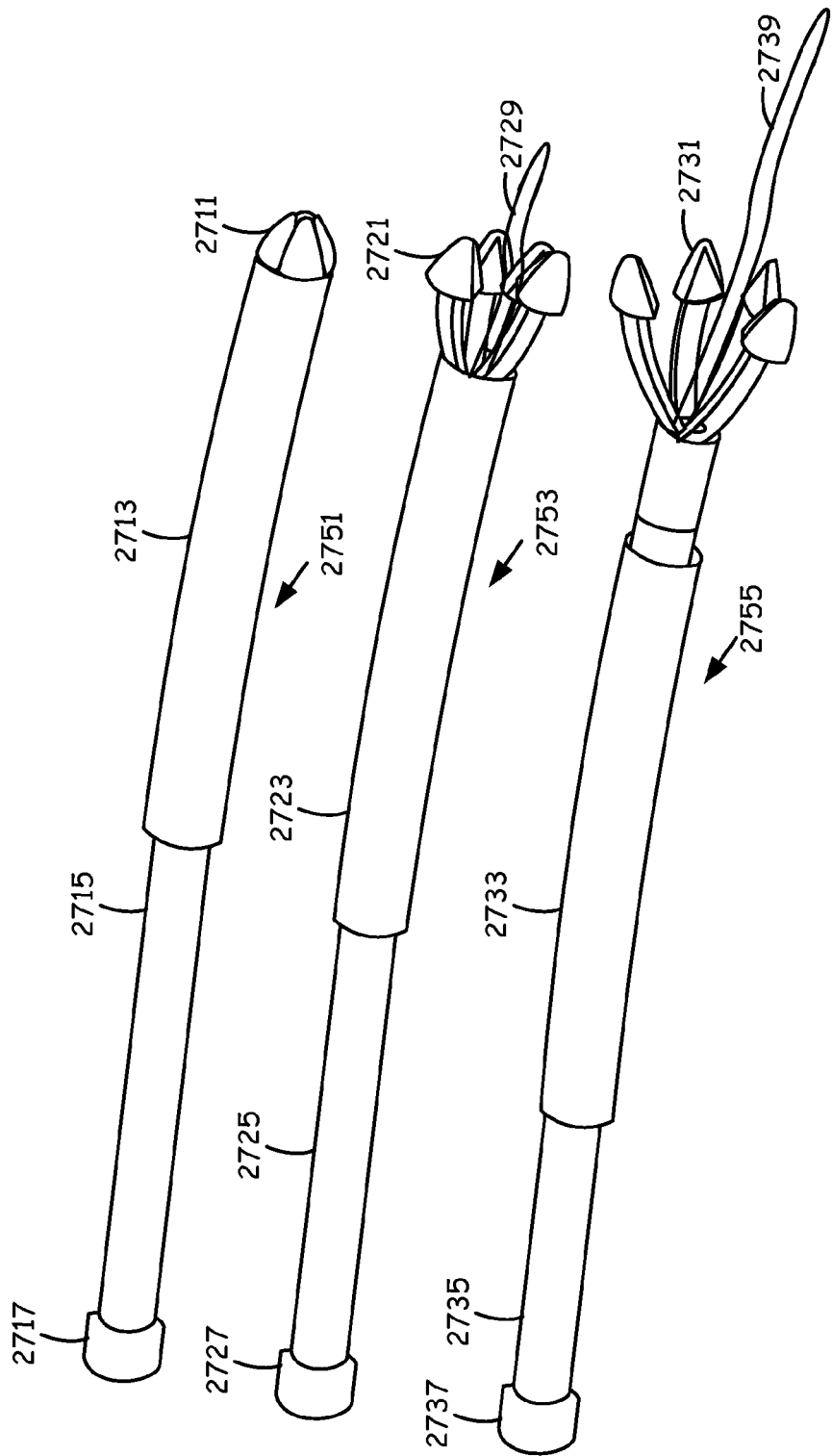
FIG. 27 is a schematic diagram illustrating hermetically sealed intravaginal monitoring device of FIG. 1; wherein the illustration depicts a flexible cap that opens up and a thin (2 to 3 mm in diameter, for instance) snakelike appendage that enters the uterus through the cervical canal in non female person, upon proper placement of intravaginal monitoring device and then pushing the bottom half of the stem.

FIG. 27 is a schematic diagram illustrating hermetically sealed intravaginal monitoring device 2751, 2753, 2755 of FIG. 1; wherein the illustration depicts a flexible cap 2711, 2721, 2731 that opens up and a thin (2 to 3 mm in diameter, for instance) snakelike appendage 2729, 2739 that enters the uterus through the cervical canal in non female person, upon proper placement of intravaginal monitoring device 2751, 2753, 2755 and then pushing the bottom half of the stem 2715, 2725, 2735. The snake appendage 2729, 2739 would have the same features and functionality as the base unit to which it is attached and are applicable to each and every physical embodiments of the intravaginal monitoring device described in FIG. 1 through FIG. 15.

Specifically, the illustration shows wearable intravaginal monitoring device 2751, 2753, 2755 that provides the female an expanding cap (that expands only after insertion; somewhat like tampon insertion—something wearers would be familiar and comfortable with); and then, a thin (2 to 3 mm in diameter, for instance) snakelike appendage 2729, 2739 that enters the uterus through the cervical canal in non female person. The different wearable intravaginal monitoring device 2751, 2753, 2755 contains a stem 2727, 2723, 2733 and finger ring (not shown). The electronics that is part of the intravaginal monitoring device 2751, 2753, 2755 is not shown; nonetheless they are incorporated within the cap 2711, 2721, 2731 and the stem 2715, 2725, 2735.

The intravaginal monitoring device 2751, 2753, 2755 then can be used for short term or long period of time, depending upon the needs. Moreover, other expansion schemes (along with the thin snakelike appendage 2729, 2739 that enters the uterus through the cervical canal in non female person) may also be employed, for instance, a spring release cap, screw out cap and so forth. The intravaginal monitoring device 2751, 2753, 2755 can also be non-wearable and usually is made up of medical grade silicon rubber.

Other aspects of the present invention can be found in additional functionality relating to all of the above embodiments such as that set forth as follows.

A vaginal monitoring device may consist of an imager for imaging and tracking clinically relevant changes, such as those related to an ovulation event and or the lack thereof. A fertility profile may be obtained from imaged and tracked data, and temperature sensing and tracking Correlation may be used in the process based on underlying data points or averages with prior or future data points or averages from such patient or from other patients.

Such and other vaginal monitoring devices may also be self powered or receive tethered power, and be fitted with wireless communication capability.

Various fertility evaluation methods may also be employed. For example, one method of determining which period of fertility a female is experiencing involves tracking the female's temperature, tracking images taken of a cervix, and correlating temperature with the images to obtain a fertility profile. Such temperature may be taken externally or taken within the vagina. The abovementioned method may further consist of presenting the fertility profile on a remote device, the remote device selected from the group consisting of a mobile phone, and iPhone™ a laptop computer, a server, a server communicatively linked to the Internet, and another computer connected to an Intranet.

A device for determining an ovulation profile of a female, the device comprising a self-powered, vaginally insertable electronic module and a housing, the housing further comprising an imager for imaging changes in a cervix, and an optional temperature sensor.

The abovementioned intravaginal monitoring device may also consist of a tracker, located within the device or optionally at a remote location, for tracking changes in the cervix over a period of time. The tracker is used to determine an ovulation profile of the female, by tracking changes in a cervix of the female with a wearable, vaginally insertable device to obtain cervix data, and tracking changes in the female's body temperature to obtain temperature data.

The abovementioned tracking changes may consist of tracking changes in intravaginal temperature, for example, and then, correlating the abovementioned cervix data with this temperature data. Then, this temperature data may be wirelessly sent to a remote device.

A remote device may be selected from a group consisting of a mobile phone, a smart phone, an IPhone™, a smart phone running an Andriod OS, an IPad™, a laptop computer, a server on a network, a cell phone tower, and another medical device to develop an automated method of knowing when a female is not fertile, consisting of determining the female's fertility profile from data collected using a vaginally insertable imager may thus be devised. The automated method consists of monitoring by gathering sample intravaginal (or otherwise) temperature and communicating securely the data or information based on the data to a remote device. The automated method may also consist of alerting the female as to fertility condition, by providing sensory stimulus to the female, for example, such as an audible stimulus, a visual stimulus, a vibratory stimulus, an electrical stimulus.

The intravaginal monitoring device may also consist of an imager for imaging and tracking clinically relevant changes related to a cervical incompetence event and or the lack thereof to obtain imaged and tracked data to obtain a cervical incompetence profile. The intravaginal monitoring device may be self powered, and optionally consists of a wireless communication capability and a light source.

By using the imager for imaging and tracking, for example, it is possible to determine whether or not a female has a cervical incompetence condition; tracking images being taken of a cervix taken within a vagina using a wearable, self-powered, wireless intravaginal monitoring device. Further, the imaged and tracked data is presented as a cervical incompetence profile on a remote device, the remote device may be one of a mobile phone, and iPhone™, a laptop computer, a server, a consumer electronic, a server communicatively linked to the Internet, and another computer connected to an Intranet.

The intravaginal monitoring device may also be used to determine if a pregnant female is suffering from cervical incompetence; the intravaginal monitoring device comprising a self-powered, vaginally insertable electronic module and a housing. The housing itself consisting of an imager for imaging changes in a cervix. The intravaginal monitoring device is thus capable of determining abnormal changes in the cervix. The intravaginal monitoring device further consists of a tracker for securely tracking changes (for privacy) in the cervix over a period of time, the tracker itself being located on the intravaginal monitoring device, or optionally at a location remote therefrom. The intravaginal monitoring device may also be used to alert the female by using a sensory stimulus, such as an audible stimulus, a visual stimulus, a vibratory stimulus, and an electrical stimulus.

The intravaginal monitoring device may also consist of an imager for imaging and tracking clinically relevant changes related to a sexually transmitted disease event and or the lack thereof to obtain imaged and tracked data, and optional temperature sensing and tracking capability to obtain sensed and tracked data. The normal values of image and tracked data may be optionally correlated to the sensed and tracked data to obtain a vaginal health profile. The intravaginal monitoring device is self powered, and optionally consists of a wireless communication capability and a light source. The process of identifying whether or not a female is experiencing symptoms of a sexually transmitted disease consists of tracking the female's temperature using a wearable, intravaginal monitoring device, optionally tracking images taken of a cervix taken within a vagina, and optionally correlating the temperature with the images to obtain a sexually transmitted event profile.

In conjunction with the intravaginal monitoring device, a process, that is used to monitor a female's reproductive health, may consist of taking a baseline cervical and/or vaginal profile using a wearable, intravaginal device, and taking a post sexual encounter cervical or vaginal profile. The process further consists of comparing the baseline profile to pre and post sexual encounter cervical profile, such as, one or more temperature measurements. This process may be used to electronically identifying a sexually transmitted disease. Moreover, intravaginal monitoring device may also be used treating a sexually transmitted disease condition. A database of sexual partner information may be used so as to chronologically correlate the sexual partner information with one or more sexually transmitted event profiles.

The intravaginal monitoring device may also be used to determine the sexual health of a female; the device consisting of a self-powered, vaginally insertable housing, which, in turn, consisting of an imager for imaging changes in a cervix and storage medium within the intravaginal monitoring device for storing a plurality of the changes, and an optional temperature sensor (the temperature sensor data being stored within the storage medium). The intravaginal monitoring device's tracker tracks changes in the cervix over a period of time; the tracker may be located on the intravaginal monitoring device, or optionally at a location remote therefrom.

A method, in conjunction with the intravaginal monitoring device, for determining a sexual health profile of a female, consists of tracking changes in a cervix of the female with a wearable, vaginally insertable device to obtain cervix data, and optionally tracking changes in the female's body temperature to obtain temperature data. The intravaginal monitoring device tracks changes in the female's body temperature by taking a intravaginal temperature readings. These temperature readings are then correlated with the temperature data, by securely wirelessly sending information from the intravaginal monitoring device to a remote device, such as, a mobile phone, a laptop computer, a server on a network, a cell phone tower, a consumer electronics product, and another medical device. The method may also be automated to know when and if the female is not clean; consisting determining the female's fertility profile from data collected using a vaginally insertable imager, and using an optional temperature sensor. The automated method may consist of collecting sample temperature data from the female, intravaginally and communicating this data or information based on the data to a remote device.

In all these, the data security, for the sake of privacy, are maintained. Moreover, the female is alerted, as to the presence and or absence of a condition associated with a female health profile, via a sensory stimulus such as an audible stimulus, a visual stimulus, a vibratory stimulus, an electrical stimulus.

The intravaginal monitoring device may also consist of an imager for capturing images of the interior of the vagina and/or images of the cervix (for tracking changes in a female's cervical and/or vaginal health condition), a data storage medium for storing the images, an optional wireless communicator for offloading the images from the device to a remote device, and an optional power source for the device for powering the imager, wherein the device is wearable and fully concealed with a vagina. Moreover, the intravaginal monitoring device may also consist of a monitoring module, such as a precancerous condition monitoring module, a cancerous condition monitoring module, a post treatment condition monitoring module, an STD related monitoring condition module, a physical abnormality monitoring module, an ovulation condition monitoring module, a non ovulation condition monitoring module, a pregnancy condition monitoring module, a non pregnancy condition monitoring module, a menopause monitoring module, and a premenopausal monitoring module.

The tracking of changes in a woman's cervical and or vaginal health consists of capturing images of the interior of a vagina and or images of a cervix with a wearable, self-powered, intravaginal monitoring device. The intravaginal monitoring device has optional data storage and an optional wireless communicator for storing and/or offloading the images. The intravaginal monitoring device is a fully insertable device (within the vagina), and it does not protrude outside of the vagina in a way that accidentally pushing it up into the vagina will not cause damage to the cervix.

In another embodiment, the intravaginal monitoring device may also be insertable, for monitoring female medical events in the vagina, consisting of a camera for capturing a digital image, housing that provides a view of a cervix for digital image capture of the cervix and/or an event occurring in the female. The intravaginal monitoring device may additionally consist of a light source, such as a light emitting diode, a cool light source, and a low heat emission light source. The event itself may include one of the female medical events such as pre-pregnancy events, a pregnancy, pre birth events, birthing events, and post-birth events. Moreover, the intravaginal monitoring device may be sized and dimensioned to be wearable by a user, that is, it is shaped to fit anatomical dimensions of a vagina.

For example, the intravaginal monitoring device may have a width no greater than 5 cm, length no greater than 15 cm, housing shaped to have a curvature (whereby it is easily insertable and removable by a user), and top portion larger than a lower portion of the device. The top portion seats the intravaginal monitoring device within the vagina so that it does not fall out when the patient is wearing the device. In non-human animals it is appreciated that dimensions, shapes, and sizes of the devices, caps and housing may be greater or smaller than those dimensions described above to properly sense and fit a particular non-human animal.

That is, the intravaginal monitoring device top portion has a bulbous shape, or optionally an off center bulbous shape. The bulbous shape is sized and dimensioned to be non-traumatic in the event a fetus passes through the cervix and comes in contact with the intravaginal monitoring device.

In another embodiment, the intravaginal monitoring device may have a housing that is sized and dimensioned to fit into a mammal's vagina and or birth canal, so as to provide a view of a cervix for digital image capture of the cervix and/or an event occurring in the mammal. The event itself may include a female medical event such as a veterinary animal medical event in a terrestrial mammal, and in a seafaring animal. The intravaginal monitoring device housing is constructed from and/or coated with an antibacterial material or coating.

In one of the embodiments, there are several sensors in the intravaginal monitoring device, which is sized and dimensioned to fit into a vagina. The sensors may include a temperature sensor, a pressure sensor, a pH sensor, and a heart rate sensor for the expectant mother, a heart rate sensor for a fetus. The sensor may also be an electrical impulse sensor that detects muscular activity and or inactivity. An algorithm is used by the intravaginal monitoring device, in conjunction with the abovementioned sensors, as to the usage of these sensors for a particular event. The algorithm may include software, firmware, or an application on a remote device.

The insertable, wearable, removable female intravaginal monitoring device may also consist of a communication link with a remote device, a microprocessor and memory. The intravaginal monitoring device may be self powered and the communication link may be a wireless communication link. The memory of the intravaginal monitoring device may be greater than 500 megabytes of memory, 2 gigabytes of memory, or 8 gigabytes of memory, for example. Moreover, the remote device may be one of a mobile phone, an Internet enabled phone, an iPhone™, a smart phone, a laptop computer, a desktop computer, a PDA, a server, a web server, a client server, an application server, a billing server, a hospital bed management server, and a patient management server.

In yet another embodiment, the intravaginal monitoring device, for insertion into a vagina, may consist of electronics to provide information about the condition of a cervix wirelessly to a remote device; the remote device may include one of a mobile phone, a smart phone, an iPhone™, a laptop computer, a desk top computer, a server, a web server, an applications server, and the intravaginal monitoring device being self powered. The intravaginal monitoring device itself consists of a processing circuitry, memory, and an information capture system.

The information capture system captures and stores vaginal information, and the processing circuitry functions so as to manage the storage of vaginal information in the memory via the information capture system. The information capture system itself may include a camera and one or more sensors and is disposed in or on a housing so as to provide a focal length to capture images of a cervix. The housing is shaped to fit a vagina and also consists of a self contained power source. The power source contains a battery, such as a rechargeable battery. The intravaginal monitoring device is hermetically sealed, and is sized and dimensioned to be retained by the vaginal anatomy. For example, the intravaginal monitoring device is shaped to maintain orientation, shaped to maintain position in the vaginal cavity and has a top portion and a bottom portion, wherein the top portion is larger in size than the bottom portion (so that the intravaginal monitoring device is sized for easy insertion and removability; such as, a portion of the device variably expands, whereby a field of view of the service is exposed).

In one of the embodiments of the present invention, the user may be able to purchase a kit containing an intravaginal monitoring device to measure subject parameters within a vagina and communicate those parameters to a remote device, and a plurality of housings sized and dimensioned to accommodate varying vaginal size ranges.

In an embodiment, the intravaginal monitoring device, for insertion into a vagina, may consist of electronics to measure and communicate subject information, the subject information at least partially obtained from within the vagina, and comprising a proximal end and a transparent distal end. The transparent distal end is designed to be non-traumatic, so as to minimize traumatic contact with an entrance to the cervical canal.

As an improvement on the abovementioned intravaginal monitoring devices (meant for woman's reproductive health monitoring, for pre-conception to post birth health monitoring, and or birth timing determination), the intravaginal monitoring device consists of a system designed to align a camera or imager with a central cervical area or other area of the cervix. The camera or imager may also capture a sequence of images.

In one of the embodiments, the intravaginal monitoring device, insertable into a vagina for monitoring events occurring over a period of time, may consist of an information processing system that captures events, and then provides a timeline of the events on a graphical user interface on the device or a device remote from the intravaginal monitoring device, or a combination thereof. The abovementioned events may include a preconception event, a conception related event, a fertility event, a post conception event, a first trimester event, a second trimester event, a third trimester event, a pre-birth event, a post birth event, a sexually transmitted disease event; and the intravaginal monitoring device itself may be self powered and may contain a wireless communication link. The intravaginal monitoring device may communicate with the remote device using an Internet protocol using the secure wireless communication link. The remote device may include one of a secure mobile wireless network, a secure Intranet, and the Internet via a secure data transfer protocol.

The intravaginal monitoring device that is insertable into a vagina may also consist of an information processing system. The information processing system may include a camera that captures continuous images of an area inside the vagina.

Moreover the intravaginal monitoring device may also consist of a data capture system within the vagina, containing one or more light emitting diodes.

The intravaginal monitoring device may additionally contain a communication system for communicating data captured from within the vagina, externally of the vagina, to an external system. The data may be selectively transmitted externally of the vagina, while certain of the data is kept as a back up on memory located on the device.

The intravaginal monitoring device that is insertable into a vagina may include an information capture system, and a wireless communication link for selectively transmitting data captured by the information capture system externally of the device, and a back up memory storing all or a portion of the data. The wireless communication link may have an antenna such that transmission of RF signals is directed away from a fetus (and such that the transmission of RF signals is directed away from a wearer's torso or internal organs). The wireless communication link may be a half duplex communication link and may have a mode of operation that is a half duplex mode of operation. Alternatively, the wireless communication link may be a half duplex communication link and may have a mode of operation that is a full duplex mode of operation. The wireless communication links of the intravaginal monitoring device may also operate in a half duplex mode of operation while a wearer has the intravaginal monitoring device inserted in to the vagina, and may operate in a full duplex mode of operation while the device is external to the wearer. It is appreciated that the device described above is used to create a telemedicine network and system.

The intravaginal monitoring device also consists of an external communications system, that may include a cell phone, a medical staff terminal, a doctor's terminal, a doctor's terminal, an obstetrician's terminal, a midwife's terminal, a doctor's mobile phone, a doctor's iPhone™, an expectant parents mobile phone; while each of the devices capable of being operated in a standalone mode with the insertable intravaginal monitoring device, or capable of being used in a communications network with the internal device.

The intravaginal monitoring device also is able to obtain compressed captured information so as to minimize band width usage, optionally encoded, and/or optionally encrypted before delivery to an external system. The external system may include any of those that are described above. The external system consists of one or more of the following, alone or in communicative combination, a mobile phone, an internet telephony system, a mobile phone network, a mobile phone system, a WIMax system an Intranet, and the Internet. Similarly, the device and system herein selectively transmits sensor data, so that clinically irrelevant data is not transmitted, and only clinically relevant data is transmitted.

The captured information itself may include the information captured from a temperature sensing system, an optical capture device, a sonic capture system, an infrared capture system, an optical capture range mode, an optical system with a lensing system, a Ph monitor, and so forth.

The intravaginal monitoring device may also contain an information capture system or component that consists of a drug delivery system controllable by decisions made by the processing circuitry of the intravaginal monitoring device, alone and or in combination with commands to the intravaginal monitoring device coming from externally of the device.

Additionally, the intravaginal monitoring device's information capture system may also be able to compare one frame taken at one time with another frame taken at a different point in time to obtain a comparison. Based upon the comparison, the intravaginal monitoring device may be able to determine a gynecological event and or an obstetrical event. The event itself may consist of an abnormal event associated with a pregnancy, spotting, discharge from the cervix, blood spotting; and the intravaginal monitoring device, by itself, is capable of determining the presence of blood spotting emitting from a cervical opening to obtain a determination. Moreover, the intravaginal monitoring device also communicates an alert to notify a subject of an abnormal event or externally to a remote device notifying a third party of the abnormal event.

The intravaginal monitoring device may also contain an image processing system, in which one frame taken internally of a subject and at one point in time is compared to another frame taken at a second point in time. Here, the image processing system is used to determine whether a gynecologically or obstetrically relevant event has occurred and or has not occurred.

The gynecologically or obstetrically relevant event may include a color change event, a fluid discharge event, an event associated with an infection, a contraction event, a temperature change event, an event associated with tissue change, an event associated with tissue discoloration, an event associated with the presence of an abnormal fluid within the vagina, an event associated with the presence of a pathogen in the vagina.

The intravaginal monitoring device (the abovementioned device for vaginal insertion and information capture) itself may contain a processing circuitry, memory, and an information capture system, and a dock or docking system for the device external to the vagina. The dock receives and forwards information from the intravaginal monitoring device, optionally charges it, and/or optionally provides a communication link for the intravaginal monitoring device.

The intravaginal monitoring device of any of the preceding disclosures in which the dock may also be used to communicate information from the intravaginal monitoring device to an Intranet and/or the Internet to a remote device. The intravaginal monitoring device is inserted into the vagina for digital image information capture, and contains one or more sensors capable of measuring physiological parameters of interest, regarding conditions of a female or an offspring inside the womb of the female. The dock may also have a visual communication capability with a subject; such as an LEDs, a black and white or color display.

The information capture system, for capturing data within the vagina, is also capable of processing the captured data thereon. A microprocessor and software and/or firmware perform the abovementioned processing of the captured data. Further processing of the abovementioned data may occur on a remote device from the intravaginal monitoring device insertable in the vagina.

The information capture system, for capturing data within the vagina, is also capable of processing all or a portion of the captured data thereon, the intravaginal monitoring device further consisting of a tether serving as a communication link to an external device. The tether may consist of a cable for energizing the intravaginal monitoring device directly or recharging a battery on the device. The tether of the system or intravaginal monitoring device of any of the preceding disclosures is communicatively linked to the dock; which in turn draws power from a communication bus and/or the device draws power from a communication bus. The communication bus consists of a USB or a wired Ethernet.

A rechargeable battery powers the intravaginal monitoring device, and is charged by a recharging device. The recharging device consists of a device that is commonly used, such as those used in recharging rechargeable tooth brushes. Instead of the rechargeable batteries, the intravaginal monitoring device may also be self-powered, wherein the intravaginal monitoring device is wearable by a user.

A communication link is used for sending information from the intravaginal monitoring device, while it is inserted in the vagina, to a remote device. The communication link may be a wireless or wired ones. And the remote device itself may be a mobile phone.

The intravaginal monitoring device of any one of the disclosures herein further contains a housing that spreads the vaginal tissue so that a full or substantially full view of the cervix can be captured, wherein the housing contains a power source. The intravaginal monitoring device is sized and dimensioned for comfort for the user and to fit the user's anatomy while capturing streamlining video of the cervix. The intravaginal monitoring device for data capture of events within a vagina consists of a data capture system for capturing information while the device is inserted in the vagina, the intravaginal monitoring device being open at one end.

The data capture system, for capturing information, while the intravaginal monitoring device is inserted in the vagina, is closed at one end. Alternatively, the intravaginal monitoring device may contain a data capture system (to capture events within a vagina), that includes an expander, which provides for a field of view of a female's internal anatomy; the data capture system being located within the expander, and being integral therewith.

The intravaginal monitoring device is hermetically sealed, and the expander itself does not breach the hermetic seal. The data capture system, for capturing information while the intravaginal monitoring device is inserted in the vagina, containing an optional limit stop. The limit stop prevents the device from insertion to an undesirable distance within the vagina and the limit stop itself is variably adjustable.

The data capture system, for capturing information while the intravaginal monitoring device is inserted in the vagina, consists sonic circuitry capable of processing and identifying a heart rate, the heart rate selected from a heart rate of an expectant mother and a heart rate of a fetus in a womb, and a processor for processing and identifying a heart rate of one or more beings located within a womb of an expectant mother.

The data capture system may also contain an infrared transmitter and receiver designed to determine and/or identify one or more physiologically relevant events for a female and/or beings within a womb of the female. The data capture system, for capturing information while the intravaginal monitoring device is inserted in the vagina, may consist of one or more of piezos. The piezos are used to identify, quantify, and/or determine data comprising contraction data, and/or any other obstetrically or gynecologically events of interest.

The intravaginal monitoring device may contain a contraction tracking system, the contractions being determined optically by the contraction tracking system. This is done by frames taken at one time being compared to frames taken at a second point in time by the abovementioned contraction tracking system. The intravaginal monitoring device (data capture system being a part of it) may also provide useful contraction information, using a contraction tracking system, the contractions being determined electrically by the contraction tracking system. This is done by the contraction system, by analyzing, and hence determining, pressure contraction measurements. The intravaginal monitoring device may be assisted by an EKG system, which determines electrically using EKG; the EKG may include that of an expectant mother and a being within the womb of the expectant mother, and a discriminator for separating the two EKGs.

The intravaginal monitoring device may consist of a data capture system for providing contraction information (by way of example in a graph, e.g. contraction intensity and periodicity) using a contraction system, the contraction system may use multiple mechanisms for determining useful information associated with the contractions. For example, the data capture system may provide information about the heart rate of a user, an infrared system within the data capture system may provide the change in volume of blood flow, a heart rate detector of a fetus inside the womb of the user may provide the information about an expectant mother and a fetus within a womb. In all of these cases, the intravaginal monitoring device consists of a data capture system and a womb and/or fetal monitor. The womb and or fetal/monitor further contains an electronic patch with one or more sensors described herein placed on the stomach of the mother. The patch in turn is wirelessly communicatively linked to remote device, the remote device may include a mobile phone, a computer, the device, the Internet, an Intranet, a mobile phone network, a device used in a birthing room, and sensor data transmitted thereto.

The intravaginal monitoring device may also consists of a full duplex mode of operation for obtaining physiological data about a user of it, the intravaginal monitoring device being sized and dimensioned to comfortably be worn in the vagina for periods of time, the intravaginal monitoring device being self powered. The intravaginal monitoring device, having the abovementioned mode of operation, uses one or more techniques described above to capture and refine the data obtained. The above mentioned mode or operation and processing capability may exist inside the intravaginal monitoring device; in this case, the intravaginal monitoring device, for obtaining information about a female's reproductive organs, may have wireless communication functionality. The intravaginal monitoring device is sized and dimensioned to be worn within a vagina during data capture mode, the data capture mode lasting in the range of 15 minutes to several months. The intravaginal monitoring device is also sized to maintain its data capture position when the wearer is in an upright walking position.

In one of the embodiments of the present invention, an entire system for obtaining information about a female's reproductive organs may consist of an intravaginal monitoring device worn inside the vagina for data capture, and a remote device communicatively linked to it; the remote device providing processing power support for data communicated from the intravaginal monitoring device. The intravaginal monitoring device that is sized and dimensioned for, full or partial, insertion into a vagina may have a mode of operation that looks at streaming video data, analyzes this data to obtain results, and externally sends the results to a remote device. The intravaginal monitoring device, sized and dimensioned for insertion into a vagina, may consist of another mode of operation in which post processed data is delivered from the intravaginal monitoring device to a remote device. In this case, the post processed data is delivered from the remote device. The intravaginal monitoring device itself may consist of a microprocessor, and a physiological data capture mode of operation.

The system for monitoring conditions within a woman's vagina (including features of any of the disclosures herein), consists of an insertable intravaginal monitoring device for insertion into a woman's vagina, it consists of information capture features, and an external processor located outside of the woman for processing the information captured by the intravaginal monitoring device. In this system, the intravaginal monitoring device includes a communication link sending information from it to the external processor. The external processor itself may be a part of a web server, a mobile phone communicatively linked to a mobile phone network, a laptop computer, a desk top computer, and a consumer electronic product.

The intravaginal monitoring device or a system that includes the intravaginal monitoring device, for obtaining information from a woman's vagina, may consist of a mode of operation effected once a threshold of a value has been met; the threshold in turn activates a warning and or an alert. The warning or an alert may include one of a warning to the expectant mother and/or father that an abnormal event associated with a pregnancy is occurring or has occurred, a warning concerning about amount of time prior to a birthing event, a warning concerning a gynecological abnormality, a alert concerning a fertility event, a warning concerning an infertility event, a warning concerning an event associated with an infection.

The intravaginal monitoring device (self-powered), to capture information, and/or system including therewith, is capable of capturing data of events and presenting this data in a chronological manner. The events themselves may include a normal pregnancy event, a spotting event, a bloody discharge event, and an abnormal pregnancy event; presented in a histogram format or as a time line on the device (at remote devices communicatively linked to the intravaginal monitoring device, at a mobile phone, at a computer remote from the device, at a device comprising a wireless communication link). Alternatively, the intravaginal monitoring device or the system may store the event data and then send the data outside of it to a device other than the remote device. Alternatively, the intravaginal monitoring device may capture data of events and store them in a memory, and then transfer data post removal of the intravaginal monitoring device from the vagina.

The intravaginal monitoring device may also capture data within the subject and send to a network communicatively linked thereto; a number of nodes on the network thus being communicatively linked to the intravaginal monitoring device. This system including a warning infrastructure mode, in which processing of the data occurs in anyone of those nodes in the network.

As an improvement on the system, the intravaginal monitoring device consists of a module to advise another module that alerts the subject about an insertion time, keeping inside time, and a removal time for the intravaginal monitoring device. Alternatively, the intravaginal monitoring device and system may consist of a module to advise a module that warns the subject that the device has been inserted for too long a period of time or a period of time not long enough, or of a series of possibly detrimental events. Moreover, as a part of improvement, the intravaginal monitoring device and system may provide a warning visually, audibly, and/or by vibration, or a combination thereof.

Another improvement may consist of having at least one microphone (such as a directional microphone) that audibly picks up a subject's heart rate, the subject located within a womb; the microphone is aimed where the subject is located. The intravaginal monitoring device may consist of a processing circuitry located internally on the device, or externally from the device. The processing circuitry may be, for example, located on a patient's PC, and/or at a web server.

The intravaginal monitoring device, as an improved electronic device for capturing data, sized and dimensioned to fit into a vagina and be wearable therein or close by, and/or system (consists the intravaginal monitoring device and a dock), wherein the improvement consists of a notification system. The dock may be communicatively coupled to a cell phone, an iPod, a PDA and or PC; whereby the dock also functions to provide the intravaginal monitoring device with a power source. The intravaginal monitoring device may also communicate the data to a doctor's system with a presentation module, where medical personnel review the data. The capturing of physiological data from inside the subject's vagina using the intravaginal monitoring device to a remote electronic device, and sending the instruction data to the intravaginal monitoring device for receipt by the device.

The abovementioned data may include audio data, data instructing the device to behave in a certain manner, instructions for the intravaginal monitoring device to offload or engage in a specific type of data collection, and video data. The audio data itself may also be sent from the intravaginal monitoring device to a remote device. The video data from the intravaginal monitoring device may also be sent to the remote device, whereby the subject's images including physical state are visualized at the remote device.

Instead of one way, there may also be a two way communications between the intravaginal monitoring device and remote device. The device for capturing data obtained from within a subject's vagina may also consist of GPS functionality. The communication link itself may include a low power Bluetooth communication link, a cellular radio communication link, a half duplex communication link oriented away from the subject located in a womb of an expectant mother, whereby power consumption is minimized. The modes of operation of communication itself may include a half duplex mode of operation and a full duplex mode of operation. The intravaginal monitoring device operates in a half mode duplex mode of operation when inserted in a vagina and a full duplex mode of operation when outside of the vagina. Also, the intravaginal monitoring device may enter into a low power mode of operation when the device detects it is not inserted into the vagina.

The intravaginal monitoring device may also consist of a sonogram image capture sensor, functionality and mode of operation; consisting of a sonic emitter (being optionally controlled externally and/or internally) and in which the analysis of sounds occur externally. The intravaginal monitoring device may also communicate to existing sonogram systems external to the subject. In the sonogram capture mode, the intravaginal monitoring device may function so as to be able to monitor the subject in a womb's anatomical position in relation to a cervix. The sonogram capture mode works to monitor a position, the position being selected from the fetal position, position of head, position of a fetal foot, an incorrect birthing position, and a correct birthing position. The intravaginal monitoring device may also consist of an early notification functionality of baby position based upon sonogram data. The sonogram data may also allow determination of the subject in a wombs weight, in a womb's head size, baby's size of its head, and periodically catching of a sonogram shape of the head or the baby. The sonogram may also have a mode of operation for determination of daily baby in womb growth rate (in absolute terms, e.g. grams, or in percentage growth rate) and/or providing a histogram or chart tracking the in womb growth rate (inclusive of tracking development of the baby in the womb prior to, at full term development, and post normal full term birthing time).

There also exists a mode of operation for determining ovulation based upon physiological readings taken by the intravaginal monitoring device, and/or an external sister device (inclusive of tracking of development of a baby in the womb prior to, at full term development, and post normal full term birthing time). The mode of operation may also include operation for tracking pre-conception, conception, post conception, after full term female events. The mode of operation, in addition, may also include operation for tracking development of a baby in the womb including a record of the baby's in womb movements, the in womb movements including hand, torso, arm, leg, head and foot movements. The mode of operation may also include operation for providing a timeline of the entire cycle of female gynecological and obstetric events. The mode of operation may also include an operation for logging the date and/or time when the woman has sex into the device, system or method. The mode of operation may also include an operation for logging a woman's menstrual period events. The mode of operation may also include an operation for monitoring and/or logging impregnation, a birthing process, and/or a post birthing process. The mode of operation may also include an operation for monitoring the swelling of the cervix events and/or color changes in the cervix events. The mode of operation may also include an operation for recording these events. The mode of operation may also include an operation for monitoring and recording menopause events. The mode of operation may also include an operation for monitoring events of premenopausal woman who wants to get pregnant, and a mode of operation for predicting and displaying an optimal time for impregnation. The mode of operation may also include an operation for creating a time line of lifetime cervical and vaginal changes. The mode of operation may also include an operation for determining an optimal timing window for insemination or in vitro fertilization. The mode of operation may also include an operation for administration of drugs or sperm from the intravaginal monitoring device. The mode of operation may also include an operation for alerting a subject when to administer a drug and the proper timing of administration of a drug. The mode of operation may also include an operation for administrating a drug to increase fertility and communicating to a user to administer the drug, and/or and external pump (like an insulin pump) to administer the drug and or sperm to a patient, and external pump and related circuitry getting its data and commands from this device or system, and a mode of operation for adjusting the drug dosage and administration regimen.

The intravaginal monitoring device further consisting a drug administration system, and in which there is a mode of operation for slowly controlling the dosage and administration of one or more drugs to create a profile or digital image of the cervix that is desired to achieve a therapy or event. The drugs are used to achieve fertility or implantation of in vitro embryos, in the intravaginal monitoring device and system of any of the disclosures herein. The intravaginal monitoring device, in one of the embodiments, has a broader three dimensional shape at a first end than at the other end of it. The housing itself is sized and shaped to be a self-orienting one upon insertion into the vagina. The mode of operation may also include an operation for tracking and recording, a heart rate, the heart rate selected from the group consisting of a child's heart rate, a mother's heart rate, and optionally a mode of operation for distinguishing one from the other and presenting same, at a point later in time, in real time, simultaneously on the device or system. The mode of operation may also include an operation and electronics for taking a real time sonogram of a baby in a womb of a subject taken by the device and presented on a remote device, e.g. cell phone, wireless communication enabled television, web enabled television, whereby a husband can sit with wife and see the baby in the womb in real time or at a time delay. The mode of operation may also include an operation providing a graphic user interface, the graphic user interface (GUI) selected from an expectant mother's graphic user interface, an expectant father's graphic user interface, a hospital administrator's graphic user interface, an obstetrician's, a doctor's GUI, a nurse's GUI, a midwife's GUI. The mode of operation may also include an operation for creating an electronic medical record preconception to post birth for one or a multiplicity of subjects, in womb babies, and post birth families.

The intravaginal monitoring device disclosed herein in which some or the entire device is disposable or reusable and in which the intravaginal monitoring device is made from a biocompatible material. The biocompatible material may include a medical grade silicone, a metal, or a carbon coated metal. Alternatively, the biocompatible material may include a silicone, a plastic, an acrylic, a glass, a metal, and a medical grade material.

The mode of operation and electronics, for this intravaginal monitoring device or system to communicate its information to a remote device, may include a hospital billing system, a doctor's office invoicing system, a reimbursement system for a national healthcare system, a monitor used traditionally in a birthing center, or a monitor used in a gynecological doctor's office, hospital or clinic. The remote device itself may include a hospital billing system, a doctor's office invoicing system, a reimbursement system for a national healthcare system, a monitor used traditionally in a birthing center, or a monitor used in a gynecological doctor's office, hospital or clinic, and it communicates information back to the intravaginal monitoring device that is inserted into a vagina.

In another embodiment, the mode of operation includes a two way communication of instructions and data between the intravaginal monitoring device located in the vagina and the remote device. The archival images from a remote data storage source may also be communicated to the intravaginal monitoring device within the vagina and compared to images taken in real time or recently taken, whereby changes in cervical conditions are capable of being determined over the course of user's lifetime. The comparison of archival frames of the cervix or vagina are done with images taken in real time or more recent images to determine the health of the cervix or detect abnormalities in cervix structure or physiology. Alternatively, the comparison of archival physiological data taken within a vagina may be done with the data taken in real time or more recent data to determine the health of the cervix or detect abnormalities in cervix structure or physiology or determine the health of the female.

The female may also wear the intravaginal monitoring device over a course of her lifetime and in which images are made of her cervix as well as other information from within her vagina, and then compared with one or more times later in the female's life to track changes. This is done so as to monitor and track vaginal and or cervical health.

Here, the mode of operation also includes an operation that predicts using artificial intelligence algorithms, so that in this mode of operation predictions are made; the predictions including date and/or time to birth prediction, an expected clinical event prediction, a types of therapy needed or desired.

The intravaginal monitoring device, method and system of any of the disclosures herein in which there are features for, a member that is, and/or a mode of operation for one or more of the following: (i) a tethered wand; (ii) a sensor; (iii) a housing that is sized and dimensioned so that panties will hold it in place; (iv) fold over flaps to retain device for falling out; (v) a means so that the device can also be taped or held in place using an external retention system; (vi) a housing sized and dimensioned with a larger outside configuration can be bigger than the vaginal opening to stop it from going in too far; (vii) a warning mechanism to continuously or periodically determine position of device in birth canal; (viii) an alert module to provide warnings or alerts related to proper or improper insertion position; (ix) an alert or notification module to provide a user with an indication of how much time the unit should be kept in a user to obtain an appropriate amount of data for a proper understanding of a user's events or conditions and/or a clinically relevant histogram; (x) a housing so that the device is only partially insertable in the vagina in another variant; (xi) a easily cleanable housing; (l) a water or fluid repellent housing or coating on the housing; (xii) a memory to back up data collection of data in the event of non functioning or non available wireless or wired communication link for data transfer; (xiii) a mode of operation to back up data or keep a second copy of data; (xiv) a USB port; (xv) a mini USB port; (xvi) a real time data storage mode; (xvii) a mode of operation to locate the center of the cervix so the cervix is in a properly in the field of view; (xviii) a mode of operation providing for an alert or notification; (xix) one or more pressure sensors disposed on the device and a mode of operation to determine gripping strength of vaginal tissue; (xx) a mode of operation to determine if the device housing was pushed it in too far, at the proper position, or not in far enough into the vagina; (xxi) a camera and/or light source mode of operation including an infrared camera and light source mode of operation; (xxii) a visible light source and camera mode of operation; (xxiii) one or more camera assemblies disposed in any of the following location at distal end of housing, at the proximal end of housing, at an intermediate location within the housing, outside of the housing, at a location within housing to provide a proper focal length to cervix; (xxiv) a mode of operation to provide communication to user that cervix is not identified, or not properly identified, or properly identified; (xxv) a light source, no light source, a light source of any wavelength, one or more light emitting diodes emitting the same or different wavelengths of electromagnetic energy; (xxvi) receivers capable of detecting the energy; (xxvii) light sources used in conjunction with sensors and detectors herein; (xxviii) indicators on the device used to provide alters or notifications to expectant mother, father or obstetrician; (xxix) indicators on the device to indicate various events; (xxx) the events selected from the group consisting of being in womb movement, a time to get to birthing center, doctor, or hospital indicator; (xxxi) an opening of the cervix indicator; (xxxii) a distance sensor for indicating the location of the device in the vagina or in relation to the target cervix; (xxxiii) an indicator that the device or a remote device is functioning properly or communicating there between properly; (xxxiv) an optical distance measurement indicator; (xxxv) a CCD or CMOS camera array; (xxxvi) an image capture mode for capturing images of the cervix or other vaginal anatomical structure in one, two and or three dimensions; (xxxvii) a mode of operation for providing data related to the three dimensional contours of the cervix; (xxxviii) a mode of operation to track effacement of cervix; (xxxix) a mode of operation to determine dilation of cervix; (xxxx) a mode of operation to correlate and present data of cervical dilation and cervical effacement, simultaneously, or separately; (xxxxi) a mode of operation for baseline capture of internal images of woman's vagina and cervix, and/or physiological parameters at different points in time using the device, system and method of the present invention; (xxxxii) a mode of operation for identifying, and/or tracking abnormal growths on a female anatomy, tracking cysts, genital warts, and/or other growths in a females lower body, and reproductive organs, or any combination thereof.

The intravaginal monitoring device and system includes a parameter measuring tool, in which the device provides a data feed for an electronic record of this information over the course of a woman's lifetime (premenopausal, post menstrual to post menopausal, or any variant of a period of time there between).

The intravaginal monitoring device's and system's mode of operations may include detecting an abnormal event for a user of the device, or simply that the user has purchased and registered such a device, and the device or system or method provides the user a register of medical providers, e.g. doctor's, obstetricians, a GPS functionality in another variant to identify the nearest doctor or facility, location of a device, location of a user's cell phone, location of a third party, a mode of operation for patient scheduling and appointment, identifies which doctor has the earliest appointment available (helps relieve the stress for the patient). The intravaginal monitoring device's and system's mode of operations may also include a user or medical professional loading medical event information about the user, personal information about the user, medical record information about the user, information about the device, e.g. serial number, date of production, model type, information from another device of this type onto a new device, onto the device and system taken from another such device or a remote medical information diagnostic device.

The intravaginal monitoring device's and system's mode of operation includes a comparison of archival state of disease or event data with current state of disease or event data. The intravaginal monitoring device and system further consists of a display (or without a display), and one or more of the following features, alone or in combination: (i) an audible signal to user or other person of the orientation of the device; (ii) one or more emitters, working alone or in combination, used to assist one or more sensors, or light sources; (iii) a light source or emitter that can see through fluid discharge that may cover housing on device; (iv) a light source or emitter that emits in a direction other than the direction of the cervix; (v) a light source or emitter that emits backwards toward the vaginal opening, perpendicular to the axis of the vagina, or perpendicular to the cervix; (vi) an ultraviolet light source; (vii) a light source used to kill undesirable flora within the vagina; (viii) a light source or emitter used to reduce microbe count within the vagina; (ix) a light source used to kill a yeast; (x) a magnetic array, paired emitters and detectors.

The intravaginal monitoring device and system may also consist of speakers, and an optional music players and/or recorder; the music players may include a digital music player, an MP3, MP4 player, a music player playing educational music for a being in a womb, messages sent from the internet from family and friends to child, recording mothers words, songs and text the mother or father are saying and singing to the being while the being is in the womb, digital pictures of the family, mother, and father and other digitally stored information.

The intravaginal monitoring device and system may also consist of one way (in one variant) and (two way) information and instruction flow between the device and a remote device. The intravaginal monitoring device's and system's mode of operation may include a mode of operation that predicts timing of a birth or birth related event based upon the sensor and or camera input, or external statistical information gathered. The intravaginal monitoring device's and system's mode of operation may include a mode of operation that senses fluid discharge, optionally quantifies the fluid discharge, and or includes one or more fluid sensors. The intravaginal monitoring device's and system's mode of operation may include a mode of operation that places date and time stamps fluid discharge events.

The intravaginal monitoring device's and system's mode of operation may include a mode of operation that time and date stamps fluid discharge events and ranks the events as non problematic or problematic, and optionally sends an alert to a remote device, and or optionally creates a timeline or chronological record of each the event and the severity of the event.

The intravaginal monitoring device and system may further include of a cleanable lens. The intravaginal monitoring device's and system's functionality may include one or more of the following features: (i) image stabilization; (ii) image tracking; (iii) image tracking when device is inside the vagina only; (iv) an optical mode of operation for ensuring the location of sweet spot data; (v) a mode of operation for sonic data retrieval; (vi) a mode of operation that automatically adjusts for movement of mother due to walking or contractions; and (vii) a mode of operation that tracks movement of target cervix and device moving together, alone or in combination.

The intravaginal monitoring device's and system's mode of operation may include automatic communications pre-birth information of the mother and child prior to a hospital emergency room computer system, a birthing center emergency room. The intravaginal monitoring device's and system's mode of operation may include a false labor indicator. The intravaginal monitoring device's and system's mode of operation may include a spaced out labor indicator. The intravaginal monitoring device's and system's mode of operation may include labor and delivery patient management.

The intravaginal monitoring device and system, and its mode of operation may include, alone or in combination: (i) processing circuitry for processing the data; (ii) a mode of operation for continuously sending high definition video; (iii) a mode of operation where the device or components thereof activate if a relevant parameter changes; (iv) a mode of operation in which the device sends base image data and difference data to a remote device; (v) a mode of operation in which the device only send data if there are changes in the data; (vi) a mode of operation in which the device only sends data if there are clinically significant changes in data; and (vii) a mode of operation in which the device sends data if there are clinically significant changes to the data.

The intravaginal monitoring device's and system's mode of operation may include one in which every unit or device in or on the network including end device has maximum functionality.

The intravaginal monitoring device's and system's mode of operation may include a normal mode of operation, a dock mode of operation, a marry mode of operation, a periodic data harvesting mode of operation, a continuous data harvesting mode of operation, a full time video mode of operation, a mode of operation in which the device automatically figures out its proper positioning and location, a mode of operation in which the device signals by vibration that it is properly oriented, a mode of operation in which the device visually signals it is properly oriented, alone or in combination.

The intravaginal monitoring device's and system's mode of operation may include one that provides secure transfer of data, alone or in combination, a mode of operation that selectively manages or limits delivery of images to authorized remote devices, a mode of operation that automatically transfer data from the device to another preauthorized device upon a command received from the preauthorized device, a mode of operation that includes anti sniffing capability.

The intravaginal monitoring device's and system's mode of operation may include one in which the device that is insertable into the vagina automatically loads software or an application therefrom onto a user's computer and or a user's mobile phone or other electronic device, e.g. iPod, so that device can communicate and send data thereto, and receive data and instructions therefrom. The intravaginal monitoring device's and system's mode of operation may include one that tracks an expectant mother's physiological functions. The intravaginal monitoring device's and system's mode of operation may include one that tracks baby's physiological functions. The intravaginal monitoring device's and system's mode of operation may include one that provides drug delivery via the device or a remote device in response to data collected by the device such that contractions are slowed down or stopped. The intravaginal monitoring device's and system's mode of operation may include one that provides instructions to calm the woman directly by the device (the device has speakers directly thereon and a microphone) or through a mobile phone communicatively linked to the device, whereby the, and the stress on the expectant mother, expectant father, or other parties. The instructions may be provided in real time.

The intravaginal monitoring device's and system's mode of operation may include one that: based on measurements taken from the device, and/or based on information coming from outside the unit, the device (or associated remote device) provides a female or others instructions on how to manage the birthing process; the instructions including information such as a lay down instruction, a relax instruction, a deep breathing instruction, a medical protocol instruction, a push instruction, a hold instruction, a call an ambulance instruction, a call a 911 instruction, a stay off your feet instruction, a bed rest instruction, a medically relevant therapy instruction, a drug use instruction, a psychologically desired instruction, and an instruction to a third party.

The intravaginal monitoring device's and system's mode of operation may include ones that store all patients medical information, and optionally feed doctors and patients information back into the device or remote device, a mode of operation that provides a female's preexisting health condition information back into the device, get sent back and recorded into unit, e.g. hemophiliac, HPV, HIV, Hepatitis B, etc., heart conditions, hypertension, and any other medicals conditions, sex partner parameters, insurance company and coverage information, e.g. policy numbers, patient information, doctor information, billing information, pre-birth screening information, doctor's and patient's medical information is available from this device, and electronic medical records get downloaded into device. The intravaginal monitoring device's and system's mode of operation may include GPS electronics and GPS functionality.

The intravaginal monitoring device's and system's mode of operation may include, alone or in combination, with the following modes of operation: (i) the device that insertable uses a phone's or third party electronics GPS functionality; (ii) a mode of operation in which the device provides GPS Information to mobile phone; (iii) a mode of operation in which the device or mobile phone communicatively linked thereto tells you where a doctor is located; (iv) a mode of operation wherein the device or mobile phone associated therewith tells a doctor where patient is located; (v) a mode of operation that informs an expectant father where wife is located and route being taken by wife, e.g. by taxi or ambulance, to hospital or birthing center; (vi) a mode of operation that provides the route in real-time being taken by the mother to a birthing center or hospital so that the father and or doctor or other medical professional can catch up and meet; (vii) a mode of operation that informs the patient where the doctor is located and his or her route to the birthing event in real-time; and (viii) a mode of operation that informs all of the parties associated with the birthing event know the location of each other and their relative routes to the event.

The intravaginal monitoring device's and system's GPS mode of operation may include a mode of operation in which the device or husband's cell phone wakes up the husband or a third party and notifies them that a birthing event or other female event is about to occur, and notifies them the information such as the location of the nearest hospital or birthing center, the location of the doctor, the location of medical help, the location of the nearest fire department, information of the best and fastest route to take using the mobile phones GPS system, a mode of operation communicating with a mobile or automotive GPS system regarding the required information, e.g. nearest hospital, etc. and organizes the proper routing of all involved.

The intravaginal monitoring device's and system's mode of operation may include ones that includes an application and/or functionality used and described herein that is loaded onto a device, remote device or mobile phone used herein that includes SIM loaded data, tether loaded data, data downloaded from Internet, treatment data, therapy data, and drug data. The intravaginal monitoring device's and system's mode of operation may include ones that includes an application.

The intravaginal monitoring device's and system's mode of operation includes one that permits the parents to listen to child's heart beat and or see a sonogram real-time on a remote device, the remote device selected from the group consisting of a mobile phone, a smart phone, a web enabled device, a computer, a television screen, and a monitor.

The intravaginal monitoring device's and system's mode of operation includes ones that provide a graphical representation such as that of being in the womb representation, a cervix animation, a progression of cervical dilation animation, a progression of cervical effacement animation, a graphical representation of an cervical abnormality progression over time.

The intravaginal monitoring device's and system's mode of operation and hardware include a docking unit or platform. The docking unit or platform including one or more of the following modes of operation, alone or in combination: (i) a mode of operation in which the docking station or platform acts a gateway to another device or to another network; (ii) a mode of operation enabling the device to communicate to the Internet; (iii) a mode of operation enabling two or more communication interfaces, one to device, one to device beyond device; and (iv) a control signal mode of operation, in which the control signals are selected from the group consisting of image and sensor analysis control signals, processing control signals in which processing goes on in whole or in part in the device, control signals for controlling one or more cameras on the device, display control signals, data capture control signals, sensor function control signals, control signals turning on or off modes of operation of the device, data delivery control signals, rate of image capture control signals, periodicity of data harvest control signals, length of time of data capture control signals, delivery of data control signals, on device data storage control signals, vibrator control signals, alert control signals, notification control signals, audible control signals, speaker function control signals, music control signals, video control signals, need to reposition the device control signals, length of time of data harvest by the device control signals, control signals that enable a mode of operation of the device, characterization control signals, heart rate data harvest control signals, temperature data harvest control signals, being in womb data harvest control signals, heart rate data harvest control signals, irregular heart rate monitoring control signals, two way communication device from remote device and to device, memory in device management control signals, data transfer from device to remote unit control signals, alone or in combination.

The intravaginal monitoring device's and system's mode of operation include one that provides for distributed processing of captured data by the insertable device.

The intravaginal monitoring device's and system's mode of operation include one or more of the following, alone or in combination: (i) a communications channel a periodic update of firmware for the device mode of operation; (ii) a wireless hotspot enablement of communication with device mode of operation, a cell phone communication mode of operation; (iii) an emergency data from device to remote unit mode of operation; (iv) an emergency event trigger based alter data transfer mode of operation; (v) a push data out of device to remote unit mode of operation; (vi) a pull data of device to remote unit mode of operation; (vii) a mode of operation for sending data from the device outside to analysis group of computers; (viii) a mode of operation for sending data out of the device to a remote medical specialist or expert computer, location and or specialist medical center computer; (ix) a data routing mode of operation to route device data to one or more appropriate specialist hospital, doctor or medical professional for conditions that are developing in real time with a female and or a being in a womb; (x) a push data from device to outside wearable unit mode of operation; (xi) a heart rate sensor mode of operation to measure heart rate through an infrared LED and detector; (xii) a sensor processing mode of operation; (xiii) a temperature sensor processing mode of operation; (xiv) electronic microbe detecting mode of operation with microbe detecting electronics; (xv) an electronic DNA sensor mode of operation; (xvi) an electronic RNA sensor mode of operation; (xvii) an optical image sensor mode of operation; (xviii) an image stream processing mode of operation; (xix) a device removal string mode of operation; and (xx) a device removal string mode of operation whereby tension on the removal string activates or deactivates device functionality.

The intravaginal monitoring device's and system's mode of operation include, one or more of the following, alone or in combination: (i) timing circuitry mode of operation to provide a time association with captured information within the insertable device and/or external timing mechanism to provide such association; (ii) historic information presentation mode of operation using (#i) above; (iii) a microscope lensing mode of operation; (iv) a manual/auto-focus mode of operation for imaging cervical microbes; (v) software/firmware mode of operation for analyzing (#iii) images to classify bacteria type, and a mode of operation to generate microbe count information.

The intravaginal monitoring device's and system's mode of operation include, one or more of the following, alone or in combination: a light emitting diode mode of operation; in which light emission properties from the light emitting diode are managed to obtain a managed emission profile. The managed emission profile may include an intensity of light emission profile, a color of light emission profile, a wavelength of light emission profile, a time duration of light emission profile, an energy conservation profile by managing emission from the LED to conserve an energy source, and a therapy profile in which emission of light having a microbe reducing effect is provided.

The intravaginal monitoring device's and system's mode of operation may include, one or more of the following, alone or in combination: in which the light source is self powered, and in which includes a mode of operation to manage the light emission of the light source to conserve electrical energy of the device.

The intravaginal monitoring device's and system's mode of operation may include, one or more of the following, alone or in combination: a light source emitter, the light source emitter have an emission profile; the emission profile being selected from the group consisting of a the light source emission profile in the light in a visible spectrum, a light source emission profile emitting in the infrared spectrum of light, a light source emission profile in an ultraviolet spectrum of light.

The intravaginal monitoring device's and system's mode of operation may include, one or more of the following, alone or in combination: a ribbon or string, whereby a user sees the ribbon and/or string located outside the vagina; the ribbon or string providing a visual indication to a user reminding the user to remove the device from inside a patient.

The intravaginal monitoring device's and system's mode of operation may include, one or more of the following, alone or in combination: a light source is organized in an array, array consists of an array of LEDs.

In another embodiment, imaging device 211 (FIG. 2) is sized to be at least partially inserted within a vaginal channel 231 to reach a cervical region within the vaginal channel 231. The imaging device 211 includes a housing having a first portion and a second portion. An imager is disposed on the first portion of the housing. The first portion of the housing is sized to support imaging within the cervical region within the vaginal channel 231. The second portion of the housing is sized to at least partially conform to the vaginal channel 231, and the first portion has a maximum diameter greater than that of the second portion. As shown, by way of example in FIGS. 2, 6, 7, 9, 11, 12, 14, at least part of the first portion of the housing is optionally deformable so that insertion of the device is facilitated. The housing is sized and dimensioned to be fully insertable into the vaginal channel 231 (FIGS. 3 and 4). By way of further example, the housing is designed to be worn within the vaginal channel 231 (FIGS. 3 and 4).

In another embodiment, a cap 611, 621, 631, 2511, 2611 (FIGS. 6, 25 and 26) is used with a monitoring device (2513, 2613). The monitoring device has a first mechanical interface portion. The monitoring device is sized for at least partial insertion into a vaginal channel 231 of a female reproduction system. The monitoring device has an optical imager assembly. Exemplary caps 611, 621, 631, 2511, 2611 include a first cap region having a second mechanical interface portion sized such that the second mechanical interface portion matingly engages the first mechanical interface portion of the monitoring device. A second cap region is shaped to assist the optical image assembly of the monitoring device. The assistance includes attempting to maintain a minimum field of view. The assistance includes attempting to limit fluid from reaching the optical imager assembly (FIGS. 11 and 26). The second cap region is at optionally at least partially deformable (FIG. 14). In further embodiments, the second cap region comprises a bulbous shape or an asymmetric shape (FIGS. 11, 12, and 26).

In another embodiment, the cap is selected from one of a plurality of caps (FIGS. 6, 25, 26). Each of the plurality of caps have a different form factor from others of the plurality of caps (FIGS. 5, 6, 7, 11,12, 25 and 26). The cap is capable of progressive expansion (FIGS. 13 and 14).

In another embodiment and as illustrated in FIGS. 25 and 26, a kit is used at least in part to service any of a number of female reproductive systems. Each of female reproductive systems may have dimensional characteristics differing from each other, e.g. anatomical variations based upon race, height, weight, age, number of pregnancies, etc. The kit includes a number of exemplary caps 611, 621, 631, 2511, 2611 (FIGS. 6, 25, and 26), and each of the plurality of caps have a form factor as illustrated in the drawings herein, by way of example. The form factor of a first of the plurality of caps in a kit corresponds to the dimensional characteristic of a first of the plurality of female reproductive systems, and the form factor of a second of the plurality of caps corresponds to the dimensional characteristics of a second of the plurality of female reproductive systems. For example, a kit contains small, medium and large size caps. By way of further example, a selection of caps of different dimensions are provided based upon an assessment of a physician as to the greatest comfort level for a patient based upon a visual inspection of a woman by a physician or nurse. One of a group of caps are fitted by the woman or physician for greatest comfort, and optimal field of view for a particular woman. A monitoring device mechanically couples with the caps. Mechanical coupling is accomplished through a variety of means including, by way of example, a friction fit, tongue and groove appendages on the cap and housing, screw on assemblies. In one variant, the cap is made from flexible grade silicon which fits snuggly or stretches to secure tightly onto the device.

The kit optionally includes a plurality sleeves. The sleeves are placed over the entire imaging device, e.g. cap and stem, in one embodiment. The sleeves are hygienic and disposable so that the device does not get contaminated by bodily fluids or microbes. The sleeves are constructed of transparent or translucent polymeric material. Optionally, the kit includes the electronic stem of an intravaginal imaging device, and a carrying case. The carrying case is of a form such as a woman's clutch, purse or cosmetic case, and serves to permit the woman to carry the kit components in a larger purse without risk of contamination of the kit components or of the inside of the larger purse with bodily fluids or other contaminants. The carrying case optionally as interior pockets or cavities to store the kit components such as caps, sleeves, imaging stem (FIGS. 25 and 26), support device, e.g. iPhone, smart phone, iTouch, or other supporting device. The carrying case optionally has an exterior pocket or cavity so that the screen of the supporting device is visable, but removably secured to the carrying case. A separate compartment on the carrying is optionally zippered and opens to reveal the kit components other than support device. The carrying case is made of a polymeric material, cloth, leather, a metal, e.g. stainless steel, or other suitable material. The inside of the carrying case includes contains a cavity with a polymer lining, and optionally, a lining that has antimicrobiable properties. In another variant, one of the plurality of caps provides a unimpeded optical pathway there through (FIGS. 8, 9, and 12), and optionally, one of the plurality of caps has a substantially transparent portion (FIG. 26) to provide an optical pathway there through.

The terms "circuit" and "circuitry" as used herein may refer to an independent circuit or to a portion of a multifunctional circuit that performs multiple underlying functions. For example, depending on the embodiment, processing circuitry may be implemented as a single chip processor or as a plurality of processing chips. Likewise, a first circuit and a second circuit may be combined in one embodiment into a single circuit or, in another embodiment, operate independently perhaps in separate chips. The term "chip", as used herein, refers to an integrated circuit. Circuits and circuitry may comprise general or specific purpose hardware, or may comprise such hardware and associated software such as firmware or object code.

As one of ordinary skill in the art will appreciate, the terms "operably coupled" and "communicatively coupled," as may be used herein, include direct coupling and indirect coupling via another component, element, circuit, or module where, for indirect coupling, the intervening component, element, circuit, or module does not modify the information of a signal but may adjust its current level, voltage level, and/or power level. As one of ordinary skill in the art will also appreciate, inferred coupling (i.e., where one element is coupled to another element by inference) includes direct and indirect coupling between two elements in the same manner as "operably coupled" and "communicatively coupled."

The present invention has also been described above with the aid of method steps illustrating the performance of specified functions and relationships thereof. The boundaries and sequence of these functional building blocks and method steps have been defined herein for convenience of description. Alternate boundaries and sequences can be defined so long as the specified functions and relationships are appropriately performed. Any such alternate boundaries or sequences are thus within the scope and spirit of the claimed invention.

The present invention has been described above with the aid of functional building blocks illustrating the performance of certain significant functions. The boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention.

One of average skill in the art will also recognize that the functional building blocks, and other illustrative blocks, modules and components herein, can be implemented as illustrated or by discrete components, application of specific integrated circuits, processors executing appropriate software and the like or any combination thereof.

Moreover, although described in detail for purposes of clarity and understanding by way of the aforementioned embodiments, the present invention is not limited to such embodiments. It will be obvious to one of average skill in the art that various changes and modifications may be practiced within the spirit and scope of the invention, as limited only by the scope of the appended claims.

We claim:

1. A self-powered, removable, electronic sensor device sized to be inserted within a vaginal channel to image a cervical region within the vaginal channel, the sensor device comprising:
   a housing having a first portion and a second portion, the first portion of the housing being at least partially deformable and balloonless;
   a sensor disposed in the first portion of the housing;
   the first portion of the housing being sized to support sensing within the cervical region within the vaginal channel;

the second portion of the housing being sized to at least partially conform to the vaginal channel; and, the sensor device having a first mode of operation within the sensor device for capturing and wirelessly communicating image sensor data to a geographically remote receiving device, the first mode of operation adapted for sending the image sensor data to a smart phone or tablet, and a second mode of operation adapted for operating the sensor device in a female reproductive condition specific manner and being downloadable to the sensor device from a server.

2. The sensor device of claim 1, wherein at least part of the first portion of the housing is movably connected to the second portion of the housing.

3. The sensor device of claim 1, wherein the entire sensor device is sized and dimensioned to completely fit within the vaginal channel.

4. The sensor device of claim 1, wherein the entire sensor device is sized to be worn within the vaginal channel.

5. A self-powered, removable, electronic sensor device sized to be inserted within a vaginal channel to image a cervical region within the vaginal channel, the sensor device comprising:
at least a partially deformable, balloonless housing having a first portion and a second portion;
a sensor disposed on the first portion of the housing;
the first portion of the housing being sized to support sensing within the cervical region within the vaginal channel; and,
the second portion of the housing being sized to at least partially conform to the vaginal channel; and, the sensor device having a first mode of operation for communicating sensor data to a geographically remote receiving device, and a second mode of operation for assisting in interacting with a global positioning system application.

6. The sensor device of claim 5, in which the sensor device further comprises a mode of operation for assisting in interacting with an advertising related server.

7. The sensor device of claim 5 further in which the sensor device further comprises a mode of operation for assisting in interacting with a sales related server.

8. The sensor device of claim 5 in which the sensor device further comprises a mode of operation for interacting with a female reproductive application server hosting a plurality of applications, the plurality of applications selected from the group consisting of smartphone applications and tablet applications.

9. The sensor device of claim 8 in which the plurality of applications is selected from the group of non-pregnancy related applications and pregnancy related applications.

10. The sensor device of claim 5 further comprising a fluid delivery member.

11. The sensor device of claim 5 further comprising an external electronic patch interacting mode of operation.

12. A self-powered, removable, electronic sensor device sized to be inserted within a vaginal channel to image a cervical region within the vaginal channel, the sensor device comprising:
at least a partially deformable, balloonless housing having a first portion and a second portion;
a sensor disposed on the first portion of the housing;
the first portion of the housing being sized to support sensing within the cervical region within the vaginal channel; and,
the second portion of the housing being sized to at least partially conform to the vaginal channel; and, the sensor device having a first mode of operation for communicating sensor data to a geographically remote receiving device, and a second mode of operation for interacting with a female reproductive application server hosting a plurality of applications, the plurality of applications selected from the group consisting of smart phone applications and tablet applications.

13. The sensor device of claim 12 in which the plurality of applications is selected from the group of non-pregnancy related applications and pregnancy related applications.

14. The sensor device of claim 12 further comprising a mode of operation for assisting in GPS navigation.

15. The sensor device of claim 12 further comprising a mode of operation for assisting in advertising.

16. The sensor device of claim 12 further comprising a mode of operation for assisting in sales.

17. The sensor device of claim 12 further comprising a removable cap.

18. The sensor device of claim 12 in which the plurality of applications comprise a non-human female pregnancy related application.

19. The sensor device of claim 12 in which the plurality of applications comprise a non-human female insemination related application.

20. The sensor device of claim 12 in which the plurality of applications comprise a human female insemination related application.

21. The sensor device of claim 12 in which the plurality of applications comprise a female conception related application.

22. The sensor device of claim 21 in which the female conception related application is selected from the group consisting of a non-human female conception related application and a human female conception related application.

23. The sensor device of claim 22 further comprising a semen delivery member.

* * * * *